(12) United States Patent
Costantino et al.

(10) Patent No.: US 9,441,004 B2
(45) Date of Patent: Sep. 13, 2016

(54) **PURIFICATION OF *STAPHYLOCOCCUS AUREUS* TYPE 8 CAPSULAR SACCHARIDES**

(71) Applicant: GlaxoSmithKline Biologicals SA, Rixensart (BE)

(72) Inventors: Paolo Costantino, Colle Val D'Elsa (IT); Maria Rosaria Romano, Pontedera (IT); Francesco Berti, Colle Val D'Elsa (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 14/714,097

(22) Filed: May 15, 2015

(65) Prior Publication Data

US 2015/0315225 A1  Nov. 5, 2015

Related U.S. Application Data

(62) Division of application No. 13/504,920, filed as application No. PCT/IB2010/054934 on Nov. 1, 2010, now Pat. No. 9,060,965.

(60) Provisional application No. 61/256,905, filed on Oct. 30, 2009.

(51) Int. Cl.
*A61K 47/48* (2006.01)
*A61K 39/00* (2006.01)
(Continued)

(52) U.S. Cl.
CPC ............... *C07H 1/08* (2013.01); *A61K 39/085* (2013.01); *C12P 19/04* (2013.01); *A61K 2039/55505* (2013.01); *A61K 2039/6037* (2013.01)

(58) Field of Classification Search
CPC .................................................. A61K 39/085

USPC ............................... 424/193.1, 197.11, 243.1
See application file for complete search history.

(56) References Cited

U.S. PATENT DOCUMENTS 2,166,963 A * 7/1939 Masucci ............... A61K 39/02
424/244.1
3,269,913 A  8/1966 Devlin et al.
(Continued)

FOREIGN PATENT DOCUMENTS

GB  992132 A  5/1965
GB  995338 A  6/1965
(Continued)

OTHER PUBLICATIONS

Kropec, Andrea et al, Infection and Immunity, Oct. 2005, pp. 6868-6876, vol. 73(10), Poly-N-Acetylgl,ucosamine Production in *Staphylococcus aureus* Is Essential for Virulence in Murine Models ofSystemic Infection.*

(Continued)

*Primary Examiner* — Albert Navarro
*Assistant Examiner* — Ginny Portner
(74) *Attorney, Agent, or Firm* — Morrison & Foerster LLP

(57) ABSTRACT

The invention provides a method for releasing capsular polysaccharide from *S. aureus* type 5 or type 8 cells, comprising the step of treating the cells with acid. The invention further provides a process for purifying capsular polysaccharide from *S. aureus* type 5 or type 8 cells comprising this method. Other processing steps may be included in the process, such as enzymatic treatment, e.g. to remove nucleic acid, protein and/or peptidoglycan contaminants; diafiltration, e.g. to remove low molecular weight contaminants; anion exchange chromatography, e.g. to remove residual protein; and concentration.

21 Claims, 9 Drawing Sheets

(51) Int. Cl.
*C07H 1/08* (2006.01)
*C12P 19/04* (2006.01)
*A61K 39/085* (2006.01)

(56) References Cited

U.S. PATENT DOCUMENTS

| | | | |
|---|---|---|---|
| 4,663,160 A | 5/1987 | Tsay et al. | |
| 4,808,700 A | 2/1989 | Anderson et al. | |
| 5,679,654 A | 10/1997 | Tzianabos et al. | |
| 5,866,140 A * | 2/1999 | Fattom | C12P 19/04 424/184.1 |
| 6,027,733 A * | 2/2000 | Wang | A61K 39/0216 424/234.1 |
| 6,045,805 A | 4/2000 | Moreau | |
| 6,274,144 B1 | 8/2001 | Wang | |
| 6,294,177 B1 | 9/2001 | Fattom | |
| 6,537,577 B1 | 3/2003 | Siegel | |
| 6,689,567 B1 * | 2/2004 | Lam | C12N 9/88 435/232 |
| 6,855,321 B1 * | 2/2005 | Rappuoli | C07K 14/005 424/184.1 |
| 6,896,887 B2 | 5/2005 | Leenhouts et al. | |
| 7,015,007 B2 | 3/2006 | Pier | |
| 7,067,639 B2 | 6/2006 | Leenhouts et al. | |
| 7,252,828 B2 | 8/2007 | Pier et al. | |
| 7,538,207 B2 | 5/2009 | Rappuoli | |
| 7,541,039 B2 | 6/2009 | Leenhouts et al. | |
| 7,582,459 B2 | 9/2009 | Hamidi et al. | |
| 7,842,479 B2 | 11/2010 | Bayles | |
| 7,858,357 B2 | 12/2010 | Leenhouts et al. | |
| 8,048,432 B2 * | 11/2011 | Lee | A61K 39/00 424/234.1 |
| 8,163,296 B2 | 4/2012 | Capannoli et al. | |
| 8,329,184 B2 | 12/2012 | Biemans et al. | |
| 8,338,137 B2 * | 12/2012 | Rokbi | A61K 39/085 424/237.1 |
| 8,377,451 B2 | 2/2013 | Pavliak et al. | |
| 8,568,735 B2 * | 10/2013 | Anderson | A61K 39/085 424/165.1 |
| 8,598,337 B2 | 12/2013 | Michon | |
| 8,663,654 B2 | 3/2014 | Pier et al. | |
| 8,679,812 B2 | 3/2014 | Shiga | |
| 8,858,955 B2 * | 10/2014 | Biemans | A61K 39/385 424/193.1 |
| 8,974,799 B2 * | 3/2015 | Berti | A61K 47/48261 424/194.1 |
| 9,060,965 B2 * | 6/2015 | Costantino | A61K 39/085 |
| 9,114,105 B2 * | 8/2015 | Anderson | A61K 39/085 |
| 9,125,951 B2 * | 9/2015 | Freese | A61K 39/085 |
| 2002/0179166 A1 * | 12/2002 | Houston | A61F 2/06 138/39 |
| 2003/0113350 A1 * | 6/2003 | Fattom | A61K 39/085 424/243.1 |
| 2004/0141986 A1 | 7/2004 | Parizek et al. | |
| 2005/0118198 A1 | 6/2005 | Pier et al. | |
| 2005/0250821 A1 | 11/2005 | Sewalt et al. | |
| 2006/0121058 A1 | 6/2006 | Malley et al. | |
| 2006/0251670 A1 | 11/2006 | Comanducci et al. | |
| 2008/0240978 A1 | 10/2008 | Sorensen et al. | |
| 2009/0136547 A1 | 5/2009 | Telford et al. | |
| 2010/0022015 A1 * | 1/2010 | D'Ascenzi | G01N 33/5308 436/94 |
| 2010/0136041 A1 * | 6/2010 | Grandi | A61K 39/092 424/190.1 |
| 2010/0143399 A1 * | 6/2010 | Biemans | A61K 39/385 424/197.11 |
| 2011/0262477 A1 | 10/2011 | Cheng et al. | |
| 2012/0128719 A1 | 5/2012 | Baker et al. | |
| 2012/0141523 A1 | 6/2012 | Castado et al. | |
| 2012/0237549 A1 * | 9/2012 | Berti | A61K 47/48261 424/243.1 |
| 2012/0276137 A1 * | 11/2012 | Freese | A61K 39/085 424/197.11 |
| 2012/0308600 A1 | 12/2012 | Costantino et al. | |

FOREIGN PATENT DOCUMENTS

| | | | |
|---|---|---|---|
| WO | WO-99/42130 A1 | 8/1999 | |
| WO | WO-2004/080490 A2 | 9/2004 | |
| WO | WO-2005/000346 A1 | 1/2005 | |
| WO | WO-2006/032475 A2 | 3/2006 | |
| WO | WO-2006/032500 A2 | 3/2006 | |
| WO | WO-2006/065553 A2 | 6/2006 | |
| WO | WO-2006/114500 A2 | 11/2006 | |
| WO | WO-2007/000343 A2 | 1/2007 | |
| WO | WO-2007/084856 A2 | 7/2007 | |
| WO | 2007/113223 * | 10/2007 | ........... A61K 39/085 |
| WO | WO-2007/113222 A2 | 10/2007 | |
| WO | 2008/081014 * | 7/2008 | ............. A61K 30/00 |
| WO | 2008/081022 * | 7/2008 | ........... A61K 39/095 |
| WO | WO-2008/081022 A1 | 7/2008 | |

OTHER PUBLICATIONS

Joyce, Joseph G. et al, Carbohydrate Research, vol. 338, 2003, pp. 903-922, Isolation, structural characterization and immunological evaluation of a high molecular weight exopolysaccharide from *Staphylococcus aureaus*.*

Akiyama, Hisanori et al, Effects of acetic acid on biofilms formed by *Staphylococcus aureus*, Archives of Dermatological Research, vol. 291(10), Oct. 1999, pp. 570-573.*

Fattom et al, Infection and Immunity, vo. 61, pp. 1023-1032, 1993.*

Snowden, Michael A. et al, Journal of General Microbiology, 1991, vol. 137, pp. 1661-1666, Cross-linking and O-acetylation of peptidoglycan in Staph (strains H and MR-1) grown in the presence of sub-growth concentrations of B-lactam antibiotics.*

Jones, Christopher, Carbohydrte Research, vol. 340, pp. 1097-1106, 2005, Revised structures of the capsular polysaccharide from *Staphylococcu aureus* Types 5 and 8, components of novel glycoconjugate vaccines.*

Moynihsn, Patrick J. et al, Analytical Biochemistry, vol. 439, pp. 73-79, 2013, Assay for peptidoglycan O-acetyltransferase:A potential new antibacterial target.*

Examination Report, mailed on Jun. 5, 2014, for EP 2493498, filed on Nov. 1, 2010. 8 pages.

Henning et al. (1982). "Praktische Chemie," VEB Verlag Volk and Gesundheit, Berlin, pp. 514-515, 540-541.

Park et al. (1960). "A Fractionation Procedure for Studies of the Synthesis of Cell-Wall Mucopeptide and of Other polymers in cells of *Staphylococcus aureus*," Journal of General Microbiology, vol. 22, pp. 249-258.

Strominger et al. (1959). "Composition of the Cell Wall of *Staphylococcus aureus*: Its Relation to the Mechanism of Action of Penicillin," The Journal of Biological Chemistry, 234(12):3263-8.

Akiyama et al (1999), Archives of Dermatology Research, vol. 291(10) Oct. 1999, pp. 570-573, Effects of acetic acid on biofilms formed by *Staphylococcus aureus*.

Baird-Parker, Tony C, Chapter 4 7, Foodborne Pathogens, Part 111, *Staphylococcus aureus*, pp. 1317-1330, 2000.

Cescutti et al. (Jul. 1996). "Determination of the size and degree of acetyl substitution of oligosaccharides from Neisseria meningitidis group A by ionspray mass spectrometry," Biochem Biophys Res Commun. 224(2):444-450.

Deng et al. (Mar. 2000). "Characterization of the linkage between the type III capsular polysaccharide and the bacterial cell wall of group B *Streptococcus*," J Biol Chem. 275(11):7497-7504.

Fattom et al (1990), July, Infection and Immunity, vol. 58(7), pp. 2367-2374.

Fattom et al. (1993). "Epitopic overload at the site of injection may result in suppression of the immune response to combined capsular polysaccharide conjugate vaccines," Vaccine 17(2):126-33.

Fattom et al. (1993). "Laboratory and clinical evaluation of conjugate vaccines composed of *Staphylococcus aureus* type 5 and type 8 capsular polysaccharides bound to Pseudomonas aeruginosa recombinant exoprotein A," Infect Immun. 61(3):1023-32.

Fattom et al. (1996). "A *Staphylococcus aureus* capsular polysaccharide (CP) vaccine and CP-specific antibodies protect mice against bacterial challenge," Infect Immun. 64(5):1659-65.

(56) References Cited

OTHER PUBLICATIONS

Fattom et al. (1998). "Antigenic determinants of *Staphylococcus aureus* type 5 and type 8 capsular polysaccharide vaccines," Infect Immun. 66(10):4588-92.

Fattom et al. (Feb. 1992). "Comparative immunogenicity of conjugates composed of the *Staphylococcus aureus* type 8 capsular polysaccharide bound to carrier proteins by adipic acid dihydrazide or N-succinimidyl-3-(2-pyridyldithio)propionate," Infect Immun. 60(2):584-589.

Fattom et al. (Jul. 1990). "Synthesis and immunologic properties in mice of vaccines composed of *Staphylococcus aureus* type 5 and type 8 capsular polysaccharides conjugated to Pseudomonas aeruginosa exotoxin A," Infect Immun. 58(7): 2367-2374.

Fattom, et al, (1993), Infection and Immunity, vol. 61 (3), pp. 1023-1032.

Fournier et al. (Jul. 1984). "Purification and characterization of *Staphylococcus aureus* type 8 capsular polysaccharide," Infect Immun. 45(1): 87-93.

Fox, Karen Fetal, Infection and Immunity, Aug. 1998, vol. 66(8), pp. 4004-4007, Synthesis of Microcapsule by *Staphylococcus aureus* Is Not Responsive to Environmental Phosphate Concentrations.

Gilbert et al. (1994) J. Microb. Meth. 20:39-46.

Gilbert et al. (1994). "Immunogenicity in cows of *Staphylococcus aureus* type 5 capsular polysaccharide-ovalbumin conjugate," Vaccine. 12(4):369-74.

Gilbert et al. (Jun. 1994). "Purification of type 5 capsular polysaccharide from *Staphylococcus aureus* by a simple efficient method," Journal of Microbiological Methods 20(1): 39-46.

International Preliminary Report on Patentability, mailed on Feb. 17, 2012, for PCT Patent Application No. PCT/IB2010/054934, filed on Nov. 1, 2010. 5 pages.

International Search Report, mailed on Mar. 2, 2011, for PCT Patent Application No. PCT/IB2010/054934, filed on Nov. 1, 2010, 5 pages.

Jennings (Jun. 1992). "Further approaches for optimizing polysaccharide-protein conjugate vaccines for prevention of invasive bacterial disease," J Infect Dis. 165 Suppl 1:S156-159.

Joyce, J. G. et al, Carbohydrate Research, vol. 338, 2003, pp. 903-922, Isolation, structural characterization, and immunological evaluation of a high molecular weight exopolysaccharide from *Staphylococcus aureus*.

Karakawa, WW et al, Infection and Immunity, vol. 9(3), Mar. 1974, pp. 511-518, Isolation of an Acidic Surface Antigen from a Conventional Strain of *Staphylococcus aureus*.

Karakawa, WW et al, Method for the Serological typing of the capsular polysaccharide of *Staphylococcus aureus*, Journal of Clinical Microbiology, Sep. 1985, pp. 445-447, vol. 22(3).

Lee et al. (1993). "Effects of in vitro and in vivo growth conditions on expression of type 8 capsular polysaccharide by *Staphylococcus aureus*," Infect Immun. 61(5): 1853-1858.

Lefeber et al. (Apr. 2002). "Isolation of oligosaccharides from a partial-acid hydrolysate of pneumococcal type 3 polysaccharide for use in conjugate vaccines," Carbohydr Res. 337(9):819-825.

Moreau, M et al, Carbohydrate Research, vol. 201 (2), Jul. 1990, pp. 285-297, Structure of the type 5 capsular polysaccharide of *Staphylococcus aureus*.

Raftari, M et al, Jan. 2009, The Open Microbiology Journal, vol. 3, pp. 121-127, Effect of Organic Acids on *Escherichia coli* 0157:H7 and *Staphylococcus aureus* contaminated Meat.

Robbins et al. (2005). "Prevention of systemic infections caused by group B *Streptococcus* and *Staphylococcus aureus* by multivalent polysaccharide-protein conjugate vaccines," Ann N Y Acad Sci. 754:68-82.

Shinefield et al. (2002). "Use of a *Staphylococcus aureus* conjugate vaccine in patients receiving hemodialysis," N Engl J Med. 346(7):491-6.

Tollersrud et al. (2001). "*Staphylococcus aureus* capsular polysaccharide type 5 conjugate and whole cell vaccines stimulate antibody responses in cattle," Vaccine. 19(28-29):3896-903.

Tzianabos et al, Structural rationale for the modulation of abscess formation by *Staphylococcus aureus* capsular polysaccharides, PNAS, Jul. 31, 2001, vol. 98(16) pp. 9365-9370.

Welch et al. (1996). "Safety and immunogenicity of *Staphylococcus aureus* type 5 capsular polysaccharide-Pseudomonas aeruginosa recombinant exoprotein A conjugate vaccine in patients on hemodialysis," J Am Soc Nephrol. 7(2):247-53.

Wunschel, DS et al, Journal of Chromatography A, vol. 776, 1997, pp. 205-219, Quantitative analysis of neutral and acidic sugars in whole bacterial cell hydrolysates using high-performance anion-exchange liquid chromatography-electrospray ionization tandem mass spectrometry.

\* cited by examiner

SEQUENCE LISTING

<160> NUMBER OF SEQ ID NOS: 54

<210> SEQ ID NO 1
<211> LENGTH: 927
<212> TYPE: PRT
<213> ORGANISM: Staphylococcus aureus

<400> SEQUENCE: 1

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

```
Ala Pro Lys Thr Asp Asp Thr Asn Val Ser Asp Thr Lys Thr Ser Ser
 65                  70                  75                  80

Asn Thr Asn Asn Gly Glu Thr Ser Val Ala Gln Asn Pro Ala Gln Gln
                 85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480
```

-continued

```
Asp Gln Ile Thr Thr Pro Tyr Ile Val Val Asn Gly His Ile Asp
                    485             490             495
Pro Asn Ser Lys Gly Asp Leu Ala Leu Arg Ser Thr Leu Tyr Gly Tyr
        500             505             510
Asn Ser Asn Ile Ile Trp Arg Ser Met Ser Trp Asp Asn Glu Val Ala
            515             520             525
Phe Asn Asn Gly Ser Gly Ser Gly Asp Gly Ile Asp Lys Pro Val Val
530             535             540
Pro Glu Gln Pro Asp Glu Pro Gly Glu Ile Glu Pro Ile Pro Glu Asp
545             550             555             560
Ser Asp Ser Asp Pro Gly Ser Asp Ser Gly Ser Asp Ser Asn Ser Asp
                565             570             575
Ser Gly Ser Asp Ser Gly Ser Asp Ser Thr Ser Asp Ser Gly Ser Asp
                580             585             590
Ser Ala Ser Asp Ser Asp Ser Ala Ser Asp Ser Asp Ser Ala Ser Asp
                595             600             605
Ser Asp Ser Ala Ser Asp Ser Asp Ser Ala Ser Asp Ser Asp Ser Asp
                610             615             620
Asn Asp Ser Asp Ser Asp Ser Asp Ser Asp Ser Asp Ser Asp Ser Asp
625             630             635             640
Ser Asp Ser Asp Ser Asp Ser Asp Ser Asp Ser Asp Ser Asp Ser Asp
                645             650             655
Ser Asp Ser Asp Ser Asp Ser Asp Ser Asp Ser Asp Ser Asp Ser Asp
                660             665             670
Ser Asp Ser Asp Ser Asp Ser Asp Ser Asp Ser Asp Ser Asp Ser Asp
                675             680             685
Ser Asp Ser Asp Ser Asp Ser Asp Ser Asp Ser Asp Ser Asp Ser Asp
                690             695             700
Ser Asp Ser Asp Ser Asp Ser Asp Ser Asp Ser Asp Ser Asp Ser Asp
705             710             715             720
Ser Asp Ser Asp Ser Asp Ser Asp Ser Asp Ser Asp Ser Asp Ser Asp
                725             730             735
Ser Asp Ser Asp Ser Asp Ser Asp Ser Asp Ser Asp Ser Asp Ser Asp
                740             745             750
Ser Asp Ser Asp Ser Asp Ser Asp Ser Asp Ser Asp Ser Asp Ser Ala
                755             760             765
Ser Asp Ser Asp Ser Asp Ser Asp Ser Asp Ser Asp Ser Asp Ser Asp
                770             775             780
Ser Asp Ser Asp Ser Asp Ser Asp Ser Asp Ser Asp Ser Asp Ser Asp
785             790             795             800
Ser Asp Ser Asp Ser Asp Ser Glu Ser Asp Ser Asp Ser Asp Ser Asp
                805             810             815
Ser Asp Ser Asp Ser Asp Ser Asp Ser Asp Ser Asp Ser Asp Ser Ala
                820             825             830
Ser Asp Ser Asp Ser Gly Ser Asp Ser Asp Ser Ser Ser Asp Ser Asp
                835             840             845
Ser Glu Ser Asp Ser Asn Ser Asp Ser Glu Ser Val Ser Asn Asn Asn
                850             855             860
Val Val Pro Pro Asn Ser Pro Lys Asn Gly Thr Asn Ala Ser Asn Lys
865             870             875             880
Asn Glu Ala Lys Asp Ser Lys Glu Pro Leu Pro Asp Thr Gly Ser Glu
                885             890             895
Asp Glu Ala Asn Thr Ser Leu Ile Trp Gly Leu Leu Ala Ser Ile Gly
```

900                 905                 910
Ser Leu Leu Leu Phe Arg Arg Lys Lys Glu Asn Lys Asp Lys Lys
            915                 920                 925

<210> SEQ ID NO 2
<211> LENGTH: 520
<212> TYPE: PRT
<213> ORGANISM: Staphylococcus aureus

<400> SEQUENCE: 2

Ser Glu Asn Ser Val Thr Gln Ser Asp Ser Ala Ser Asn Glu Ser Lys
1               5                   10                  15

Ser Asn Asp Ser Ser Val Ser Ala Ala Pro Lys Thr Asp Asp Thr
            20                  25                  30

Asn Val Ser Asp Thr Lys Thr Ser Ser Asn Thr Asn Asn Gly Glu Thr
            35                  40                  45

Ser Val Ala Gln Asn Pro Ala Gln Gln Glu Thr Thr Gln Ser Ser Ser
    50                  55                  60

Thr Asn Ala Thr Thr Glu Glu Thr Pro Val Thr Gly Glu Ala Thr Thr
65                  70                  75                  80

Thr Thr Thr Asn Gln Ala Asn Thr Pro Ala Thr Thr Gln Ser Ser Asn
                85                  90                  95

Thr Asn Ala Glu Glu Leu Val Asn Gln Thr Ser Asn Glu Thr Thr Ser
                100                 105                 110

Asn Asp Thr Asn Thr Val Ser Ser Val Asn Ser Pro Gln Asn Ser Thr
            115                 120                 125

Asn Ala Glu Asn Val Ser Thr Thr Gln Asp Thr Ser Thr Glu Ala Thr
    130                 135                 140

Pro Ser Asn Asn Glu Ser Ala Pro Gln Ser Thr Asp Ala Ser Asn Lys
145                 150                 155                 160

Asp Val Val Asn Gln Ala Val Asn Thr Ser Ala Pro Arg Met Arg Ala
                165                 170                 175

Phe Ser Leu Ala Ala Val Ala Ala Asp Ala Pro Val Ala Gly Thr Asp
                180                 185                 190

Ile Thr Asn Gln Leu Thr Asn Val Thr Val Gly Ile Asp Ser Gly Thr
            195                 200                 205

Thr Val Tyr Pro His Gln Ala Gly Tyr Val Lys Leu Asn Tyr Gly Phe
    210                 215                 220

Ser Val Pro Asn Ser Ala Val Lys Gly Asp Thr Phe Lys Ile Thr Val
225                 230                 235                 240

Pro Lys Glu Leu Asn Leu Asn Gly Val Thr Ser Thr Ala Lys Val Pro
                245                 250                 255

Pro Ile Met Ala Gly Asp Gln Val Leu Ala Asn Gly Val Ile Asp Ser
                260                 265                 270

Asp Gly Asn Val Ile Tyr Thr Phe Thr Asp Tyr Val Asn Thr Lys Asp
            275                 280                 285

Asp Val Lys Ala Thr Leu Thr Met Pro Ala Tyr Ile Asp Pro Glu Asn
    290                 295                 300

Val Lys Lys Thr Gly Asn Val Thr Leu Ala Thr Gly Ile Gly Ser Thr
305                 310                 315                 320

Thr Ala Asn Lys Thr Val Leu Val Asp Tyr Glu Lys Tyr Gly Lys Phe
                325                 330                 335

Tyr Asn Leu Ser Ile Lys Gly Thr Ile Asp Gln Ile Asp Lys Thr Asn
            340                 345                 350

```
Asn Thr Tyr Arg Gln Thr Ile Tyr Val Asn Pro Ser Gly Asp Asn Val
            355                 360                 365

Ile Ala Pro Val Leu Thr Gly Asn Leu Lys Pro Asn Thr Asp Ser Asn
    370                 375                 380

Ala Leu Ile Asp Gln Gln Asn Thr Ser Ile Lys Val Tyr Lys Val Asp
385                 390                 395                 400

Asn Ala Ala Asp Leu Ser Glu Ser Tyr Phe Val Asn Pro Glu Asn Phe
                405                 410                 415

Glu Asp Val Thr Asn Ser Val Asn Ile Thr Phe Pro Asn Pro Asn Gln
            420                 425                 430

Tyr Lys Val Glu Phe Asn Thr Pro Asp Asp Gln Ile Thr Thr Pro Tyr
        435                 440                 445

Ile Val Val Val Asn Gly His Ile Asp Pro Asn Ser Lys Gly Asp Leu
    450                 455                 460

Ala Leu Arg Ser Thr Leu Tyr Gly Tyr Asn Ser Asn Ile Ile Trp Arg
465                 470                 475                 480

Ser Met Ser Trp Asp Asn Glu Val Ala Phe Asn Asn Gly Ser Gly Ser
                485                 490                 495

Gly Asp Gly Ile Asp Lys Pro Val Val Pro Glu Gln Pro Asp Glu Pro
            500                 505                 510

Gly Glu Ile Glu Pro Ile Pro Glu
        515                 520

<210> SEQ ID NO 3
<211> LENGTH: 877
<212> TYPE: PRT
<213> ORGANISM: Staphylococcus aureus

<400> SEQUENCE: 3

Met Lys Lys Arg Ile Asp Tyr Leu Ser Asn Lys Gln Asn Lys Tyr Ser
  1               5                  10                  15

Ile Arg Arg Phe Thr Val Gly Thr Thr Ser Val Ile Val Gly Ala Thr
             20                  25                  30

Ile Leu Phe Gly Ile Gly Asn His Gln Ala Gln Ala Ser Glu Gln Ser
         35                  40                  45

Asn Asp Thr Thr Gln Ser Ser Lys Asn Asn Ala Ser Ala Asp Ser Glu
     50                  55                  60

Lys Asn Asn Met Ile Glu Thr Pro Gln Leu Asn Thr Thr Ala Asn Asp
 65                  70                  75                  80

Thr Ser Asp Ile Ser Ala Asn Thr Asn Ser Ala Asn Val Asp Ser Thr
                 85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205
```

```
Asp Ala Lys Gly Thr Asn Val Asn Asp Lys Val Thr Ala Ser Asn Phe
    210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
            275                 280                 285

Asn Gly Asp Val Val Ala Lys Ala Thr Tyr Asp Ile Leu Thr Lys Thr
        290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
        370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asp Gln Phe Lys Asn
        450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
                500                 505                 510

Thr Asn Arg Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn Pro Lys
        530                 535                 540

Asp Pro Thr Pro Gly Pro Val Asp Pro Glu Pro Ser Pro Asp Pro
545                 550                 555                 560

Glu Pro Glu Pro Thr Pro Asp Pro Glu Pro Ser Pro Asp Pro Glu Pro
                565                 570                 575

Glu Pro Ser Pro Asp Pro Asp Pro Asp Ser Asp Ser Asp Ser Asp Ser
                580                 585                 590

Gly Ser Asp Ser Asp Ser Gly Ser Asp Ser Asp Ser Glu Ser Asp Ser
            595                 600                 605

Asp Ser Asp Ser Asp Ser Asp Ser Asp Ser Asp Ser Asp Ser Glu Ser
        610                 615                 620
```

Asp Ser Asp Ser Glu Ser Asp Ser Glu Ser Asp Ser Asp Ser
625                 630                 635                 640

Asp Ser Asp Ser Asp Ser Asp Ser Asp Ser Asp Ser Asp Ser
            645                 650                 655

Asp Ser Asp Ser Asp Ser Asp Ser Asp Ser Asp Ser Asp Ser
            660                 665                 670

Asp Ser Asp Ser Asp Ser Asp Ser Asp Ser Asp Ser Asp Ser
            675                 680                 685

Asp Ser Asp Ser Asp Ser Asp Ser Asp Ser Asp Ser Asp Ser
        690                 695                 700

Asp Ser Asp Ser Asp Ser Asp Ser Asp Ser Asp Ser Asp Ser
705                 710                 715                 720

Asp Ser Asp Ser Asp Ser Asp Ser Asp Ser Asp Ser Asp Ser
            725                 730                 735

Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser
            755                 760                 765

Asp Ser Asp Ser Asp Ser Asp Ser Asp Ser Asp Ser Asp Ser
770                 775                 780

Asp Ser Asp Ser Asp Ser Asp Ser Asp Ser Asp Ser Asp Ser
785                 790                 795                 800

Asp Ser Asp Ser Arg Val Thr Pro Pro Asn Glu Gln Lys Ala Pro
                805                 810                 815

Ser Asn Pro Lys Gly Glu Val Asn His Ser Asn Lys Val Ser Lys Gln
            820                 825                 830

His Lys Thr Asp Ala Leu Pro Glu Thr Gly Asp Lys Ser Glu Asn Thr
            835                 840                 845

Asn Ala Thr Leu Phe Gly Ala Met Met Ala Leu Leu Gly Ser Leu Leu
        850                 855                 860

Leu Phe Arg Lys Arg Lys Gln Asp His Lys Glu Lys Ala
865                 870                 875

<210> SEQ ID NO 4
<211> LENGTH: 508
<212> TYPE: PRT
<213> ORGANISM: Staphylococcus aureus

<400> SEQUENCE: 4

Ser Glu Gln Ser Asn Asp Thr Thr Gln Ser Ser Lys Asn Asn Ala Ser
1               5                   10                  15

Ala Asp Ser Glu Lys Asn Asn Met Ile Glu Thr Pro Gln Leu Asn Thr
            20                  25                  30

Thr Ala Asn Asp Thr Ser Asp Ile Ser Ala Asn Thr Asn Ser Ala Asn
        35                  40                  45

Val Asp Ser Thr Thr Lys Pro Met Ser Thr Gln Thr Ser Asn Thr Thr
    50                  55                  60

Thr Thr Glu Pro Ala Ser Thr Asn Glu Thr Pro Gln Pro Thr Ala Ile
65                  70                  75                  80

Lys Asn Gln Ala Thr Ala Ala Lys Met Gln Asp Gln Thr Val Pro Gln
                85                  90                  95

Glu Ala Asn Ser Gln Val Asp Asn Lys Thr Thr Asn Asp Ala Asn Ser
            100                 105                 110

Ile Ala Thr Asn Ser Glu Leu Lys Asn Ser Gln Thr Leu Asp Leu Pro
        115                 120                 125

-continued

Gln Ser Ser Pro Gln Thr Ile Ser Asn Ala Gln Gly Thr Ser Lys Pro
        130                 135                 140

Ser Val Arg Thr Arg Ala Val Arg Ser Leu Ala Val Ala Glu Pro Val
145                 150                 155                 160

Val Asn Ala Ala Asp Ala Lys Gly Thr Asn Val Asn Asp Lys Val Thr
                165                 170                 175

Ala Ser Asn Phe Lys Leu Glu Lys Thr Thr Phe Asp Pro Asn Gln Ser
            180                 185                 190

Gly Asn Thr Phe Met Ala Ala Asn Phe Thr Val Thr Asp Lys Val Lys
        195                 200                 205

Ser Gly Asp Tyr Phe Thr Ala Lys Leu Pro Asp Ser Leu Thr Gly Asn
210                 215                 220

Gly Asp Val Asp Tyr Ser Asn Ser Asn Thr Met Pro Ile Ala Asp
225                 230                 235                 240

Ile Lys Ser Thr Asn Gly Asp Val Val Ala Lys Ala Thr Tyr Asp Ile
                245                 250                 255

Leu Thr Lys Thr Tyr Thr Phe Val Phe Thr Asp Tyr Val Asn Asn Lys
            260                 265                 270

Glu Asn Ile Asn Gly Gln Phe Ser Leu Pro Leu Phe Thr Asp Arg Ala
        275                 280                 285

Lys Ala Pro Lys Ser Gly Thr Tyr Asp Ala Asn Ile Asn Ile Ala Asp
290                 295                 300

Glu Met Phe Asn Asn Lys Ile Thr Tyr Asn Tyr Ser Ser Pro Ile Ala
305                 310                 315                 320

Gly Ile Asp Lys Pro Asn Gly Ala Asn Ile Ser Ser Gln Ile Ile Gly
                325                 330                 335

Val Asp Thr Ala Ser Gly Gln Asn Thr Tyr Lys Gln Thr Val Phe Val
            340                 345                 350

Asn Pro Lys Gln Arg Val Leu Gly Asn Thr Trp Val Tyr Ile Lys Gly
        355                 360                 365

Tyr Gln Asp Lys Ile Glu Glu Ser Ser Gly Lys Val Ser Ala Thr Asp
370                 375                 380

Thr Lys Leu Arg Ile Phe Glu Val Asn Asp Thr Ser Lys Leu Ser Asp
385                 390                 395                 400

Ser Tyr Tyr Ala Asp Pro Asn Asp Ser Asn Leu Lys Glu Val Thr Asp
                405                 410                 415

Gln Phe Lys Asn Arg Ile Tyr Tyr Glu His Pro Asn Val Ala Ser Ile
            420                 425                 430

Lys Phe Gly Asp Ile Thr Lys Thr Tyr Val Val Leu Val Glu Gly His
        435                 440                 445

Tyr Asp Asn Thr Gly Lys Asn Leu Lys Thr Gln Val Ile Gln Glu Asn
450                 455                 460

Val Asp Pro Val Thr Asn Arg Asp Tyr Ser Ile Phe Gly Trp Asn Asn
465                 470                 475                 480

Glu Asn Val Val Arg Tyr Gly Gly Gly Ser Ala Asp Gly Asp Ser Ala
                485                 490                 495

Val Asn Pro Lys Asp Pro Thr Pro Gly Pro Val
            500                 505

<210> SEQ ID NO 5
<211> LENGTH: 316
<212> TYPE: PRT
<213> ORGANISM: Staphylococcus aureus

<400> SEQUENCE: 5

Ser Glu Gln Ser Asn Asp Thr Thr Gln Ser Ser Lys Asn Asn Ala Ser
1               5                   10                  15

Ala Asp Ser Glu Lys Asn Asn Met Ile Glu Thr Pro Gln Leu Asn Thr
            20                  25                  30

Thr Ala Asn Asp Thr Ser Asp Ile Ser Ala Asn Thr Asn Ser Ala Asn
        35                  40                  45

Val Asp Ser Thr Thr Lys Pro Met Ser Thr Gln Thr Ser Asn Thr Thr
    50                  55                  60

Thr Thr Glu Pro Ala Ser Thr Asn Glu Thr Pro Gln Pro Thr Ala Ile
65                  70                  75                  80

Lys Asn Gln Ala Thr Ala Ala Lys Met Gln Asp Gln Thr Val Pro Gln
                85                  90                  95

Glu Ala Asn Ser Gln Val Asp Asn Lys Thr Thr Asn Asp Ala Asn Ser
            100                 105                 110

Ile Ala Thr Asn Ser Glu Leu Lys Asn Ser Gln Thr Leu Asp Leu Pro
        115                 120                 125

Gln Ser Ser Pro Gln Thr Ile Ser Asn Ala Gln Gly Thr Ser Lys Pro
    130                 135                 140

Ser Val Arg Thr Arg Ala Val Arg Ser Leu Ala Val Ala Glu Pro Val
145                 150                 155                 160

Val Asn Ala Ala Asp Ala Lys Gly Thr Asn Val Asn Asp Lys Val Thr
                165                 170                 175

Ala Ser Asn Phe Lys Leu Glu Lys Thr Thr Phe Asp Pro Asn Gln Ser
            180                 185                 190

Gly Asn Thr Phe Met Ala Ala Asn Phe Thr Val Thr Asp Lys Val Lys
        195                 200                 205

Ser Gly Asp Tyr Phe Thr Ala Lys Leu Pro Asp Ser Leu Thr Gly Asn
    210                 215                 220

Gly Asp Val Asp Tyr Ser Asn Ser Asn Thr Met Pro Ile Ala Asp
225                 230                 235                 240

Ile Lys Ser Thr Asn Gly Asp Val Val Ala Lys Ala Thr Tyr Asp Ile
                245                 250                 255

Leu Thr Lys Thr Tyr Thr Phe Val Phe Thr Asp Tyr Val Asn Asn Lys
            260                 265                 270

Glu Asn Ile Asn Gly Gln Phe Ser Leu Pro Leu Phe Thr Asp Arg Ala
        275                 280                 285

Lys Ala Pro Lys Ser Gly Thr Tyr Asp Ala Asn Ile Asn Ile Ala Asp
    290                 295                 300

Glu Met Phe Asn Asn Lys Ile Thr Tyr Asn Tyr Ser
305                 310                 315

<210> SEQ ID NO 6
<211> LENGTH: 331
<212> TYPE: PRT
<213> ORGANISM: Staphylococcus aureus

<400> SEQUENCE: 6

Gly Thr Asn Val Asn Asp Lys Val Thr Ala Ser Asn Phe Lys Leu Glu
1               5                   10                  15

Lys Thr Thr Phe Asp Pro Asn Gln Ser Gly Asn Thr Phe Met Ala Ala
            20                  25                  30

Asn Phe Thr Val Thr Asp Lys Val Lys Ser Gly Asp Tyr Phe Thr Ala
        35                  40                  45

```
Lys Leu Pro Asp Ser Leu Thr Gly Asn Gly Asp Val Asp Tyr Ser Asn
 50                  55                  60

Ser Asn Asn Thr Met Pro Ile Ala Asp Ile Lys Ser Thr Asn Gly Asp
 65                  70                  75                  80

Val Val Ala Lys Ala Thr Tyr Asp Ile Leu Thr Lys Thr Tyr Thr Phe
                 85                  90                  95

Val Phe Thr Asp Tyr Val Asn Asn Lys Glu Asn Ile Asn Gly Gln Phe
            100                 105                 110

Ser Leu Pro Leu Phe Thr Asp Arg Ala Lys Ala Pro Lys Ser Gly Thr
            115                 120                 125

Tyr Asp Ala Asn Ile Asn Ile Ala Asp Glu Met Phe Asn Asn Lys Ile
130                 135                 140

Thr Tyr Asn Tyr Ser Ser Pro Ile Ala Gly Ile Asp Lys Pro Asn Gly
145                 150                 155                 160

Ala Asn Ile Ser Ser Gln Ile Ile Gly Val Asp Thr Ala Ser Gly Gln
                165                 170                 175

Asn Thr Tyr Lys Gln Thr Val Phe Val Asn Pro Lys Gln Arg Val Leu
            180                 185                 190

Gly Asn Thr Trp Val Tyr Ile Lys Gly Tyr Gln Asp Lys Ile Glu Glu
        195                 200                 205

Ser Ser Gly Lys Val Ser Ala Thr Asp Thr Lys Leu Arg Ile Phe Glu
210                 215                 220

Val Asn Asp Thr Ser Lys Leu Ser Asp Ser Tyr Tyr Ala Asp Pro Asn
225                 230                 235                 240

Asp Ser Asn Leu Lys Glu Val Thr Asp Gln Phe Lys Asn Arg Ile Tyr
                245                 250                 255

Tyr Glu His Pro Asn Val Ala Ser Ile Lys Phe Gly Asp Ile Thr Lys
            260                 265                 270

Thr Tyr Val Val Leu Val Glu Gly His Tyr Asp Asn Thr Gly Lys Asn
        275                 280                 285

Leu Lys Thr Gln Val Ile Gln Glu Asn Val Asp Pro Val Thr Asn Arg
290                 295                 300

Asp Tyr Ser Ile Phe Gly Trp Asn Asn Glu Asn Val Val Arg Tyr Gly
305                 310                 315                 320

Gly Gly Ser Ala Asp Gly Asp Ser Ala Val Asn
                325                 330

<210> SEQ ID NO 7
<211> LENGTH: 183
<212> TYPE: PRT
<213> ORGANISM: Staphylococcus aureus

<400> SEQUENCE: 7

Ser Ser Pro Ile Ala Gly Ile Asp Lys Pro Asn Gly Ala Asn Ile Ser
 1               5                  10                  15

Ser Gln Ile Ile Gly Val Asp Thr Ala Ser Gly Gln Asn Thr Tyr Lys
             20                  25                  30

Gln Thr Val Phe Val Asn Pro Lys Gln Arg Val Leu Gly Asn Thr Trp
         35                  40                  45

Val Tyr Ile Lys Gly Tyr Gln Asp Lys Ile Glu Glu Ser Ser Gly Lys
 50                  55                  60

Val Ser Ala Thr Asp Thr Lys Leu Arg Ile Phe Glu Val Asn Asp Thr
 65                  70                  75                  80

Ser Lys Leu Ser Asp Ser Tyr Tyr Ala Asp Pro Asn Asp Ser Asn Leu
                 85                  90                  95
```

```
Lys Glu Val Thr Asp Gln Phe Lys Asn Arg Ile Tyr Tyr Glu His Pro
            100                 105                 110

Asn Val Ala Ser Ile Lys Phe Gly Asp Ile Thr Lys Thr Tyr Val Val
            115                 120                 125

Leu Val Glu Gly His Tyr Asp Asn Thr Gly Lys Asn Leu Lys Thr Gln
        130                 135                 140

Val Ile Gln Glu Asn Val Asp Pro Val Thr Asn Arg Asp Tyr Ser Ile
145                 150                 155                 160

Phe Gly Trp Asn Asn Glu Asn Val Val Arg Tyr Gly Gly Gly Ser Ala
                165                 170                 175

Asp Gly Asp Ser Ala Val Asn
            180

<210> SEQ ID NO 8
<211> LENGTH: 1166
<212> TYPE: PRT
<213> ORGANISM: Staphylococcus aureus

<400> SEQUENCE: 8

Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Asn Thr Ser Thr Glu Asn Ala Lys Gln Asp
    50                  55                  60

Asp Ala Thr Thr Ser Asp Asn Lys Glu Val Val Ser Glu Thr Glu Asn
65                  70                  75                  80

Asn Ser Thr Thr Glu Asn Asn Ser Thr Asn Pro Ile Lys Lys Glu Thr
                85                  90                  95

Asn Thr Asp Ser Gln Pro Glu Ala Lys Lys Glu Ser Thr Ser Ser Ser
            100                 105                 110

Thr Gln Lys Gln Gln Asn Asn Val Thr Ala Thr Thr Glu Thr Lys Pro
        115                 120                 125

Gln Asn Ile Glu Lys Glu Asn Val Lys Pro Ser Thr Asp Lys Thr Ala
    130                 135                 140

Thr Glu Asp Thr Ser Val Ile Leu Glu Glu Lys Lys Ala Pro Asn Asn
145                 150                 155                 160

Thr Asn Asn Asp Val Thr Thr Lys Pro Ser Thr Ser Glu Pro Ser Thr
                165                 170                 175

Ser Glu Ile Gln Thr Lys Pro Thr Thr Pro Gln Glu Ser Thr Asn Ile
            180                 185                 190

Glu Asn Ser Gln Pro Gln Pro Thr Pro Ser Lys Val Asp Asn Gln Val
        195                 200                 205

Thr Asp Ala Thr Asn Pro Lys Glu Pro Val Asn Val Ser Lys Glu Glu
    210                 215                 220

Leu Lys Asn Asn Pro Glu Lys Leu Lys Glu Leu Val Arg Asn Asp Ser
225                 230                 235                 240

Asn Thr Asp His Ser Thr Lys Pro Val Ala Thr Ala Pro Thr Ser Val
                245                 250                 255

Ala Pro Lys Arg Val Asn Ala Lys Met Arg Phe Ala Val Ala Gln Pro
            260                 265                 270

Ala Ala Val Ala Ser Asn Asn Val Asn Asp Leu Ile Lys Val Thr Lys
```

|     |     |     | 275 |     |     |     | 280 |     |     |     | 285 |     |     |
|---|---|---|---|---|---|---|---|---|---|---|---|---|---|

Gln Thr Ile Lys Val Gly Asp Gly Lys Asp Asn Val Ala Ala Ala His
290                 295                 300

Asp Gly Lys Asp Ile Glu Tyr Asp Thr Glu Phe Thr Ile Asp Asn Lys
305                 310                 315                 320

Val Lys Lys Gly Asp Thr Met Thr Ile Asn Tyr Asp Lys Asn Val Ile
                325                 330                 335

Pro Ser Asp Leu Thr Asp Lys Asn Asp Pro Ile Asp Ile Thr Asp Pro
                340                 345                 350

Ser Gly Glu Val Ile Ala Lys Gly Thr Phe Asp Lys Ala Thr Lys Gln
                355                 360                 365

Ile Thr Tyr Thr Phe Thr Asp Tyr Val Asp Lys Tyr Glu Asp Ile Lys
370                 375                 380

Ser Arg Leu Thr Leu Tyr Ser Tyr Ile Asp Lys Lys Thr Val Pro Asn
385                 390                 395                 400

Glu Thr Ser Leu Asn Leu Thr Phe Ala Thr Ala Gly Lys Glu Thr Ser
                405                 410                 415

Gln Asn Val Thr Val Asp Tyr Gln Asp Pro Met Val His Gly Asp Ser
                420                 425                 430

Asn Ile Gln Ser Ile Phe Thr Lys Leu Asp Glu Asp Lys Gln Thr Ile
                435                 440                 445

Glu Gln Gln Ile Tyr Val Asn Pro Leu Lys Lys Ser Ala Thr Asn Thr
450                 455                 460

Lys Val Asp Ile Ala Gly Ser Gln Val Asp Asp Tyr Gly Asn Ile Lys
465                 470                 475                 480

Leu Gly Asn Gly Ser Thr Ile Ile Asp Gln Asn Thr Glu Ile Lys Val
                485                 490                 495

Tyr Lys Val Asn Ser Asp Gln Gln Leu Pro Gln Ser Asn Arg Ile Tyr
                500                 505                 510

Asp Phe Ser Gln Tyr Glu Asp Val Thr Ser Gln Phe Asp Asn Lys Lys
                515                 520                 525

Ser Phe Ser Asn Asn Val Ala Thr Leu Asp Phe Gly Asp Ile Asn Ser
530                 535                 540

Ala Tyr Ile Ile Lys Val Val Ser Lys Tyr Thr Pro Thr Ser Asp Gly
545                 550                 555                 560

Glu Leu Asp Ile Ala Gln Gly Thr Ser Met Arg Thr Thr Asp Lys Tyr
                565                 570                 575

Gly Tyr Tyr Asn Tyr Ala Gly Tyr Ser Asn Phe Ile Val Thr Ser Asn
                580                 585                 590

Asp Thr Gly Gly Asp Gly Thr Val Lys Pro Glu Glu Lys Leu Tyr
                595                 600                 605

Lys Ile Gly Asp Tyr Val Trp Glu Asp Val Asp Lys Asp Gly Val Gln
610                 615                 620

Gly Thr Asp Ser Lys Glu Lys Pro Met Ala Asn Val Leu Val Thr Leu
625                 630                 635                 640

Thr Tyr Pro Asp Gly Thr Thr Lys Ser Val Arg Thr Asp Ala Asn Gly
                645                 650                 655

His Tyr Glu Phe Gly Gly Leu Lys Asp Gly Glu Thr Tyr Thr Val Lys
                660                 665                 670

Phe Glu Thr Pro Thr Gly Tyr Leu Pro Thr Lys Val Asn Gly Thr Thr
                675                 680                 685

Asp Gly Glu Lys Asp Ser Asn Gly Ser Ser Val Thr Val Lys Ile Asn
690                 695                 700

-continued

Gly Lys Asp Asp Met Ser Leu Asp Thr Gly Phe Tyr Lys Glu Pro Lys
705                 710                 715                 720

Tyr Asn Leu Gly Asp Tyr Val Trp Glu Asp Thr Asn Lys Asp Gly Ile
            725                 730                 735

Gln Asp Ala Asn Glu Pro Gly Ile Lys Asp Val Lys Val Thr Leu Lys
        740                 745                 750

Asp Ser Thr Gly Lys Val Ile Gly Thr Thr Thr Asp Ala Ser Gly
        755                 760                 765

Lys Tyr Lys Phe Thr Asp Leu Asp Asn Gly Asn Tyr Thr Val Glu Phe
        770                 775                 780

Glu Thr Pro Ala Gly Tyr Thr Pro Thr Val Lys Asn Thr Thr Ala Asp
785                 790                 795                 800

Asp Lys Asp Ser Asn Gly Leu Thr Thr Thr Gly Val Ile Lys Asp Ala
            805                 810                 815

Asp Asn Met Thr Leu Asp Arg Gly Phe Tyr Lys Thr Pro Lys Tyr Ser
        820                 825                 830

Leu Gly Asp Tyr Val Trp Tyr Asp Ser Asn Lys Asp Gly Lys Gln Asp
        835                 840                 845

Ser Thr Glu Lys Gly Ile Lys Asp Val Thr Val Thr Leu Gln Asn Glu
    850                 855                 860

Lys Gly Glu Val Ile Gly Thr Thr Lys Thr Asp Glu Asn Gly Lys Tyr
865                 870                 875                 880

Arg Phe Asp Asn Leu Asp Ser Gly Lys Tyr Lys Val Ile Phe Glu Lys
            885                 890                 895

Pro Ala Gly Leu Thr Gln Thr Val Asn Thr Thr Glu Asp Asp Lys
        900                 905                 910

Asp Ala Asp Gly Gly Glu Val Asp Val Thr Ile Thr Asp His Asp Asp
        915                 920                 925

Phe Thr Leu Asp Asn Gly Tyr Phe Glu Glu Thr Ser Asp Ser Asp
        930                 935                 940

Ser Asp Ser Asp Ser Asp Ser Asp Ser Asp Ser Asp Ser Asp Ser Asp
945                 950                 955                 960

Ser Asp Ser Asp Ser Asp Ser Asp Ser Asp Ser Asp Ser Asp Ser Asp
            965                 970                 975

Ser Asp Ser Asp Ser Asp Ser Asp Ser Asp Ser Asp Ser Asp Ser Asp
        980                 985                 990

Ser Asp Ser Asp Ser Asp Ser Asp Ser Asp Ser Asp Ser Asp Ser Asp
        995                 1000                1005

Ser Asp Ser Asp Ser Asp Ser Asp Ser Asp Ser Asp Ser Asp Ser Asp
    1010                1015                1020

Ser Asp Ser Asp Ser Asp Ser Asp Ser Asp Ser Asp Ser Asp Ser Asp
1025                1030                1035                1040

Ser Asp Ser Asp Ser Asp Ser Asp Ser Asp Ser Asp Ser Asp Ser Asp
            1045                1050                1055

Ser Asp Ser Asp Ser Asp Ser Asp Ser Asp Ser Asp Ser Asp Ser Asp
        1060                1065                1070

Ser Asp Ser Asp Ser Asp Ser Asp Ser Asp Ser Asp Ser Asp Ser Asp
        1075                1080                1085

Ser Asp Ser Asp Ser Asp Ser Asp Ser Asp Ser Asp Ser Asp Ser Asp
        1090                1095                1100

Ser Asp Ala Gly Lys His Thr Pro Val Lys Pro Met Ser Thr Thr Lys
1105                1110                1115                1120

-continued

Asp His His Asn Lys Ala Lys Ala Leu Pro Glu Thr Gly Ser Glu Asn
              1125                1130                1135

Asn Gly Ser Asn Asn Ala Thr Leu Phe Gly Gly Leu Phe Ala Ala Leu
              1140                1145                1150

Gly Ser Leu Leu Leu Phe Gly Arg Arg Lys Lys Gln Asn Lys
         1155                1160                1165

<210> SEQ ID NO 9
<211> LENGTH: 580
<212> TYPE: PRT
<213> ORGANISM: Staphylococcus aureus

<400> SEQUENCE: 9

Ala Glu Asn Thr Ser Thr Glu Asn Ala Lys Gln Asp Asp Ala Thr Thr
1               5                   10                  15

Ser Asp Asn Lys Glu Val Val Ser Glu Thr Glu Asn Asn Ser Thr Thr
            20                  25                  30

Glu Asn Asn Ser Thr Asn Pro Ile Lys Lys Glu Thr Asn Thr Asp Ser
        35                  40                  45

Gln Pro Glu Ala Lys Lys Glu Ser Thr Ser Ser Thr Gln Lys Gln
    50                  55                  60

Gln Asn Asn Val Thr Ala Thr Thr Glu Thr Lys Pro Gln Asn Ile Glu
65                  70                  75                  80

Lys Glu Asn Val Lys Pro Ser Thr Asp Lys Thr Ala Thr Glu Asp Thr
                85                  90                  95

Ser Val Ile Leu Glu Glu Lys Lys Ala Pro Asn Asn Thr Asn Asn Asp
            100                 105                 110

Val Thr Thr Lys Pro Ser Thr Ser Glu Pro Ser Thr Ser Glu Ile Gln
        115                 120                 125

Thr Lys Pro Thr Thr Pro Gln Glu Ser Thr Asn Ile Glu Asn Ser Gln
    130                 135                 140

Pro Gln Pro Thr Pro Ser Lys Val Asp Asn Gln Val Thr Asp Ala Thr
145                 150                 155                 160

Asn Pro Lys Glu Pro Val Asn Val Ser Lys Glu Glu Leu Lys Asn Asn
                165                 170                 175

Pro Glu Lys Leu Lys Glu Leu Val Arg Asn Asp Ser Asn Thr Asp His
            180                 185                 190

Ser Thr Lys Pro Val Ala Thr Ala Pro Thr Ser Val Ala Pro Lys Arg
        195                 200                 205

Val Asn Ala Lys Met Arg Phe Ala Val Ala Gln Pro Ala Ala Val Ala
    210                 215                 220

Ser Asn Asn Val Asn Asp Leu Ile Lys Val Thr Lys Gln Thr Ile Lys
225                 230                 235                 240

Val Gly Asp Gly Lys Asp Asn Val Ala Ala His Asp Gly Lys Asp
                245                 250                 255

Ile Glu Tyr Asp Thr Glu Phe Thr Ile Asp Asn Lys Val Lys Lys Gly
            260                 265                 270

Asp Thr Met Thr Ile Asn Tyr Asp Lys Asn Val Ile Pro Ser Asp Leu
        275                 280                 285

Thr Asp Lys Asn Asp Pro Ile Asp Ile Thr Asp Pro Ser Gly Glu Val
    290                 295                 300

Ile Ala Lys Gly Thr Phe Asp Lys Ala Thr Lys Gln Ile Thr Tyr Thr
305                 310                 315                 320

Phe Thr Asp Tyr Val Asp Lys Tyr Glu Asp Ile Lys Ser Arg Leu Thr
                325                 330                 335

Leu Tyr Ser Tyr Ile Asp Lys Lys Thr Val Pro Asn Glu Thr Ser Leu
              340                 345                 350

Asn Leu Thr Phe Ala Thr Ala Gly Lys Glu Thr Ser Gln Asn Val Thr
              355                 360                 365

Val Asp Tyr Gln Asp Pro Met Val His Gly Asp Ser Asn Ile Gln Ser
370                 375                 380

Ile Phe Thr Lys Leu Asp Glu Asp Lys Gln Thr Ile Glu Gln Gln Ile
385                 390                 395                 400

Tyr Val Asn Pro Leu Lys Lys Ser Ala Thr Asn Thr Lys Val Asp Ile
              405                 410                 415

Ala Gly Ser Gln Val Asp Asp Tyr Gly Asn Ile Lys Leu Gly Asn Gly
              420                 425                 430

Ser Thr Ile Ile Asp Gln Asn Thr Glu Ile Lys Val Tyr Lys Val Asn
              435                 440                 445

Ser Asp Gln Gln Leu Pro Gln Ser Asn Arg Ile Tyr Asp Phe Ser Gln
              450                 455                 460

Tyr Glu Asp Val Thr Ser Gln Phe Asp Asn Lys Lys Ser Phe Ser Asn
465                 470                 475                 480

Asn Val Ala Thr Leu Asp Phe Gly Asp Ile Asn Ser Ala Tyr Ile Ile
              485                 490                 495

Lys Val Val Ser Lys Tyr Thr Pro Thr Ser Asp Gly Glu Leu Asp Ile
              500                 505                 510

Ala Gln Gly Thr Ser Met Arg Thr Thr Asp Lys Tyr Gly Tyr Tyr Asn
              515                 520                 525

Tyr Ala Gly Tyr Ser Asn Phe Ile Val Thr Ser Asn Asp Thr Gly Gly
              530                 535                 540

Gly Asp Gly Thr Val Lys Pro Glu Glu Lys Leu Tyr Lys Ile Gly Asp
545                 550                 555                 560

Tyr Val Trp Glu Asp Val Asp Lys Asp Gly Val Gln Gly Thr Asp Ser
              565                 570                 575

Lys Glu Lys Pro
              580

<210> SEQ ID NO 10
<211> LENGTH: 995
<212> TYPE: PRT
<213> ORGANISM: Staphylococcus aureus

<400> SEQUENCE: 10

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
              20                  25                  30

Ile Leu Val Gly Thr Thr Leu Ile Phe Gly Leu Ser Gly His Glu Ala
              35                  40                  45

Lys Ala Ala Glu His Thr Asn Gly Glu Leu Asn Gln Ser Lys Asn Glu
        50                  55                  60

Thr Thr Ala Pro Ser Glu Asn Lys Thr Lys Lys Val Asp Ser Arg
65                  70                  75                  80

Gln Leu Lys Asp Asn Thr Gln Thr Ala Thr Ala Asp Gln Pro Lys Val
              85                  90                  95

Thr Met Ser Asp Ser Ala Thr Val Lys Glu Thr Ser Ser Asn Met Gln
              100                 105                 110

Ser Pro Gln Asn Ala Thr Ala Asn Gln Ser Thr Thr Lys Thr Ser Asn

-continued

```
            115                 120                 125
Val Thr Thr Asn Asp Lys Ser Ser Thr Thr Tyr Ser Asn Glu Thr Asp
130                 135                 140

Lys Ser Asn Leu Thr Gln Ala Lys Asp Val Ser Thr Pro Lys Thr
145                 150                 155                 160

Thr Thr Ile Lys Pro Arg Thr Leu Asn Arg Met Ala Val Asn Thr Val
                165                 170                 175

Ala Ala Pro Gln Gln Gly Thr Asn Val Asn Asp Lys Val His Phe Ser
            180                 185                 190

Asn Ile Asp Ile Ala Ile Asp Lys Gly His Val Asn Gln Thr Thr Gly
        195                 200                 205

Lys Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Thr Thr Asn Thr Thr Tyr Thr Phe Thr Asn Tyr Val
        275                 280                 285

Asp Gln Tyr Thr Asn Val Arg Gly Ser Phe Glu Gln Val Ala Phe Ala
    290                 295                 300

Lys Arg Lys Asn Ala Thr Thr Asp Lys Thr Ala Tyr Lys Met Glu Val
305                 310                 315                 320

Thr Leu Gly Asn Asp Thr Tyr Ser Glu Glu Ile Ile Val Asp Tyr Gly
                325                 330                 335

Asn Lys Lys Ala Gln Pro Leu Ile Ser Ser Thr Asn Tyr Ile Asn Asn
            340                 345                 350

Glu Asp Leu Ser Arg Asn Met Thr Ala Tyr Val Asn Gln Pro Lys Asn
        355                 360                 365

Thr Tyr Thr Lys Gln Thr Phe Val Thr Asn Leu Thr Gly Tyr Lys Phe
    370                 375                 380

Asn Pro Asn Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Asp Gln Phe Asp Val Ile Tyr Ser Asn Asp Asn Lys Thr Ala Thr
            420                 425                 430

Val Asp Leu Met Lys Gly Gln Thr Ser Ser Asn Lys Gln Tyr Ile Ile
        435                 440                 445

Gln Gln Val Ala Tyr Pro Asp Asn Ser Ser Thr Asp Asn Gly Lys Ile
    450                 455                 460

Asp Tyr Thr Leu Asp Thr Asp Lys Thr Lys Tyr Ser Trp Ser Asn Ser
465                 470                 475                 480

Tyr Ser Asn Val Asn Gly Ser Ser Thr Ala Asn Gly Asp Gln Lys Lys
                485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
        515                 520                 525

Asp Ser Asn Gly Lys Glu Leu Asp Arg Thr Thr Thr Asp Glu Asn Gly
    530                 535                 540
```

| | | | | | | | | | | | | | | |
|---|---|---|---|---|---|---|---|---|---|---|---|---|---|---|
|Lys|Tyr|Gln|Phe|Thr|Gly|Leu|Ser|Asn|Gly|Thr|Tyr|Ser|Val|Glu|Phe|
|545| | | | |550| | | | |555| | | | |560|

Ser Thr Pro Ala Gly Tyr Thr Pro Thr Thr Ala Asn Val Gly Thr Asp
               565               570               575

Asp Ala Val Asp Ser Asp Gly Leu Thr Thr Gly Val Ile Lys Asp
580                 585                 590

Ala Asp Asn Met Thr Leu Asp Ser Gly Phe Tyr Lys Thr Pro Lys Tyr
        595                 600                 605

Ser Leu Gly Asp Tyr Val Trp Tyr Asp Ser Asn Lys Asp Gly Lys Gln
610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
        675                 680                 685

Lys Asp Ala Asp Gly Gly Glu Val Asp Val Thr Ile Thr Asp His Asp
690                 695                 700

Asp Phe Thr Leu Asp Asn Gly Tyr Tyr Glu Glu Thr Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
        755                 760                 765

Asp Ser Asp Ser Asp Ser Asp Ser Asp Ser Asp Ser Asp Ser Asp Ser
    770                 775                 780

Asp Ser Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser Asp Ser
                805                 810                 815

Asp Ser Asp Ser Asp Ser Asp Ser Asp Ser Asp Ser Asp Ser Asp Ser
            820                 825                 830

Asp Ser Asp Ser Asp Ser Asp Ser Asp Ser Asp Ser Asp Ser Asp Ser
        835                 840                 845

Asp Ser Asp Ser Asp Ser Asp Ser Asp Asn Asp Ser Asp Ser Asp Ser
    850                 855                 860

Asp Ser Asp Ser Asp Ser Asp Ser Asp Ser Asp Ser Asp Ser Asp Ser
865                 870                 875                 880

Asp Ser Asp Ser Asp Ser Asp Ser Asp Ser Asp Ser Asp Ser Asp Ser
                885                 890                 895

Asp Ser Asp Ser Asp Ser Asp Ser Asp Ser Asp Ser Asp Ser Asp Ser
            900                 905                 910

Asp Ser Asp Ser Asp Ser Asp Ser Asp Ser Asp Asn Asp Ser Asp Ser
        915                 920                 925

Asp Ser Asp Ser Asp Ser Asp Ala Gly Lys His Thr Pro Ala Lys Pro
    930                 935                 940

Met Ser Thr Val Lys Asp Gln His Lys Thr Ala Lys Ala Leu Pro Glu
945                 950                 955                 960

```
Thr Gly Ser Glu Asn Asn Ser Asn Asn Gly Thr Leu Phe Gly Gly
                965                 970                 975

Leu Phe Ala Ala Leu Gly Ser Leu Leu Leu Phe Gly Arg Arg Lys Lys
        980                 985                 990

Gln Asn Lys
        995

<210> SEQ ID NO 11
<211> LENGTH: 468
<212> TYPE: PRT
<213> ORGANISM: Staphylococcus aureus

<400> SEQUENCE: 11

Ala Glu His Thr Asn Gly Glu Leu Asn Gln Ser Lys Asn Glu Thr Thr
  1               5                  10                  15

Ala Pro Ser Glu Asn Lys Thr Thr Lys Val Asp Ser Arg Gln Leu
             20                  25                  30

Lys Asp Asn Thr Gln Thr Ala Thr Ala Asp Gln Pro Lys Val Thr Met
             35                  40                  45

Ser Asp Ser Ala Thr Val Lys Glu Thr Ser Ser Asn Met Gln Ser Pro
 50                  55                  60

Gln Asn Ala Thr Ala Asn Gln Ser Thr Thr Lys Thr Ser Asn Val Thr
 65                  70                  75                  80

Thr Asn Asp Lys Ser Ser Thr Thr Tyr Ser Asn Glu Thr Asp Lys Ser
                 85                  90                  95

Asn Leu Thr Gln Ala Lys Asp Val Ser Thr Thr Pro Lys Thr Thr Thr
            100                 105                 110

Ile Lys Pro Arg Thr Leu Asn Arg Met Ala Val Asn Thr Val Ala Ala
            115                 120                 125

Pro Gln Gln Gly Thr Asn Val Asn Asp Lys Val His Phe Ser Asn Ile
        130                 135                 140

Asp Ile Ala Ile Asp Lys Gly His Val Asn Gln Thr Thr Gly Lys Thr
145                 150                 155                 160

Glu Phe Trp Ala Thr Ser Ser Asp Val Leu Lys Leu Lys Ala Asn Tyr
                165                 170                 175

Thr Ile Asp Asp Ser Val Lys Glu Gly Asp Thr Phe Thr Phe Lys Tyr
            180                 185                 190

Gly Gln Tyr Phe Arg Pro Gly Ser Val Arg Leu Pro Ser Gln Thr Gln
        195                 200                 205

Asn Leu Tyr Asn Ala Gln Gly Asn Ile Ile Ala Lys Gly Ile Tyr Asp
    210                 215                 220

Ser Thr Thr Asn Thr Thr Thr Tyr Thr Phe Thr Asn Tyr Val Asp Gln
225                 230                 235                 240

Tyr Thr Asn Val Arg Gly Ser Phe Glu Gln Val Ala Phe Ala Lys Arg
                245                 250                 255

Lys Asn Ala Thr Thr Asp Lys Thr Ala Tyr Lys Met Glu Val Thr Leu
            260                 265                 270

Gly Asn Asp Thr Tyr Ser Glu Glu Ile Ile Val Asp Tyr Gly Asn Lys
        275                 280                 285

Lys Ala Gln Pro Leu Ile Ser Ser Thr Asn Tyr Ile Asn Asn Glu Asp
    290                 295                 300

Leu Ser Arg Asn Met Thr Ala Tyr Val Asn Gln Pro Lys Asn Thr Tyr
305                 310                 315                 320

Thr Lys Gln Thr Phe Val Thr Asn Leu Thr Gly Tyr Lys Phe Asn Pro
                325                 330                 335
```

Asn Ala Lys Asn Phe Lys Ile Tyr Glu Val Thr Asp Gln Asn Gln Phe
          340                 345                 350

Val Asp Ser Phe Thr Pro Asp Ser Lys Leu Lys Asp Val Thr Asp
          355                 360                 365

Gln Phe Asp Val Ile Tyr Ser Asn Asp Asn Lys Thr Ala Thr Val Asp
370                 375                 380

Leu Met Lys Gly Gln Thr Ser Ser Asn Lys Gln Tyr Ile Ile Gln Gln
385                 390                 395                 400

Val Ala Tyr Pro Asp Asn Ser Ser Thr Asp Asn Gly Lys Ile Asp Tyr
              405                 410                 415

Thr Leu Asp Thr Asp Lys Thr Lys Tyr Ser Trp Ser Asn Ser Tyr Ser
          420                 425                 430

Asn Val Asn Gly Ser Ser Thr Ala Asn Gly Asp Gln Lys Lys Tyr Asn
          435                 440                 445

Leu Gly Asp Tyr Val Trp Glu Asp Thr Asn Lys Asp Gly Lys Gln Asp
      450                 455                 460

Ala Asn Glu Lys
465

<210> SEQ ID NO 12
<211> LENGTH: 635
<212> TYPE: PRT
<213> ORGANISM: Staphylococcus aureus

<400> SEQUENCE: 12

Met Ala Lys Tyr Arg Gly Lys Pro Phe Gln Leu Tyr Val Lys Leu Ser
  1               5                  10                  15

Cys Ser Thr Met Met Ala Thr Ser Ile Ile Leu Thr Asn Ile Leu Pro
              20                  25                  30

Tyr Asp Ala Gln Ala Ala Ser Glu Lys Asp Thr Glu Ile Thr Lys Glu
          35                  40                  45

Ile Leu Ser Lys Gln Asp Leu Leu Asp Lys Val Asp Lys Ala Ile Arg
      50                  55                  60

Gln Ile Glu Gln Leu Lys Gln Leu Ser Ala Ser Ser Lys Glu His Tyr
65                  70                  75                  80

Lys Ala Gln Leu Asn Glu Ala Lys Thr Ala Ser Gln Ile Asp Glu Ile
              85                  90                  95

Ile Lys Arg Ala Asn Glu Leu Asp Ser Lys Asp Asn Lys Ser Ser His
          100                 105                 110

Thr Glu Met Asn Gly Gln Ser Asp Ile Asp Ser Lys Leu Asp Gln Leu
      115                 120                 125

Leu Lys Asp Leu Asn Glu Val Ser Ser Asn Val Asp Arg Gly Gln Gln
130                 135                 140

Ser Gly Glu Asp Asp Leu Asn Ala Met Lys Asn Asp Met Ser Gln Thr
145                 150                 155                 160

Ala Thr Thr Lys His Gly Glu Lys Asp Lys Asn Asp Glu Ala Met
              165                 170                 175

Val Asn Lys Ala Leu Glu Asp Leu Asp His Leu Asn Gln Gln Ile His
          180                 185                 190

Lys Ser Lys Asp Ala Ser Lys Asp Thr Ser Glu Asp Pro Ala Val Ser
      195                 200                 205

Thr Thr Asp Asn Asn His Glu Val Ala Lys Thr Pro Asn Asn Asp Gly
210                 215                 220

Ser Gly His Val Val Leu Asn Lys Phe Leu Ser Asn Glu Glu Asn Gln

```
            225                 230                 235                 240
        Ser His Ser Asn Arg Leu Thr Asp Lys Leu Gln Gly Ser Asp Lys Ile
                            245                 250                 255
        Asn His Ala Met Ile Glu Lys Leu Ala Lys Ser Asn Ala Ser Thr Gln
                            260                 265                 270
        His Tyr Thr Tyr His Lys Leu Asn Thr Leu Gln Ser Leu Asp Gln Arg
                            275                 280                 285
        Ile Ala Asn Thr Gln Leu Pro Lys Asn Gln Lys Ser Asp Leu Met Ser
                290                 295                 300
        Glu Val Asn Lys Thr Lys Glu Arg Ile Lys Ser Gln Arg Asn Ile Ile
        305                 310                 315                 320
        Leu Glu Glu Leu Ala Arg Thr Asp Asp Lys Lys Tyr Ala Thr Gln Ser
                            325                 330                 335
        Ile Leu Glu Ser Ile Phe Asn Lys Asp Glu Ala Val Lys Ile Leu Lys
                            340                 345                 350
        Asp Ile Arg Val Asp Gly Lys Thr Asp Gln Gln Ile Ala Asp Gln Ile
                            355                 360                 365
        Thr Arg His Ile Asp Gln Leu Ser Leu Thr Thr Ser Asp Asp Leu Leu
                370                 375                 380
        Thr Ser Leu Ile Asp Gln Ser Gln Asp Lys Ser Leu Leu Ile Ser Gln
        385                 390                 395                 400
        Ile Leu Gln Thr Lys Leu Gly Lys Ala Glu Ala Asp Lys Leu Ala Lys
                            405                 410                 415
        Asp Trp Thr Asn Lys Gly Leu Ser Asn Arg Gln Ile Val Asp Gln Leu
                            420                 425                 430
        Lys Lys His Phe Ala Ser Thr Gly Asp Thr Ser Ser Asp Asp Ile Leu
                            435                 440                 445
        Lys Ala Ile Leu Asn Asn Ala Lys Asp Lys Lys Gln Ala Ile Glu Thr
                450                 455                 460
        Ile Leu Ala Thr Arg Ile Glu Arg Gln Lys Ala Lys Leu Leu Ala Asp
        465                 470                 475                 480
        Leu Ile Thr Lys Ile Glu Thr Asp Gln Asn Lys Ile Phe Asn Leu Val
                            485                 490                 495
        Lys Ser Ala Leu Asn Gly Lys Ala Asp Asp Leu Leu Asn Leu Gln Lys
                            500                 505                 510
        Arg Leu Asn Gln Thr Lys Lys Asp Ile Asp Tyr Ile Leu Ser Pro Ile
                            515                 520                 525
        Val Asn Arg Pro Ser Leu Leu Asp Arg Leu Asn Lys Asn Gly Lys Thr
                530                 535                 540
        Thr Asp Leu Asn Lys Leu Ala Asn Leu Met Asn Gln Gly Ser Asp Leu
        545                 550                 555                 560
        Leu Asp Ser Ile Pro Asp Ile Pro Thr Pro Lys Pro Glu Lys Thr Leu
                            565                 570                 575
        Thr Leu Gly Lys Gly Asn Gly Leu Leu Ser Gly Leu Leu Asn Ala Asp
                            580                 585                 590
        Gly Asn Val Ser Leu Pro Lys Ala Gly Glu Thr Ile Lys Glu His Trp
                            595                 600                 605
        Leu Pro Ile Ser Val Ile Gly Ala Met Gly Val Leu Met Ile Trp
                    610                 615                 620
        Leu Ser Arg Arg Asn Lys Leu Lys Asn Lys Ala
        625                 630                 635

<210> SEQ ID NO 13
```

<211> LENGTH: 340
<212> TYPE: PRT
<213> ORGANISM: Staphylococcus aureus

<400> SEQUENCE: 13

Met Lys Lys Lys Leu Leu Val Leu Thr Met Ser Thr Leu Phe Ala Thr
1               5                   10                  15

Gln Ile Met Asn Ser Asn His Ala Lys Ala Ser Val Thr Glu Ser Val
            20                  25                  30

Asp Lys Lys Phe Val Val Pro Glu Ser Gly Ile Asn Lys Ile Ile Pro
        35                  40                  45

Ala Tyr Asp Glu Phe Lys Asn Ser Pro Lys Val Asn Val Ser Asn Leu
    50                  55                  60

Thr Asp Asn Lys Asn Phe Val Ala Ser Glu Asp Lys Leu Asn Lys Ile
65                  70                  75                  80

Ala Asp Ser Ser Ala Ala Ser Lys Ile Val Asp Lys Asn Phe Val Val
                85                  90                  95

Pro Glu Ser Lys Leu Gly Asn Ile Val Pro Glu Tyr Lys Glu Ile Asn
            100                 105                 110

Asn Arg Val Asn Val Ala Thr Asn Asn Pro Ala Ser Gln Gln Val Asp
        115                 120                 125

Lys His Phe Val Ala Lys Gly Pro Glu Val Asn Arg Phe Ile Thr Gln
    130                 135                 140

Asn Lys Val Asn His His Phe Ile Thr Thr Gln Thr His Tyr Lys Lys
145                 150                 155                 160

Val Ile Thr Ser Tyr Lys Ser Thr His Val His Lys His Val Asn His
                165                 170                 175

Ala Lys Asp Ser Ile Asn Lys His Phe Ile Val Lys Pro Ser Glu Ser
            180                 185                 190

Pro Arg Tyr Thr His Pro Ser Gln Ser Leu Ile Ile Lys His His Phe
        195                 200                 205

Ala Val Pro Gly Tyr His Ala His Lys Phe Val Thr Pro Gly His Ala
    210                 215                 220

Ser Ile Lys Ile Asn His Phe Cys Val Val Pro Gln Ile Asn Ser Phe
225                 230                 235                 240

Lys Val Ile Pro Pro Tyr Gly His Asn Ser His Arg Met His Val Pro
                245                 250                 255

Ser Phe Gln Asn Asn Thr Thr Ala Thr His Gln Asn Ala Lys Val Asn
            260                 265                 270

Lys Ala Tyr Asp Tyr Lys Tyr Phe Tyr Ser Tyr Lys Val Val Lys Gly
        275                 280                 285

Val Lys Lys Tyr Phe Ser Phe Ser Gln Ser Asn Gly Tyr Lys Ile Gly
    290                 295                 300

Lys Pro Ser Leu Asn Ile Lys Asn Val Asn Tyr Gln Tyr Ala Val Pro
305                 310                 315                 320

Ser Tyr Ser Pro Thr His Tyr Val Pro Glu Phe Lys Gly Ser Leu Pro
                325                 330                 335

Ala Pro Arg Val
            340

<210> SEQ ID NO 14
<211> LENGTH: 306
<212> TYPE: PRT
<213> ORGANISM: Staphylococcus aureus

<400> SEQUENCE: 14

Lys Phe Val Val Pro Glu Ser Gly Ile Asn Lys Ile Pro Ala Tyr
1               5                   10                  15

Asp Glu Phe Lys Asn Ser Pro Lys Val Asn Val Ser Asn Leu Thr Asp
            20                  25                  30

Asn Lys Asn Phe Val Ala Ser Glu Asp Lys Leu Asn Lys Ile Ala Asp
        35                  40                  45

Ser Ser Ala Ala Ser Lys Ile Val Asp Lys Asn Phe Val Pro Glu
50                  55                      60

Ser Lys Leu Gly Asn Ile Val Pro Glu Tyr Lys Glu Ile Asn Asn Arg
65              70                  75                  80

Val Asn Val Ala Thr Asn Asn Pro Ala Ser Gln Gln Val Asp Lys His
                85                  90                  95

Phe Val Ala Lys Gly Pro Glu Val Asn Arg Phe Ile Thr Gln Asn Lys
            100                 105                 110

Val Asn His His Phe Ile Thr Thr Gln Thr His Tyr Lys Lys Val Ile
        115                 120                 125

Thr Ser Tyr Lys Ser Thr His Val Lys His Val Asn His Ala Lys
130                 135                 140

Asp Ser Ile Asn Lys His Phe Ile Val Lys Pro Ser Glu Ser Pro Arg
145                 150                 155                 160

Tyr Thr His Pro Ser Gln Ser Leu Ile Ile Lys His His Phe Ala Val
                165                 170                 175

Pro Gly Tyr His Ala His Lys Phe Val Thr Pro Gly His Ala Ser Ile
            180                 185                 190

Lys Ile Asn His Phe Cys Val Val Pro Gln Ile Asn Ser Phe Lys Val
        195                 200                 205

Ile Pro Pro Tyr Gly His Asn Ser His Arg Met His Val Pro Ser Phe
210                 215                 220

Gln Asn Asn Thr Thr Ala Thr His Gln Asn Ala Lys Val Asn Lys Ala
225                 230                 235                 240

Tyr Asp Tyr Lys Tyr Phe Tyr Ser Tyr Lys Val Val Lys Gly Val Lys
                245                 250                 255

Lys Tyr Phe Ser Phe Ser Gln Ser Asn Gly Tyr Lys Ile Gly Lys Pro
            260                 265                 270

Ser Leu Asn Ile Lys Asn Val Asn Tyr Gln Tyr Ala Val Pro Ser Tyr
        275                 280                 285

Ser Pro Thr His Tyr Val Pro Glu Phe Lys Gly Ser Leu Pro Ala Pro
290                 295                 300

Arg Val
305

<210> SEQ ID NO 15
<211> LENGTH: 308
<212> TYPE: PRT
<213> ORGANISM: Staphylococcus aureus

<400> SEQUENCE: 15

Ser Val Thr Glu Ser Val Asp Lys Lys Phe Val Val Pro Glu Ser Gly
1               5                   10                  15

Ile Asn Lys Ile Ile Pro Ala Tyr Asp Glu Phe Lys Asn Ser Pro Lys
            20                  25                  30

Val Asn Val Ser Asn Leu Thr Asp Asn Lys Asn Phe Val Ala Ser Glu
        35                  40                  45

Asp Lys Leu Asn Lys Ile Ala Asp Ser Ser Ala Ala Ser Lys Ile Val

```
            50                  55                  60
Asp Lys Asn Phe Val Val Pro Glu Ser Lys Leu Gly Asn Ile Val Pro
 65                  70                  75                  80

Glu Tyr Lys Glu Ile Asn Asn Arg Val Asn Val Ala Thr Asn Asn Pro
                 85                  90                  95

Ala Ser Gln Gln Val Asp Lys His Phe Val Ala Lys Gly Pro Glu Val
            100                 105                 110

Asn Arg Phe Ile Thr Gln Asn Lys Val Asn His Phe Ile Thr Thr
        115                 120                 125

Gln Thr His Tyr Lys Lys Val Ile Thr Ser Tyr Lys Ser Thr His Val
130                 135                 140

His Lys His Val Asn His Ala Lys Asp Ser Ile Asn Lys His Phe Ile
145                 150                 155                 160

Val Lys Pro Ser Glu Ser Pro Arg Tyr Thr His Pro Ser Gln Ser Leu
                165                 170                 175

Ile Ile Lys His His Phe Ala Val Pro Gly Tyr His Ala His Lys Phe
            180                 185                 190

Val Thr Pro Gly His Ala Ser Ile Lys Ile Asn His Phe Cys Val Val
        195                 200                 205

Pro Gln Ile Asn Ser Phe Lys Val Ile Pro Pro Tyr Gly His Asn Ser
    210                 215                 220

His Arg Met His Val Pro Ser Phe Gln Asn Asn Thr Thr Ala Thr His
225                 230                 235                 240

Gln Asn Ala Lys Val Asn Lys Ala Tyr Asp Tyr Lys Tyr Phe Tyr Ser
                245                 250                 255

Tyr Lys Val Val Lys Gly Val Lys Lys Tyr Phe Ser Phe Ser Gln Ser
            260                 265                 270

Asn Gly Tyr Lys Ile Gly Lys Pro Ser Leu Asn Ile Lys Asn Val Asn
        275                 280                 285

Tyr Gln Tyr Ala Val Pro Ser Tyr Ser Pro Thr His Tyr Val Pro Glu
    290                 295                 300

Phe Lys Gly Ser
305

<210> SEQ ID NO 16
<211> LENGTH: 300
<212> TYPE: PRT
<213> ORGANISM: Staphylococcus aureus

<400> SEQUENCE: 16

Lys Phe Val Val Pro Glu Ser Gly Ile Asn Lys Ile Ile Pro Ala Tyr
  1               5                  10                  15

Asp Glu Phe Lys Asn Ser Pro Lys Val Asn Val Ser Asn Leu Thr Asp
                 20                  25                  30

Asn Lys Asn Phe Val Ala Ser Glu Asp Lys Leu Asn Lys Ile Ala Asp
             35                  40                  45

Ser Ser Ala Ala Ser Lys Ile Val Asp Lys Asn Phe Val Val Pro Glu
         50                  55                  60

Ser Lys Leu Gly Asn Ile Val Pro Glu Tyr Lys Glu Ile Asn Asn Arg
 65                  70                  75                  80

Val Asn Val Ala Thr Asn Asn Pro Ala Ser Gln Gln Val Asp Lys His
                 85                  90                  95

Phe Val Ala Lys Gly Pro Glu Val Asn Arg Phe Ile Thr Gln Asn Lys
            100                 105                 110
```

```
Val Asn His His Phe Ile Thr Thr Gln Thr His Tyr Lys Lys Val Ile
        115                 120                 125

Thr Ser Tyr Lys Ser Thr His Val His Lys His Val Asn His Ala Lys
130                 135                 140

Asp Ser Ile Asn Lys His Phe Ile Val Lys Pro Ser Glu Ser Pro Arg
145                 150                 155                 160

Tyr Thr His Pro Ser Gln Ser Leu Ile Ile Lys His His Phe Ala Val
        165                 170                 175

Pro Gly Tyr His Ala His Lys Phe Val Thr Pro Gly His Ala Ser Ile
        180                 185                 190

Lys Ile Asn His Phe Cys Val Val Pro Gln Ile Asn Ser Phe Lys Val
        195                 200                 205

Ile Pro Pro Tyr Gly His Asn Ser His Arg Met His Val Pro Ser Phe
        210                 215                 220

Gln Asn Asn Thr Thr Ala Thr His Gln Asn Ala Lys Val Asn Lys Ala
225                 230                 235                 240

Tyr Asp Tyr Lys Tyr Phe Tyr Ser Tyr Lys Val Val Lys Gly Val Lys
        245                 250                 255

Lys Tyr Phe Ser Phe Ser Gln Ser Asn Gly Tyr Lys Ile Gly Lys Pro
        260                 265                 270

Ser Leu Asn Ile Lys Asn Val Asn Tyr Gln Tyr Ala Val Pro Ser Tyr
        275                 280                 285

Ser Pro Thr His Tyr Val Pro Glu Phe Lys Gly Ser
        290                 295                 300

<210> SEQ ID NO 17
<211> LENGTH: 121
<212> TYPE: PRT
<213> ORGANISM: Staphylococcus aureus

<400> SEQUENCE: 17

Ser Val Thr Glu Ser Val Asp Lys Lys Phe Val Pro Glu Ser Gly
1               5                   10                  15

Ile Asn Lys Ile Ile Pro Ala Tyr Asp Glu Phe Lys Asn Ser Pro Lys
            20                  25                  30

Val Asn Val Ser Asn Leu Thr Asp Asn Lys Asn Phe Val Ala Ser Glu
        35                  40                  45

Asp Lys Leu Asn Lys Ile Ala Asp Ser Ser Ala Ser Lys Ile Val
50                  55                  60

Asp Lys Asn Phe Val Val Pro Glu Ser Lys Leu Gly Asn Ile Val Pro
65                  70                  75                  80

Glu Tyr Lys Glu Ile Asn Asn Arg Val Asn Val Ala Thr Asn Asn Pro
            85                  90                  95

Ala Ser Gln Gln Val Asp Lys His Phe Val Ala Lys Gly Pro Glu Val
            100                 105                 110

Asn Arg Phe Ile Thr Gln Asn Lys Val
            115                 120

<210> SEQ ID NO 18
<211> LENGTH: 1349
<212> TYPE: PRT
<213> ORGANISM: Staphylococcus aureus

<400> SEQUENCE: 18

Met Leu Asn Arg Glu Asn Lys Thr Ala Ile Thr Arg Lys Gly Met Val
1               5                   10                  15
```

```
Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Asn Gln Lys Glu Met Val
                85                  90                  95

Ser Ser Gln Gly Asn Glu Thr Thr Ser Asn Gly Asn Lys Leu Ile Glu
            100                 105                 110

Lys Glu Ser Val Gln Ser Thr Thr Gly Asn Lys Val Glu Val Ser Thr
        115                 120                 125

Ala Lys Ser Asp Glu Gln Ala Ser Pro Lys Ser Thr Asn Glu Asp Leu
    130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
            180                 185                 190

Asp Ala Ile Lys Ser Asn Asp Glu Thr Leu Val Asp Asn Asn Ser Asn
        195                 200                 205

Ser Asn Asn Glu Asn Asn Ala Asp Ile Ile Leu Pro Lys Ser Thr Ala
    210                 215                 220

Pro Lys Arg Leu Asn Thr Arg Met Arg Ile Ala Ala Val Gln Pro Ser
225                 230                 235                 240

Ser Thr Glu Ala Lys Asn Val Asn Asp Leu Ile Thr Ser Asn Thr Thr
                245                 250                 255

Leu Thr Val Val Asp Ala Asp Lys Asn Asn Lys Ile Val Pro Ala Gln
            260                 265                 270

Asp Tyr Leu Ser Leu Lys Ser Gln Ile Thr Val Asp Asp Lys Val Lys
        275                 280                 285

Ser Gly Asp Tyr Phe Thr Ile Lys Tyr Ser Asp Thr Val Gln Val Tyr
    290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Gln Met Gly Ile Asn Tyr Ser Ile Tyr Met Asp Ala Asp Thr Ile Pro
        355                 360                 365

Val Ser Lys Asn Asp Val Glu Phe Asn Val Thr Ile Gly Asn Thr Thr
    370                 375                 380

Thr Lys Thr Thr Ala Asn Ile Gln Tyr Pro Asp Tyr Val Asn Asn Glu
385                 390                 395                 400

Lys Asn Ser Ile Gly Ser Ala Phe Thr Glu Thr Val Ser His Val Gly
                405                 410                 415

Asn Lys Glu Asn Pro Gly Tyr Tyr Lys Gln Thr Ile Tyr Val Asn Pro
            420                 425                 430

Ser Glu Asn Ser Leu Thr Asn Ala Lys Leu Lys Val Gln Ala Tyr His
```

-continued

```
            435                 440                 445

Ser Ser Tyr Pro Asn Asn Ile Gly Gln Ile Asn Lys Asp Val Thr Asp
450                 455                 460

Ile Lys Ile Tyr Gln Val Pro Lys Gly Tyr Thr Leu Asn Lys Gly Tyr
465                 470                 475                 480

Asp Val Asn Thr Lys Glu Leu Thr Asp Val Thr Asn Gln Tyr Leu Gln
                485                 490                 495

Lys Ile Thr Tyr Gly Asp Asn Asn Ser Ala Val Ile Asp Phe Gly Asn
                500                 505                 510

Ala Asp Ser Ala Tyr Val Val Met Val Asn Thr Lys Phe Gln Tyr Thr
                515                 520                 525

Asn Ser Glu Ser Pro Thr Leu Val Gln Met Ala Thr Leu Ser Ser Thr
530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
                580                 585                 590

Val Gly Asn Val Thr Val Thr Val Phe Asp Asn Asn Thr Asn Thr Lys
                595                 600                 605

Val Gly Glu Ala Val Thr Lys Glu Asp Gly Ser Tyr Leu Ile Pro Asn
610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
                660                 665                 670

Ala Asp Leu Gly Ile Tyr Lys Pro Lys Tyr Asn Leu Gly Asp Tyr Val
                675                 680                 685

Trp Glu Asp Thr Asn Lys Asn Gly Ile Gln Asp Gln Asp Glu Lys Gly
                690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
                740                 745                 750

Pro Thr Thr Val Thr Ser Gly Ser Asp Ile Glu Lys Asp Ser Asn Gly
                755                 760                 765

Leu Thr Thr Gly Val Ile Asn Gly Ala Asp Asn Met Thr Leu Asp
                770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
                820                 825                 830

Thr Thr Lys Thr Asp Lys Asp Gly Lys Tyr Gln Phe Thr Gly Leu Glu
                835                 840                 845

Asn Gly Thr Tyr Lys Val Glu Phe Glu Thr Pro Ser Gly Tyr Thr Pro
850                 855                 860
```

-continued

```
Thr Gln Val Gly Ser Gly Thr Asp Glu Gly Ile Asp Ser Asn Gly Thr
865                 870                 875                 880
Ser Thr Thr Gly Val Ile Lys Asp Lys Asp Asn Asp Thr Ile Asp Ser
                885                 890                 895
Gly Phe Tyr Lys Pro Thr Tyr Asn Leu Gly Asp Tyr Val Trp Glu Asp
            900                 905                 910
Thr Asn Lys Asn Gly Val Gln Asp Lys Asp Glu Lys Gly Ile Ser Gly
            915                 920                 925
Val Thr Val Thr Leu Lys Asp Glu Asn Asp Lys Val Leu Lys Thr Val
        930                 935                 940
Thr Thr Asp Glu Asn Gly Lys Tyr Gln Phe Thr Asp Leu Asn Asn Gly
945                 950                 955                 960
Thr Tyr Lys Val Glu Phe Glu Thr Pro Ser Gly Tyr Thr Pro Thr Ser
            965                 970                 975
Val Thr Ser Gly Asn Asp Thr Glu Lys Asp Ser Asn Gly Leu Thr Thr
            980                 985                 990
Thr Gly Val Ile Lys Asp Ala Asp Asn Met Thr Leu Asp Ser Gly Phe
        995                1000                1005
Tyr Lys Thr Pro Lys Tyr Ser Leu Gly Asp Tyr Val Trp Tyr Asp Ser
       1010                1015                1020
Asn Lys Asp Gly Lys Gln Asp Ser Thr Glu Lys Gly Ile Lys Asp Val
1025                1030                1035                1040
Lys Val Thr Leu Leu Asn Glu Lys Gly Glu Val Ile Gly Thr Thr Lys
                1045                1050                1055
Thr Asp Glu Asn Gly Lys Tyr Cys Phe Asp Asn Leu Asp Ser Gly Lys
            1060                1065                1070
Tyr Lys Val Ile Phe Glu Lys Pro Ala Gly Leu Thr Gln Thr Val Thr
       1075                1080                1085
Asn Thr Thr Glu Asp Asp Lys Asp Ala Asp Gly Gly Glu Val Asp Val
       1090                1095                1100
Thr Ile Thr Asp His Asp Asp Phe Thr Leu Asp Asn Gly Tyr Phe Glu
1105                1110                1115                1120
Glu Asp Thr Ser Asp Ser Asp Ser Asp Ser Asp Ser Asp Ser Asp Ser
                1125                1130                1135
Asp Ser Asp Ser Asp Ser Asp Ser Asp Ser Asp Ser Asp Ser Asp Ser
            1140                1145                1150
Asp Ser Asp Ser Asp Ser Asp Ser Asp Ser Asp Ser Asp Ser Asp Ser
            1155                1160                1165
Asp Ser Asp Ser Asp Ser Asp Ser Asp Ser Asp Ser Asp Ser Asp Ser
            1170                1175                1180
Asp Ser Asp Ser Asp Ser Asp Ser Asp Ser Asp Ser Asp Ser Asp Ser
1185                1190                1195                1200
Asp Ser Asp Ser Asp Ser Asp Ser Asp Ser Asp Ser Asp Ser Asp Ser
            1205                1210                1215
Asp Ser Asp Ser Asp Ser Asp Ser Asp Ser Asp Ser Asp Ser Asp Ser
            1220                1225                1230
Asp Ser Asp Ser Asp Ser Asp Ser Asp Ser Asp Ser Asp Ser Asp Ser
            1235                1240                1245
Asp Ser Asp Ser Asp Ser Asp Ser Asp Ser Asp Ser Asp Ser Asp Ser
            1250                1255                1260
Asp Ser Asp Ser Asp Ser Asp Ser Asp Ser Asp Ser Asp Ser Asp Ser
1265                1270                1275                1280
```

Asp Ser Asp Ser Asp Ser Asp Ser Asp Ala Gly Lys His Thr Pro Val
                1285            1290            1295

Lys Pro Met Ser Thr Thr Lys Asp His His Asn Lys Ala Lys Ala Leu
            1300            1305            1310

Pro Glu Thr Gly Ser Glu Asn Asn Gly Ser Asn Asn Ala Thr Leu Phe
            1315            1320            1325

Gly Gly Leu Phe Ala Ala Leu Gly Ser Leu Leu Leu Phe Gly Arg Arg
            1330            1335            1340

Lys Lys Gln Asn Lys
1345

<210> SEQ ID NO 19
<211> LENGTH: 540
<212> TYPE: PRT
<213> ORGANISM: Staphylococcus aureus

<400> SEQUENCE: 19

Ala Glu Ser Thr Asn Lys Glu Leu Asn Glu Ala Thr Thr Ser Ala Ser
 1               5                  10                  15

Asp Asn Gln Ser Ser Asp Lys Val Asp Met Gln Gln Leu Asn Gln Glu
            20                  25                  30

Asp Asn Thr Lys Asn Asp Asn Gln Lys Glu Met Val Ser Ser Gln Gly
        35                  40                  45

Asn Glu Thr Thr Ser Asn Gly Asn Lys Leu Ile Glu Lys Glu Ser Val
    50                  55                  60

Gln Ser Thr Thr Gly Asn Lys Val Glu Val Ser Thr Ala Lys Ser Asp
65                  70                  75                  80

Glu Gln Ala Ser Pro Lys Ser Thr Asn Glu Asp Leu Asn Thr Lys Gln
                85                  90                  95

Thr Ile Ser Asn Gln Glu Ala Leu Gln Pro Asp Leu Gln Glu Asn Lys
            100                 105                 110

Ser Val Val Asn Val Gln Pro Thr Asn Glu Glu Asn Lys Lys Val Asp
        115                 120                 125

Ala Lys Thr Glu Ser Thr Thr Leu Asn Val Lys Ser Asp Ala Ile Lys
    130                 135                 140

Ser Asn Asp Glu Thr Leu Val Asp Asn Asn Ser Asn Ser Asn Asn Glu
145                 150                 155                 160

Asn Asn Ala Asp Ile Ile Leu Pro Lys Ser Thr Ala Pro Lys Arg Leu
                165                 170                 175

Asn Thr Arg Met Arg Ile Ala Ala Val Gln Pro Ser Ser Thr Glu Ala
            180                 185                 190

Lys Asn Val Asn Asp Leu Ile Thr Ser Asn Thr Thr Leu Thr Val Val
        195                 200                 205

Asp Ala Asp Lys Asn Asn Lys Ile Val Pro Ala Gln Asp Tyr Leu Ser
    210                 215                 220

Leu Lys Ser Gln Ile Thr Val Asp Asp Lys Val Lys Ser Gly Asp Tyr
225                 230                 235                 240

Phe Thr Ile Lys Tyr Ser Asp Thr Val Gln Val Tyr Gly Leu Asn Pro
                245                 250                 255

Glu Asp Ile Lys Asn Ile Gly Asp Ile Lys Asp Pro Asn Asn Gly Glu
            260                 265                 270

Thr Ile Ala Thr Ala Lys His Asp Thr Ala Asn Asn Leu Ile Thr Tyr
        275                 280                 285

Thr Phe Thr Asp Tyr Val Asp Arg Phe Asn Ser Val Gln Met Gly Ile
    290                 295                 300

Asn Tyr Ser Ile Tyr Met Asp Ala Asp Thr Ile Pro Val Ser Lys Asn
305                 310                 315                 320

Asp Val Glu Phe Asn Val Thr Ile Gly Asn Thr Thr Lys Thr Thr
            325                 330                 335

Ala Asn Ile Gln Tyr Pro Asp Tyr Val Val Asn Glu Lys Asn Ser Ile
            340                 345                 350

Gly Ser Ala Phe Thr Glu Thr Val Ser His Val Gly Asn Lys Glu Asn
            355                 360                 365

Pro Gly Tyr Tyr Lys Gln Thr Ile Tyr Val Asn Pro Ser Glu Asn Ser
    370                 375                 380

Leu Thr Asn Ala Lys Leu Lys Val Gln Ala Tyr His Ser Ser Tyr Pro
385                 390                 395                 400

Asn Asn Ile Gly Gln Ile Asn Lys Asp Val Thr Asp Ile Lys Ile Tyr
            405                 410                 415

Gln Val Pro Lys Gly Tyr Thr Leu Asn Lys Gly Tyr Asp Val Asn Thr
            420                 425                 430

Lys Glu Leu Thr Asp Val Thr Asn Gln Tyr Leu Gln Lys Ile Thr Tyr
            435                 440                 445

Gly Asp Asn Asn Ser Ala Val Ile Asp Phe Gly Asn Ala Asp Ser Ala
    450                 455                 460

Tyr Val Val Met Val Asn Thr Lys Phe Gln Tyr Thr Asn Ser Glu Ser
465                 470                 475                 480

Pro Thr Leu Val Gln Met Ala Thr Leu Ser Ser Thr Gly Asn Lys Ser
            485                 490                 495

Val Ser Thr Gly Asn Ala Leu Gly Phe Thr Asn Asn Gln Ser Gly Gly
            500                 505                 510

Ala Gly Gln Glu Val Tyr Lys Ile Gly Asn Tyr Val Trp Glu Asp Thr
            515                 520                 525

Asn Lys Asn Gly Val Gln Glu Leu Gly Glu Lys Gly
    530                 535                 540

<210> SEQ ID NO 20
<211> LENGTH: 199
<212> TYPE: PRT
<213> ORGANISM: Staphylococcus aureus

<400> SEQUENCE: 20

Pro Asp Tyr Val Val Asn Glu Lys Asn Ser Ile Gly Ser Ala Phe Thr
1               5                   10                  15

Glu Thr Val Ser His Val Gly Asn Lys Glu Asn Pro Gly Tyr Tyr Lys
            20                  25                  30

Gln Thr Ile Tyr Val Asn Pro Ser Glu Asn Ser Leu Thr Asn Ala Lys
            35                  40                  45

Leu Lys Val Gln Ala Tyr His Ser Ser Tyr Pro Asn Asn Ile Gly Gln
    50                  55                  60

Ile Asn Lys Asp Val Thr Asp Ile Lys Ile Tyr Gln Val Pro Lys Gly
65                  70                  75                  80

Tyr Thr Leu Asn Lys Gly Tyr Asp Val Asn Thr Lys Glu Leu Thr Asp
            85                  90                  95

Val Thr Asn Gln Tyr Leu Gln Lys Ile Thr Tyr Gly Asp Asn Asn Ser
            100                 105                 110

Ala Val Ile Asp Phe Gly Asn Ala Asp Ser Ala Tyr Val Val Met Val
            115                 120                 125

Asn Thr Lys Phe Gln Tyr Thr Asn Ser Glu Ser Pro Thr Leu Val Gln

```
            130                 135                 140
Met Ala Thr Leu Ser Ser Thr Gly Asn Lys Ser Val Ser Thr Gly Asn
145                 150                 155                 160

Ala Leu Gly Phe Thr Asn Asn Gln Ser Gly Ala Gly Gln Glu Val
                165                 170                 175

Tyr Lys Ile Gly Asn Tyr Val Trp Glu Asp Thr Asn Lys Asn Gly Val
                180                 185                 190

Gln Glu Leu Gly Glu Lys Gly
            195

<210> SEQ ID NO 21
<211> LENGTH: 516
<212> TYPE: PRT
<213> ORGANISM: Staphylococcus aureus

<400> SEQUENCE: 21

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
                20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300
```

```
Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
            325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
            355                 360                 365

Glu Asp Gly Asn Lys Pro Gly Lys Glu Asp Asn Lys Pro Gly Lys
            370                 375                 380

Glu Asp Gly Asn Lys Pro Gly Lys Glu Asp Asn Lys Lys Pro Gly Lys
385                 390                 395                 400

Glu Asp Gly Asn Lys Pro Gly Lys Glu Asp Gly Asn Lys Pro Gly Lys
            405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
            435                 440                 445

Asn Lys Leu Ala Asp Lys Asn Met Ile Lys Pro Gly Gln Glu Leu Val
450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
            485                 490                 495

Phe Gly Gly Leu Ser Leu Ala Leu Gly Ala Ala Leu Leu Ala Gly Arg
            500                 505                 510

Arg Arg Glu Leu
        515

<210> SEQ ID NO 22
<211> LENGTH: 289
<212> TYPE: PRT
<213> ORGANISM: Staphylococcus aureus

<400> SEQUENCE: 22

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Gln Gln Ser Ala Phe Tyr Glu Ile Leu Asn Met Pro Asn
65                  70                  75                  80

Leu Asn Glu Ala Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160
```

```
Leu Leu Ser Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala

<210> SEQ ID NO 23
<211> LENGTH: 130
<212> TYPE: PRT
<213> ORGANISM: Staphylococcus aureus

<400> SEQUENCE: 23

Met Asn Phe Asn Asp Ile Glu Thr Met Val Lys Ser Lys Phe Lys Asp
  1               5                  10                  15

Ile Lys Lys His Ala Glu Glu Ile Ala His Glu Ile Glu Val Arg Ser
                20                  25                  30

Gly Tyr Leu Arg Lys Ala Glu Gln Tyr Lys Arg Leu Glu Phe Asn Leu
            35                  40                  45

Ser Phe Ala Leu Asp Asp Ile Glu Ser Thr Ala Lys Asp Val Gln Thr
        50                  55                  60

Ala Lys Ser Ser Ala Asn Lys Asp Ser Val Thr Val Lys Gly Lys Ala
 65                 70                  75                  80

Pro Asn Thr Leu Tyr Ile Glu Lys Arg Asn Leu Met Lys Gln Lys Leu
                85                  90                  95

Glu Met Leu Gly Glu Asp Ile Asp Lys Asn Lys Glu Ser Leu Gln Lys
            100                 105                 110

Ala Lys Glu Ile Ala Gly Glu Lys Ala Ser Glu Tyr Phe Asn Lys Ala
        115                 120                 125

Met Asn
130

<210> SEQ ID NO 24
<211> LENGTH: 97
<212> TYPE: PRT
<213> ORGANISM: Staphylococcus aureus

<400> SEQUENCE: 24

Met Ala Met Ile Lys Met Ser Pro Glu Glu Ile Arg Ala Lys Ser Gln
  1               5                  10                  15

Ser Tyr Gly Gln Gly Ser Asp Gln Ile Arg Gln Ile Leu Ser Asp Leu
                20                  25                  30

Thr Arg Ala Gln Gly Glu Ile Ala Ala Asn Trp Glu Gly Gln Ala Phe
            35                  40                  45
```

```
Ser Arg Phe Glu Glu Gln Phe Gln Gln Leu Ser Pro Lys Val Glu Lys
        50                  55                  60

Phe Ala Gln Leu Leu Glu Glu Ile Lys Gln Gln Leu Asn Ser Thr Ala
 65                  70                  75                  80

Asp Ala Val Gln Glu Gln Asp Gln Gln Leu Ser Asn Asn Phe Gly Leu
                 85                  90                  95

Gln

<210> SEQ ID NO 25
<211> LENGTH: 104
<212> TYPE: PRT
<213> ORGANISM: Staphylococcus aureus

<400> SEQUENCE: 25

Met Gly Gly Tyr Lys Gly Ile Lys Ala Asp Gly Gly Lys Val Asp Gln
  1               5                  10                  15

Ala Lys Gln Leu Ala Ala Lys Thr Ala Lys Asp Ile Glu Ala Cys Gln
                 20                  25                  30

Lys Gln Thr Gln Gln Leu Ala Glu Tyr Ile Glu Gly Ser Asp Trp Glu
                 35                  40                  45

Gly Gln Phe Ala Asn Lys Val Lys Asp Val Leu Leu Ile Met Ala Lys
         50                  55                  60

Phe Gln Glu Glu Leu Val Gln Pro Met Ala Asp His Gln Lys Ala Ile
 65                  70                  75                  80

Asp Asn Leu Ser Gln Asn Leu Ala Lys Tyr Asp Thr Leu Ser Ile Lys
                 85                  90                  95

Gln Gly Leu Asp Arg Val Asn Pro
            100

<210> SEQ ID NO 26
<211> LENGTH: 302
<212> TYPE: PRT
<213> ORGANISM: Staphylococcus aureus

<400> SEQUENCE: 26

Met Lys Lys Leu Leu Leu Pro Leu Ile Ile Met Leu Leu Val Leu Ala
  1               5                  10                  15

Ala Cys Gly Asn Gln Gly Glu Lys Asn Asn Lys Ala Glu Thr Lys Ser
                 20                  25                  30

Tyr Lys Met Asp Asp Gly Lys Thr Val Asp Ile Pro Lys Asp Pro Lys
                 35                  40                  45

Arg Ile Ala Val Val Ala Pro Thr Tyr Ala Gly Gly Leu Lys Lys Leu
         50                  55                  60

Gly Ala Asn Ile Val Ala Val Asn Gln Gln Val Asp Gln Ser Lys Val
 65                  70                  75                  80

Leu Lys Asp Lys Phe Lys Gly Val Thr Lys Ile Gly Asp Gly Asp Val
                 85                  90                  95

Glu Lys Val Ala Lys Glu Lys Pro Asp Leu Ile Ile Val Tyr Ser Thr
                100                 105                 110

Asp Lys Asp Ile Lys Lys Tyr Gln Lys Val Ala Pro Thr Val Val Val
                115                 120                 125

Asp Tyr Asn Lys His Lys Tyr Leu Glu Gln Gln Glu Met Leu Gly Lys
                130                 135                 140

Ile Val Gly Lys Glu Asp Lys Val Lys Ala Trp Lys Lys Asp Trp Glu
145                 150                 155                 160

Glu Thr Thr Ala Lys Asp Gly Lys Glu Ile Lys Lys Ala Ile Gly Gln
```

```
                  165                 170                 175
Asp Ala Thr Val Ser Leu Phe Asp Glu Phe Asp Lys Lys Leu Tyr Thr
                180                 185                 190

Tyr Gly Asp Asn Trp Gly Arg Gly Gly Glu Val Leu Tyr Gln Ala Phe
                195                 200                 205

Gly Leu Lys Met Gln Pro Glu Gln Gln Lys Leu Thr Ala Lys Ala Gly
        210                 215                 220

Trp Ala Glu Val Lys Gln Glu Glu Ile Glu Lys Tyr Ala Gly Asp Tyr
225                 230                 235                 240

Ile Val Ser Thr Ser Glu Gly Lys Pro Thr Pro Gly Tyr Glu Ser Thr
                245                 250                 255

Asn Met Trp Lys Asn Leu Lys Ala Thr Lys Glu Gly His Ile Val Lys
                260                 265                 270

Val Asp Ala Gly Thr Tyr Trp Tyr Asn Asp Pro Tyr Thr Leu Asp Phe
                275                 280                 285

Met Arg Lys Asp Leu Lys Glu Lys Leu Ile Lys Ala Ala Lys
                290                 295                 300

<210> SEQ ID NO 27
<211> LENGTH: 227
<212> TYPE: PRT
<213> ORGANISM: Staphylococcus aureus

<400> SEQUENCE: 27

Met Lys Asn Ile Leu Lys Val Phe Asn Thr Thr Ile Leu Ala Leu Ile
1               5                   10                  15

Ile Ile Ile Ala Thr Phe Ser Asn Ser Ala Asn Ala Ala Asp Ser Gly
                20                  25                  30

Thr Leu Asn Tyr Glu Val Tyr Lys Tyr Asn Thr Asn Asp Thr Ser Ile
            35                  40                  45

Ala Asn Asp Tyr Phe Asn Lys Pro Ala Lys Tyr Ile Lys Lys Asn Gly
        50                  55                  60

Lys Leu Tyr Val Gln Ile Thr Val Asn His Ser His Trp Ile Thr Gly
65              70                  75                  80

Met Ser Ile Glu Gly His Lys Glu Asn Ile Ile Ser Lys Asn Thr Ala
                85                  90                  95

Lys Asp Glu Arg Thr Ser Glu Phe Glu Val Ser Lys Leu Asn Gly Lys
            100                 105                 110

Ile Asp Gly Lys Ile Asp Val Tyr Ile Asp Glu Lys Val Asn Gly Lys
        115                 120                 125

Pro Phe Lys Tyr Asp His His Tyr Asn Ile Thr Tyr Lys Phe Asn Gly
    130                 135                 140

Pro Thr Asp Val Ala Gly Ala Asn Ala Pro Gly Lys Asp Asp Lys Asn
145                 150                 155                 160

Ser Ala Ser Gly Ser Asp Lys Gly Ser Asp Gly Thr Thr Thr Gly Gln
                165                 170                 175

Ser Glu Ser Asn Ser Ser Asn Lys Asp Lys Val Glu Asn Pro Gln Thr
                180                 185                 190

Asn Ala Gly Thr Pro Ala Tyr Ile Tyr Ala Ile Pro Val Ala Ser Leu
            195                 200                 205

Ala Leu Leu Ile Ala Ile Thr Leu Phe Val Arg Lys Lys Ser Lys Gly
        210                 215                 220

Asn Val Glu
225
```

<210> SEQ ID NO 28
<211> LENGTH: 319
<212> TYPE: PRT
<213> ORGANISM: Staphylococcus aureus

<400> SEQUENCE: 28

Met Lys Thr Arg Ile Val Ser Val Thr Thr Leu Leu Leu Gly
1               5                   10                  15

Ser Ile Leu Met Asn Pro Val Ala Asn Ala Asp Ser Asp Ile Asn
            20                  25                  30

Ile Lys Thr Gly Thr Thr Asp Ile Gly Ser Asn Thr Thr Val Lys Thr
        35                  40                  45

Gly Asp Leu Val Thr Tyr Asp Lys Glu Asn Gly Met His Lys Lys Val
    50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
        115                 120                 125

Pro Arg Asn Ser Ile Asp Thr Lys Glu Tyr Met Ser Thr Leu Thr Tyr
    130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Ile Asp Arg Ser
    290                 295                 300

Ser Glu Arg Tyr Lys Ile Asp Trp Glu Lys Glu Met Thr Asn
305                 310                 315

<210> SEQ ID NO 29
<211> LENGTH: 293
<212> TYPE: PRT
<213> ORGANISM: Staphylococcus aureus

<400> SEQUENCE: 29

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290

<210> SEQ ID NO 30
<211> LENGTH: 4
<212> TYPE: PRT
<213> ORGANISM: Artificial Sequence
<220> FEATURE:
<223> OTHER INFORMATION: Tetrapeptide loop replacement

<400> SEQUENCE: 30

Pro Ser Gly Ser
 1

<210> SEQ ID NO 31
<211> LENGTH: 258
<212> TYPE: PRT
<213> ORGANISM: Staphylococcus aureus

<400> SEQUENCE: 31

Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn

```
              20                  25                  30
Gly Met Leu Lys Lys Val Phe Tyr Ser Phe Ile Asp Asp Lys Asn His
             35                  40                  45
Asn Lys Lys Leu Leu Val Ile Arg Thr Lys Gly Thr Ile Ala Gly Gln
         50                  55                  60
Tyr Arg Val Tyr Ser Glu Glu Gly Ala Asn Lys Ser Gly Leu Ala Trp
 65                  70                  75                  80
Pro Ser Ala Phe Lys Val Gln Leu Gln Leu Pro Asp Asn Glu Val Ala
                 85                  90                  95
Gln Ile Ser Asp Tyr Tyr Pro Arg Asn Ser Ile Asp Thr Pro Ser Gly
                100                 105                 110
Ser Val Gln Pro Asp Phe Lys Thr Ile Leu Glu Ser Pro Thr Asp Lys
            115                 120                 125
Lys Val Gly Trp Lys Val Ile Phe Asn Asn Met Val Asn Gln Asn Trp
        130                 135                 140
Gly Pro Tyr Asp Arg Asp Ser Trp Asn Pro Val Tyr Gly Asn Gln Leu
145                 150                 155                 160
Phe Met Lys Thr Arg Asn Gly Ser Met Lys Ala Ala Asp Asn Phe Leu
                165                 170                 175
Asp Pro Asn Lys Ala Ser Ser Leu Leu Ser Ser Gly Phe Ser Pro Asp
            180                 185                 190
Phe Ala Thr Val Ile Thr Met Asp Arg Lys Ala Ser Lys Gln Gln Thr
        195                 200                 205
Asn Ile Asp Val Ile Tyr Glu Arg Val Arg Asp Asp Tyr Gln Leu His
    210                 215                 220
Trp Thr Ser Thr Asn Trp Lys Gly Thr Asn Thr Lys Asp Lys Trp Ile
225                 230                 235                 240
Asp Arg Ser Ser Glu Arg Tyr Lys Ile Asp Trp Glu Lys Glu Glu Met
                245                 250                 255
Thr Asn

<210> SEQ ID NO 32
<211> LENGTH: 258
<212> TYPE: PRT
<213> ORGANISM: Staphylococcus aureus

<400> SEQUENCE: 32

Ala Asp Ser Asp Ile Asn Ile Lys Thr Gly Thr Thr Asp Ile Gly Ser
  1               5                  10                  15
Asn Thr Thr Val Lys Thr Gly Asp Leu Val Thr Tyr Asp Lys Glu Asn
             20                  25                  30
Gly Met His Lys Lys Val Phe Tyr Ser Phe Ile Asp Asp Lys Asn His
             35                  40                  45
Asn Lys Lys Leu Leu Val Ile Arg Thr Lys Gly Thr Ile Ala Gly Gln
         50                  55                  60
Tyr Arg Val Tyr Ser Glu Glu Gly Ala Asn Lys Ser Gly Leu Ala Trp
 65                  70                  75                  80
Pro Ser Ala Phe Lys Val Gln Leu Gln Leu Pro Asp Asn Glu Val Ala
                 85                  90                  95
Gln Ile Ser Asp Tyr Tyr Pro Arg Asn Ser Ile Asp Thr Pro Ser Gly
                100                 105                 110
Ser Val Gln Pro Asp Phe Lys Thr Ile Leu Glu Ser Pro Thr Asp Lys
            115                 120                 125
Lys Val Gly Trp Lys Val Ile Phe Asn Asn Met Val Asn Gln Asn Trp
```

```
                130               135               140
Gly Pro Tyr Asp Arg Asp Ser Trp Asn Pro Val Tyr Gly Asn Gln Leu
145                 150                 155                 160

Phe Met Lys Thr Arg Asn Gly Ser Met Lys Ala Ala Asp Asn Phe Leu
                165                 170                 175

Asp Pro Asn Lys Ala Ser Ser Leu Leu Ser Ser Gly Phe Ser Pro Asp
            180                 185                 190

Phe Ala Thr Val Ile Thr Met Asp Arg Lys Ala Ser Lys Gln Gln Thr
        195                 200                 205

Asn Ile Asp Val Ile Tyr Glu Arg Val Arg Asp Asp Tyr Gln Leu His
    210                 215                 220

Trp Thr Ser Thr Asn Trp Lys Gly Thr Asn Thr Lys Asp Lys Trp Ile
225                 230                 235                 240

Asp Arg Ser Ser Glu Arg Tyr Lys Ile Asp Trp Glu Lys Glu Glu Met
                245                 250                 255

Thr Asn

<210> SEQ ID NO 33
<211> LENGTH: 50
<212> TYPE: PRT
<213> ORGANISM: Staphylococcus aureus

<400> SEQUENCE: 33

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys
    50

<210> SEQ ID NO 34
<211> LENGTH: 63
<212> TYPE: PRT
<213> ORGANISM: Staphylococcus aureus

<400> SEQUENCE: 34

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly
    50                  55                  60

<210> SEQ ID NO 35
<211> LENGTH: 53
<212> TYPE: PRT
<213> ORGANISM: Staphylococcus aureus

<400> SEQUENCE: 35

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30
```

Gly Met His Lys Lys Val Phe Tyr Ser Phe Ile Asp Asp Lys Asn His
            35                  40                  45

Asn Lys Lys Leu Leu
    50

<210> SEQ ID NO 36
<211> LENGTH: 50
<212> TYPE: PRT
<213> ORGANISM: Staphylococcus aureus

<400> SEQUENCE: 36

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
            35                  40                  45

Asn Lys
    50

<210> SEQ ID NO 37
<211> LENGTH: 63
<212> TYPE: PRT
<213> ORGANISM: Staphylococcus aureus

<400> SEQUENCE: 37

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly
    50                  55                  60

<210> SEQ ID NO 38
<211> LENGTH: 53
<212> TYPE: PRT
<213> ORGANISM: Staphylococcus aureus

<400> SEQUENCE: 38

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
            35                  40                  45

Asn Lys Lys Leu Leu
    50

<210> SEQ ID NO 39
<211> LENGTH: 256
<212> TYPE: PRT
<213> ORGANISM: Staphylococcus aureus

<400> SEQUENCE: 39

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

```
Val Lys Lys Ser Phe Glu Lys Thr Leu Ser Met Tyr Pro Ile Lys Asn
         35                  40                  45

Leu Glu Asp Leu Tyr Asp Lys Glu Gly Tyr Arg Asp Asp Gln Phe Asp
     50                  55                  60

Lys Asn Asp Lys Gly Thr Trp Ile Ile Asn Ser Glu Met Val Ile Gln
 65                  70                  75                  80

Pro Asn Asn Glu Asp Met Val Ala Lys Gly Met Val Leu Tyr Met Asn
                 85                  90                  95

Arg Asn Thr Lys Thr Thr Asn Gly Tyr Tyr Tyr Val Asp Val Thr Lys
                100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
        130                 135                 140

Lys Ile Lys Lys Glu Ile Glu Asn Phe Lys Phe Phe Val Gln Tyr Gly
145                 150                 155                 160

Asp Phe Lys Asn Leu Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 40
<211> LENGTH: 256
<212> TYPE: PRT
<213> ORGANISM: Staphylococcus aureus

<400> SEQUENCE: 40

Met Met Lys Arg Leu Asn Lys Leu Val Leu Gly Ile Ile Phe Leu Phe
 1               5                  10                  15

Leu Val Ile Ser Ile Thr Ala Gly Cys Gly Ile Gly Lys Glu Ala Glu
                 20                  25                  30

Val Lys Lys Ser Phe Glu Lys Thr Leu Ser Met Tyr Pro Ile Lys Asn
         35                  40                  45

Leu Glu Asp Leu Tyr Asp Lys Glu Gly Tyr Arg Asp Asp Gln Phe Asp
     50                  55                  60

Lys Asn Asp Lys Gly Thr Trp Ile Ile Asn Ser Glu Met Val Ile Gln
 65                  70                  75                  80

Pro Asn Asn Glu Asp Met Val Ala Lys Gly Met Val Leu Tyr Met Asn
                 85                  90                  95

Arg Asn Thr Lys Thr Thr Asn Gly Tyr Tyr Tyr Val Asp Val Thr Lys
                100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
        130                 135                 140

Lys Leu Lys Lys Glu Ile Glu Asn Phe Lys Phe Phe Val Gln Tyr Gly
```

-continued

```
                 145                 150                 155                 160
Asp Phe Lys Asn Ile Lys Asn Tyr Lys Asp Gly Asp Ile Ser Tyr Asn
                 165                 170                 175
Pro Glu Val Pro Ser Tyr Ser Ala Lys Tyr Gln Leu Thr Asn Asp Asp
                 180                 185                 190
Tyr Asn Val Lys Gln Leu Arg Lys Arg Tyr Asp Ile Pro Thr Ser Lys
                 195                 200                 205
Ala Pro Lys Leu Leu Lys Gly Ser Gly Asn Leu Lys Gly Ser Ser
210                 215                 220
Val Gly Tyr Lys Asp Ile Glu Phe Thr Phe Val Glu Lys Lys Glu Glu
225                 230                 235                 240
Asn Ile Tyr Phe Ser Asp Ser Leu Asp Tyr Lys Lys Ser Gly Asp Val
                 245                 250                 255

<210> SEQ ID NO 41
<211> LENGTH: 256
<212> TYPE: PRT
<213> ORGANISM: Staphylococcus aureus

<400> SEQUENCE: 41

Met Met Lys Arg Leu Asn Lys Leu Val Leu Gly Ile Ile Phe Leu Phe
1               5                   10                  15
Leu Val Ile Ser Ile Thr Ala Gly Cys Gly Ile Gly Lys Glu Ala Glu
                20                  25                  30
Val Lys Lys Ser Phe Glu Lys Thr Leu Ser Met Tyr Pro Ile Lys Asn
                35                  40                  45
Leu Glu Asp Leu Tyr Asp Lys Glu Gly Tyr Arg Asp Asp Gln Phe Asp
            50                  55                  60
Lys Asn Asp Lys Gly Thr Trp Ile Ile Asn Ser Glu Met Val Ile Gln
65                  70                  75                  80
Pro Asn Asn Glu Asp Met Val Ala Lys Gly Met Val Leu Tyr Met Asn
                85                  90                  95
Arg Asn Thr Lys Thr Thr Asn Gly Tyr Tyr Tyr Val Asp Val Thr Lys
                100                 105                 110
Asp Glu Asp Glu Gly Lys Pro His Asp Asn Lys Arg Tyr Pro Val
                115                 120                 125
Lys Met Val Asp Asn Lys Ile Ile Pro Thr Lys Glu Ile Lys Asp Glu
                130                 135                 140
Lys Val Lys Lys Glu Ile Glu Asn Phe Lys Phe Val Gln Tyr Gly
145                 150                 155                 160
Asp Phe Lys Asn Ile Lys Asn Tyr Lys Asp Gly Asp Ile Ser Tyr Asn
                165                 170                 175
Pro Glu Val Pro Ser Tyr Ser Ala Lys Tyr Gln Leu Thr Asn Asp Asp
                180                 185                 190
Tyr Asn Val Lys Gln Leu Arg Lys Arg Tyr Asp Ile Pro Thr Ser Lys
                195                 200                 205
Ala Pro Lys Leu Leu Lys Gly Ser Gly Asn Leu Lys Gly Ser Ser
210                 215                 220
Val Gly Tyr Lys Asp Ile Glu Phe Thr Phe Val Glu Lys Lys Glu Glu
225                 230                 235                 240
Asn Ile Tyr Phe Ser Asp Ser Leu Asp Tyr Lys Lys Ser Gly Asp Val
                245                 250                 255

<210> SEQ ID NO 42
<211> LENGTH: 256
```

```
<212> TYPE: PRT
<213> ORGANISM: Staphylococcus aureus

<400> SEQUENCE: 42

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
                20                  25                  30

Val Lys Lys Ser Phe Glu Lys Thr Leu Ser Met Tyr Pro Ile Lys Asn
            35                  40                  45

Leu Glu Asp Leu Tyr Asp Lys Glu Gly Tyr Arg Asp Asp Gln Phe Asp
        50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
            100                 105                 110

Asp Glu Asp Glu Gly Lys Pro His Asp Asn Glu Lys Arg Tyr Pro Val
        115                 120                 125

Lys Met Val Asp Asn Lys Ile Ile Pro Thr Lys Glu Ile Lys Asp Glu
130                 135                 140

Lys Leu Lys Lys Glu Ile Glu Asn Phe Lys Phe Phe Val Gln Tyr Gly
145                 150                 155                 160

Asp Phe Lys Asn Val Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Leu Lys Gly Ser Gly Asn Leu Lys Gly Ser Ser
210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 43
<211> LENGTH: 350
<212> TYPE: PRT
<213> ORGANISM: Staphylococcus aureus

<400> SEQUENCE: 43

Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
                20                  25                  30

Ser Leu Val Tyr Ile Gly Ala Asp Ser Gln Gln Val Asn Ala Ala Thr
            35                  40                  45

Glu Ala Thr Asn Ala Thr Asn Asn Gln Ser Thr Gln Val Ser Gln Ala
        50                  55                  60

Thr Ser Gln Pro Ile Asn Phe Gln Val Gln Lys Asp Gly Ser Ser Glu
65                  70                  75                  80

Lys Ser His Met Asp Asp Tyr Met Gln His Pro Gly Lys Val Ile Lys
                85                  90                  95
```

Gln Asn Asn Lys Tyr Tyr Phe Gln Thr Val Leu Asn Ala Ser Phe
            100                 105                 110

Trp Lys Glu Tyr Lys Phe Tyr Asn Ala Asn Gln Glu Leu Ala Thr
            115                 120                 125

Thr Val Val Asn Asp Asn Lys Lys Ala Asp Thr Arg Thr Ile Asn Val
130             135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
            165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
            195                 200                 205

Thr Lys Pro Val Gln Pro Lys Val Glu Lys Val Lys Pro Thr Val Thr
            210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
            245                 250                 255

Thr Ala Gln Thr Ala Gln Glu Gln Asn Lys Val Gln Thr Pro Val Lys
            260                 265                 270

Asp Val Ala Thr Ala Lys Ser Glu Ser Asn Asn Gln Ala Val Ser Asp
            275                 280                 285

Asn Lys Ser Gln Gln Thr Asn Lys Val Thr Lys His Asn Glu Thr Pro
290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Ala Thr Leu Ala Leu Leu
            325                 330                 335

Gly Ser Leu Ser Leu Leu Leu Phe Lys Arg Lys Glu Ser Lys
            340                 345                 350

<210> SEQ ID NO 44
<211> LENGTH: 145
<212> TYPE: PRT
<213> ORGANISM: Staphylococcus aureus

<400> SEQUENCE: 44

Asp Ser Gln Gln Val Asn Ala Ala Thr Glu Ala Thr Asn Ala Thr Asn
1               5                   10                  15

Asn Gln Ser Thr Gln Val Ser Gln Ala Thr Ser Gln Pro Ile Asn Phe
            20                  25                  30

Gln Val Gln Lys Asp Gly Ser Ser Glu Lys Ser His Met Asp Asp Tyr
            35                  40                  45

Met Gln His Pro Gly Lys Val Ile Lys Gln Asn Asn Lys Tyr Tyr Phe
            50                  55                  60

Gln Thr Val Leu Asn Asn Ala Ser Phe Trp Lys Glu Tyr Lys Phe Tyr
65              70                  75                  80

Asn Ala Asn Asn Gln Glu Leu Ala Thr Thr Val Val Asn Asp Asn Lys
            85                  90                  95

Lys Ala Asp Thr Arg Thr Ile Asn Val Ala Val Glu Pro Gly Tyr Lys
            100                 105                 110

Ser Leu Thr Thr Lys Val His Ile Val Val Pro Gln Ile Asn Tyr Asn
            115                 120                 125

His Arg Tyr Thr Thr His Leu Glu Phe Glu Lys Ala Ile Pro Thr Leu
130                 135                 140
Ala
145

<210> SEQ ID NO 45
<211> LENGTH: 645
<212> TYPE: PRT
<213> ORGANISM: Staphylococcus aureus

<400> SEQUENCE: 45

Met Asn Lys Gln Gln Lys Glu Phe Lys Ser Phe Tyr Ser Ile Arg Lys
  1               5                  10                  15

Ser Ser Leu Gly Val Ala Ser Val Ala Ile Ser Thr Leu Leu Leu Leu
               20                  25                  30

Met Ser Asn Gly Glu Ala Gln Ala Ala Glu Glu Thr Gly Gly Thr
           35                  40                  45

Asn Thr Glu Ala Gln Pro Lys Thr Glu Ala Val Ala Ser Pro Thr Thr
         50                  55                  60

Thr Ser Glu Lys Ala Pro Glu Thr Lys Pro Val Ala Asn Ala Val Ser
 65                  70                  75                  80

Val Ser Asn Lys Glu Val Glu Ala Pro Thr Ser Glu Thr Lys Glu Ala
                 85                  90                  95

Lys Glu Val Lys Glu Val Lys Ala Pro Lys Glu Thr Lys Glu Val Lys
                100                 105                 110

Pro Ala Ala Lys Ala Thr Asn Asn Thr Tyr Pro Ile Leu Asn Gln Glu
            115                 120                 125

Leu Arg Glu Ala Ile Lys Asn Pro Ala Ile Lys Asp Lys Asp His Ser
130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Ala Lys Thr Leu
        275                 280                 285

Glu Arg Gln Val Tyr Glu Leu Asn Lys Ile Gln Asp Lys Leu Pro Glu
290                 295                 300

Lys Leu Lys Ala Glu Tyr Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val

```
                340                 345                 350
Tyr Glu Ser Val Glu Asn Asn Glu Ser Met Met Asp Thr Phe Val Lys
            355                 360                 365

His Pro Ile Lys Thr Gly Met Leu Asn Gly Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645

<210> SEQ ID NO 46
<211> LENGTH: 1256
<212> TYPE: PRT
<213> ORGANISM: Staphylococcus aureus

<400> SEQUENCE: 46

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
    50                  55                  60
```

-continued

```
Asn Ile Ser Gly Thr Gln Val Tyr Gln Asp Pro Ala Ile Val Gln Pro
 65                  70                  75                  80

Lys Thr Ala Asn Asn Lys Thr Gly Asn Ala Gln Val Ser Gln Lys Val
                 85                  90                  95

Asp Thr Ala Gln Val Asn Gly Asp Thr Arg Ala Asn Gln Ser Ala Thr
            100                 105                 110

Thr Asn Asn Thr Gln Pro Val Ala Lys Ser Thr Ser Thr Ala Pro
        115                 120                 125

Lys Thr Asn Thr Asn Val Thr Asn Ala Gly Tyr Ser Leu Val Asp Asp
    130                 135                 140

Glu Asp Asp Asn Ser Glu Asn Gln Ile Asn Pro Glu Leu Ile Lys Ser
145                 150                 155                 160

Ala Ala Lys Pro Ala Ala Leu Glu Thr Gln Tyr Lys Thr Ala Ala Pro
                165                 170                 175

Lys Ala Ala Thr Thr Ser Ala Pro Lys Ala Lys Thr Glu Ala Thr Pro
            180                 185                 190

Lys Val Thr Thr Phe Ser Ala Ser Ala Gln Pro Arg Ser Val Ala Ala
        195                 200                 205

Thr Pro Lys Thr Ser Leu Pro Lys Tyr Lys Pro Gln Val Asn Ser Ser
210                 215                 220

Ile Asn Asp Tyr Ile Cys Lys Asn Asn Leu Lys Ala Pro Lys Ile Glu
225                 230                 235                 240

Glu Asp Tyr Thr Ser Tyr Phe Pro Lys Tyr Ala Tyr Arg Asn Gly Val
                245                 250                 255

Gly Arg Pro Glu Gly Ile Val Val His Asp Thr Ala Asn Asp Arg Ser
            260                 265                 270

Thr Ile Asn Gly Glu Ile Ser Tyr Met Lys Asn Asn Tyr Gln Asn Ala
        275                 280                 285

Phe Val His Ala Phe Val Asp Gly Asp Arg Ile Ile Glu Thr Ala Pro
    290                 295                 300

Thr Asp Tyr Leu Ser Trp Gly Val Gly Ala Val Gly Asn Pro Arg Phe
305                 310                 315                 320

Ile Asn Val Glu Ile Val His Thr His Asp Tyr Ala Ser Phe Ala Arg
                325                 330                 335

Ser Met Asn Asn Tyr Ala Asp Tyr Ala Ala Thr Gln Leu Gln Tyr Tyr
            340                 345                 350

Gly Leu Lys Pro Asp Ser Ala Glu Tyr Asp Gly Asn Gly Thr Val Trp
        355                 360                 365

Thr His Tyr Ala Val Ser Lys Tyr Leu Gly Gly Thr Asp His Ala Asp
    370                 375                 380

Pro His Gly Tyr Leu Arg Ser His Asn Tyr Ser Tyr Asp Gln Leu Tyr
385                 390                 395                 400

Asp Leu Ile Asn Glu Lys Tyr Leu Ile Lys Met Gly Lys Val Ala Pro
                405                 410                 415

Trp Gly Thr Gln Ser Thr Thr Thr Pro Thr Thr Pro Ser Lys Pro Thr
            420                 425                 430

Thr Pro Ser Lys Pro Ser Thr Gly Lys Leu Thr Val Ala Ala Asn Asn
        435                 440                 445

Gly Val Ala Gln Ile Lys Pro Thr Asn Ser Gly Leu Tyr Thr Thr Val
    450                 455                 460

Tyr Asp Lys Thr Gly Lys Ala Thr Asn Glu Val Gln Lys Thr Phe Ala
465                 470                 475                 480

Val Ser Lys Thr Ala Thr Leu Gly Asn Gln Lys Phe Tyr Leu Val Gln
```

```
            485                 490                 495
Asp Tyr Asn Ser Gly Asn Lys Phe Gly Trp Val Lys Glu Gly Asp Val
            500                 505                 510

Val Tyr Asn Thr Ala Lys Ser Pro Val Asn Val Asn Gln Ser Tyr Ser
            515                 520                 525

Ile Lys Pro Gly Thr Lys Leu Tyr Thr Val Pro Trp Gly Thr Ser Lys
            530                 535                 540

Gln Val Ala Gly Ser Val Ser Gly Ser Asn Gln Thr Phe Lys Ala
545                 550                 555                 560

Ser Lys Gln Gln Gln Ile Asp Lys Ser Ile Tyr Leu Tyr Gly Ser Val
                    565                 570                 575

Asn Gly Lys Ser Gly Trp Val Ser Lys Ala Tyr Leu Val Asp Thr Ala
                    580                 585                 590

Lys Pro Thr Pro Thr Pro Thr Pro Lys Pro Ser Thr Pro Thr Thr Asn
                    595                 600                 605

Asn Lys Leu Thr Val Ser Ser Leu Asn Gly Val Ala Gln Ile Asn Ala
                    610                 615                 620

Lys Asn Asn Gly Leu Phe Thr Thr Val Tyr Asp Lys Thr Gly Lys Pro
625                 630                 635                 640

Thr Lys Glu Val Gln Lys Thr Phe Ala Val Thr Lys Glu Ala Ser Leu
                    645                 650                 655

Gly Gly Asn Lys Phe Tyr Leu Val Lys Asp Tyr Asn Ser Pro Thr Leu
                    660                 665                 670

Ile Gly Trp Val Lys Gln Gly Asp Val Ile Tyr Asn Asn Ala Lys Ser
                    675                 680                 685

Pro Val Asn Val Met Gln Thr Tyr Thr Val Lys Pro Gly Thr Lys Leu
                    690                 695                 700

Tyr Ser Val Pro Trp Gly Thr Tyr Lys Gln Glu Ala Gly Ala Val Ser
705                 710                 715                 720

Gly Thr Gly Asn Gln Thr Phe Lys Ala Thr Lys Gln Gln Gln Ile Asp
                    725                 730                 735

Lys Ser Ile Tyr Leu Phe Gly Thr Val Asn Gly Lys Ser Gly Trp Val
                    740                 745                 750

Ser Lys Ala Tyr Leu Ala Val Pro Ala Ala Pro Lys Lys Ala Val Ala
                    755                 760                 765

Gln Pro Lys Thr Ala Val Lys Ala Tyr Thr Val Thr Lys Pro Gln Thr
                    770                 775                 780

Thr Gln Thr Val Ser Lys Ile Ala Gln Val Lys Pro Asn Asn Thr Gly
785                 790                 795                 800

Ile Arg Ala Ser Val Tyr Glu Lys Thr Ala Lys Asn Gly Ala Lys Tyr
                    805                 810                 815

Ala Asp Arg Thr Phe Tyr Val Thr Lys Glu Arg Ala His Gly Asn Glu
                    820                 825                 830

Thr Tyr Val Leu Leu Asn Asn Thr Ser His Asn Ile Pro Leu Gly Trp
                    835                 840                 845

Phe Asn Val Lys Asp Leu Asn Val Gln Asn Leu Gly Lys Glu Val Lys
                    850                 855                 860

Thr Thr Gln Lys Tyr Thr Val Asn Lys Ser Asn Asn Gly Leu Ser Met
865                 870                 875                 880

Val Pro Trp Gly Thr Lys Asn Gln Val Ile Leu Thr Gly Asn Asn Ile
                    885                 890                 895

Ala Gln Gly Thr Phe Asn Ala Thr Lys Gln Val Ser Val Gly Lys Asp
                    900                 905                 910
```

Val Tyr Leu Tyr Gly Thr Ile Asn Asn Arg Thr Gly Trp Val Asn Ala
            915                 920                 925

Lys Asp Leu Thr Ala Pro Thr Ala Val Lys Pro Thr Thr Ser Ala Ala
    930                 935                 940

Lys Asp Tyr Asn Tyr Thr Tyr Val Ile Lys Asn Gly Asn Gly Tyr Tyr
945                 950                 955                 960

Tyr Val Thr Pro Asn Ser Asp Thr Ala Lys Tyr Ser Leu Lys Ala Phe
            965                 970                 975

Asn Glu Gln Pro Phe Ala Val Val Lys Glu Gln Val Ile Asn Gly Gln
            980                 985                 990

Thr Trp Tyr Tyr Gly Lys Leu Ser Asn Gly Lys Leu Ala Trp Ile Lys
            995                 1000                1005

Ser Thr Asp Leu Ala Lys Glu Leu Ile Lys Tyr Asn Gln Thr Gly Met
    1010                1015                1020

Thr Leu Asn Gln Val Ala Gln Ile Gln Ala Gly Leu Gln Tyr Lys Pro
1025                1030                1035                1040

Gln Val Gln Arg Val Pro Gly Lys Trp Thr Asp Ala Lys Phe Asn Asp
            1045                1050                1055

Val Lys His Ala Met Asp Thr Lys Arg Leu Ala Gln Asp Pro Ala Leu
            1060                1065                1070

Lys Tyr Gln Phe Leu Arg Leu Asp Gln Pro Gln Asn Ile Ser Ile Asp
            1075                1080                1085

Lys Ile Asn Gln Phe Leu Lys Gly Lys Gly Val Leu Glu Asn Gln Gly
            1090                1095                1100

Ala Ala Phe Asn Lys Ala Lys Ala Gln Met Tyr Gly Ile Asn Glu Val Tyr
1105                1110                1115                1120

Leu Ile Ser His Ala Leu Leu Glu Thr Gly Asn Gly Thr Ser Gln Leu
            1125                1130                1135

Ala Lys Gly Ala Asp Val Val Asn Asn Lys Val Val Thr Asn Ser Asn
            1140                1145                1150

Thr Lys Tyr His Asn Val Phe Gly Ile Ala Ala Tyr Asp Asn Asp Pro
            1155                1160                1165

Leu Arg Glu Gly Ile Lys Tyr Ala Lys Gln Ala Gly Trp Asp Thr Val
            1170                1175                1180

Ser Lys Ala Ile Val Gly Gly Ala Lys Phe Ile Gly Asn Ser Tyr Val
1185                1190                1195                1200

Lys Ala Gly Gln Asn Thr Leu Tyr Lys Met Arg Trp Asn Pro Ala His
            1205                1210                1215

Pro Gly Thr His Gln Tyr Ala Thr Asp Val Asp Trp Ala Asn Ile Asn
            1220                1225                1230

Ala Lys Ile Ile Lys Gly Tyr Tyr Asp Lys Ile Gly Glu Val Gly Lys
            1235                1240                1245

Tyr Phe Asp Ile Pro Gln Tyr Lys
    1250                1255

<210> SEQ ID NO 47
<211> LENGTH: 6
<212> TYPE: PRT
<213> ORGANISM: Artificial Sequence
<220> FEATURE:
<223> OTHER INFORMATION: linker

<400> SEQUENCE: 47

Gly Ser Gly Gly Gly Gly
 1               5

<210> SEQ ID NO 48
<211> LENGTH: 8
<212> TYPE: PRT
<213> ORGANISM: Artificial Sequence
<220> FEATURE:
<223> OTHER INFORMATION: linker

<400> SEQUENCE: 48

Gly Ser Gly Ser Gly Gly Gly Gly
 1               5

<210> SEQ ID NO 49
<211> LENGTH: 6
<212> TYPE: PRT
<213> ORGANISM: Artificial Sequence
<220> FEATURE:
<223> OTHER INFORMATION: linker

<400> SEQUENCE: 49

Ala Ser Gly Gly Gly Ser
 1               5

<210> SEQ ID NO 50
<211> LENGTH: 18
<212> TYPE: DNA
<213> ORGANISM: Artificial Sequence
<220> FEATURE:
<223> OTHER INFORMATION: Synthetic Construct

<400> SEQUENCE: 50
gctagcggtg gcggatcc                                                     18

<210> SEQ ID NO 51
<211> LENGTH: 6
<212> TYPE: PRT
<213> ORGANISM: Artificial Sequence
<220> FEATURE:
<223> OTHER INFORMATION: hexahistidine tag

<400> SEQUENCE: 51

His His His His His His
 1               5

<210> SEQ ID NO 52
<211> LENGTH: 207
<212> TYPE: PRT
<213> ORGANISM: Staphylococcus aureus

<400> SEQUENCE: 52

Met Ala Met Ile Lys Met Ser Pro Glu Glu Ile Arg Ala Lys Ser Gln
 1               5                  10                  15

Ser Tyr Gly Gln Gly Ser Asp Gln Ile Arg Gln Ile Leu Ser Asp Leu
                20                  25                  30

Thr Arg Ala Gln Gly Glu Ile Ala Ala Asn Trp Glu Gly Gln Ala Phe
            35                  40                  45

Ser Arg Phe Glu Glu Gln Phe Gln Gln Leu Ser Pro Lys Val Glu Lys
        50                  55                  60

Phe Ala Gln Leu Leu Glu Glu Ile Lys Gln Gln Leu Asn Ser Thr Ala
 65                  70                  75                  80

Asp Ala Val Gln Glu Gln Asp Gln Gln Leu Ser Asn Asn Phe Gly Leu
                85                  90                  95

Gln Ala Ser Gly Gly Gly Ser Met Gly Gly Tyr Lys Gly Ile Lys Ala

```
            100                 105                 110
Asp Gly Gly Lys Val Asp Gln Ala Lys Gln Leu Ala Ala Lys Thr Ala
        115                 120                 125

Lys Asp Ile Glu Ala Cys Gln Lys Gln Thr Gln Gln Leu Ala Glu Tyr
    130                 135                 140

Ile Glu Gly Ser Asp Trp Glu Gly Gln Phe Ala Asn Lys Val Lys Asp
145                 150                 155                 160

Val Leu Leu Ile Met Ala Lys Phe Gln Glu Glu Leu Val Gln Pro Met
                165                 170                 175

Ala Asp His Gln Lys Ala Ile Asp Asn Leu Ser Gln Asn Leu Ala Lys
            180                 185                 190

Tyr Asp Thr Leu Ser Ile Lys Gln Gly Leu Asp Arg Val Asn Pro
        195                 200                 205

<210> SEQ ID NO 53
<211> LENGTH: 618
<212> TYPE: DNA
<213> ORGANISM: Staphylococcus aureus

<400> SEQUENCE: 53
atggcaatga ttaagatgag tccagaggaa atcagagcaa atcgcaatc ttacgggcaa      60 ggttcagacc aaatccgtca aattttatct gatttaacac gtgcacaagg tgaaattgca    120
gcgaactggg aaggtcaagc tttcagccgt ttcgaagagc aattccaaca acttagtcct    180
aaagtagaaa aatttgcaca attattagaa gaaattaaac aacaattgaa tagcactgct    240
gatgccgttc aagaacaaga ccaacaactt tctaataatt tcggtttgca agctagcggt    300
ggcggatccg gtggatataa aggtattaaa gcagatggtg gcaaggttga tcaagcgaaa    360
caattagcgg caaaaacagc taagatatt gaagcatgtc aaaagcaaac gcaacagctc    420
gctgagtata tcgaaggtag tgattgggaa ggacagttcg ccaataaggt gaaagatgtg    480
ttactcatta tggcaaagtt tcaagaagaa ttagtacaac cgatggctga ccatcaaaaa    540
gcaattgata acttaagtca aaatctagcg aaatacgata cattatcaat taagcaaggg    600
cttgataggg tgaaccca                                                   618

<210> SEQ ID NO 54
<211> LENGTH: 207
<212> TYPE: PRT
<213> ORGANISM: Staphylococcus aureus

<400> SEQUENCE: 54

Met Gly Gly Tyr Lys Gly Ile Lys Ala Asp Gly Gly Lys Val Asp Gln
1               5                   10                  15

Ala Lys Gln Leu Ala Ala Lys Thr Ala Lys Asp Ile Glu Ala Cys Gln
            20                  25                  30

Lys Gln Thr Gln Gln Leu Ala Glu Tyr Ile Glu Gly Ser Asp Trp Glu
        35                  40                  45

Gly Gln Phe Ala Asn Lys Val Lys Asp Val Leu Leu Ile Met Ala Lys
    50                  55                  60

Phe Gln Glu Glu Leu Val Gln Pro Met Ala Asp His Gln Lys Ala Ile
65                  70                  75                  80

Asp Asn Leu Ser Gln Asn Leu Ala Lys Tyr Asp Thr Leu Ser Ile Lys
                85                  90                  95

Gln Gly Leu Asp Arg Val Asn Pro Ala Ser Gly Gly Ser Met Ala
            100                 105                 110
```

```
Met Ile Lys Met Ser Pro Glu Glu Ile Arg Ala Lys Ser Gln Ser Tyr
        115             120             125

Gly Gln Gly Ser Asp Gln Ile Arg Gln Ile Leu Ser Asp Leu Thr Arg
    130             135             140

Ala Gln Gly Glu Ile Ala Ala Asn Trp Glu Gly Gln Ala Phe Ser Arg
145             150             155             160

Phe Glu Glu Gln Phe Gln Gln Leu Ser Pro Lys Val Glu Lys Phe Ala
                165             170             175

Gln Leu Leu Glu Glu Ile Lys Gln Gln Leu Asn Ser Thr Ala Asp Ala
            180             185             190

Val Gln Glu Gln Asp Gln Gln Leu Ser Asn Asn Phe Gly Leu Gln
    195             200             205
```

PURIFICATION OF *STAPHYLOCOCCUS AUREUS* TYPE 8 CAPSULAR SACCHARIDES

CROSS REFERENCE TO RELATED APPLICATIONS

This application is a Divisional of U.S. patent application Ser. No. 13/504,920, with an international filing date of Nov. 1, 2010; which is a National Phase of International Patent Application No. PCT/IB2010/054934, filed Nov. 1, 2010; which claims the benefit of U.S. Provisional Patent Application No. 61/256,905, filed Oct. 30, 2009, all of which are incorporated herein by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 22300211151SEQLISTING.TXT, date recorded: May 14, 2015, size: 150 KB).

TECHNICAL FIELD

This invention is in the field of purifying bacterial capsular polysaccharides, particularly those of *Staphylococcus aureus* type 5 and type 8, and particularly for use in the preparation of vaccines.

BACKGROUND ART

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 96].

Another bacterium for which conjugate vaccines have been described is *Staphylococcus aureus* (*S. aureus*). Various polysaccharides have been isolated from *S. aureus* for use in glycoconjugates. Two polysaccharides of particular interest are the type 5 and type 8 capsular polysaccharides. Approximately 60% of human *S. aureus* strains are type 8 and approximately 30% are type 5. Much of the work on type 5 and type 8 conjugates has been performed by Fattom et al., and is described in documents such as references 1 to 9.

The starting point for polysaccharide-based vaccines is the polysaccharide itself, and this is generally purified from the target bacterium. Fattom et al. have developed a complex process for purification of the type 5 and type 8 capsular polysaccharides that is described in detail in reference 1, and involves the following key steps after bacterial culture: suspension of bacterial cells in buffer, treatment with lysostaphin, treatment with DNase and RNase, centrifugation, dialysis against buffer, treatment with protease, further dialysis, filtration, addition of ethanol to 25% with calcium chloride to precipitate contaminants; further addition of ethanol to 75% to precipitate the polysaccharide; collection and drying of the precipitate; anion exchange chromatography; dialysis; lyophilisation; size exclusion chromatography; dialysis and final lyophilisation.

The Fattom process involves the use of lysostaphin to lyse the bacterial cell walls and thereby release capsular polysaccharide. However, this step is time-consuming and makes the process difficult to scale-up to an industrial setting. It also increases the overall cost and complexity of the process. Other researchers have attempted to omit this step and develop a simpler, more efficient method of purifying the polysaccharide. For example, reference [10] describes an alternative process that involves autoclaving *S. aureus* cells, ultrafiltration of the polysaccharide-containing supernatant, concentration, lyophilisation, treatment with sodium metaperiodate, further ultrafiltration, diafiltration, high performance size exclusion liquid chromatography, dialysis and freeze-drying. The authors suggest that this method provides a good yield and is suitable for large scale production of polysaccharide. In this method, the lysostaphin treatment is replaced by autoclaving to release capsular polysaccharide. The method was further developed in reference [11]. An important step in these alternative methods is the treatment with sodium metaperiodate. This step is carried out to remove teichoic acid contamination of the capsular polysaccharide. However, once again this step increases the duration, complexity and overall cost of the process. Reference [12] describes a similar process that again involves autoclaving to release capsular polysaccharide and treatment with sodium metaperiodate to remove teichoic acid. In contrast, most other groups use processes that retain lysostaphin treatment (see, for example, references 13, 14, 15, 16, 17 and 18), sometimes including treatment with sodium metaperiodate (e.g. in references 13 and 14).

The above methods are complex and may leave contamination in the resultant polysaccharide. There is thus a need for further and improved processes for purifying *S. aureus* type 5 and type 8 capsular polysaccharides, and particularly for less complex processes that result in less contamination.

DISCLOSURE OF THE INVENTION

The invention is based on a purification process in which the polysaccharide is initially released from the bacterial cells by treatment with an acid. This step removes the need for lysostaphin treatment and can be used as an alternative to autoclaving, as in the above processes. The inventors have found that the process results in a purified polysaccharide with low teichoic acid contamination. This means that it is not necessary to treat the polysaccharide with sodium metaperiodate. The purified polysaccharide also has low peptidoglycan contamination, making it particularly suitable for medical uses. The inventors' process can be quick and simple because laborious steps in previous processes are not necessary.

The invention provides a method for releasing capsular polysaccharide from *S. aureus* type 5 or type 8 cells, comprising the step of treating the cells with acid. The invention further provides a process for purifying capsular polysaccharide from *S. aureus* type 5 or type 8 cells comprising this method. Other processing steps may be included in the process, such as enzymatic treatment, e.g. to remove nucleic acid, protein and/or peptidoglycan contaminants; diafiltration, e.g. to remove low molecular weight contaminants; anion exchange chromatography, e.g. to remove residual protein; and concentration.

Accordingly, the invention provides a process for purifying *S. aureus* type 5 or type 8 capsular polysaccharide, comprising the step of releasing the polysaccharide from *S. aureus* type 5 or type 8 cells by treating the cells with acid. Similarly, the invention provides, in a process for purifying S. aureus type 5 or type 8 capsular polysaccharide, the improvement consisting of the use of acid treatment of S. aureus type 5 or type 8 cells to release the polysaccharide from the cells. Release by acid treatment removes the need for lysostaphin treatment or autoclaving to release the polysaccharide.

The invention also provides a process for purifying S. aureus type 5 or type 8 capsular polysaccharide, wherein the process does not involve a step of lysostaphin treatment. Similarly, the invention provides a process for purifying S. aureus type 5 or type 8 capsular polysaccharide, wherein the process does not involve a step of sodium metaperiodate treatment. Typically, the process does not involve one or both of these steps.

The invention also provides a process for purifying S. aureus type 5 or type 8 capsular polysaccharide, wherein the process provides a composition comprising the polysaccharide and a level of peptidoglycan contamination that is less than 5% (e.g. ≤4%, ≤3%, ≤2%, ≤1%, etc.) by weight peptidoglycan relative to the total weight of the polysaccharide. Typically, the composition comprises less than 4%, particularly less than 3%, by weight peptidoglycan. The inventors have found that levels of about 2% or even about 1% can be obtained using the methods of the invention. The inventors have found that compositions with this level of peptidoglycan are useful in vaccine manufacture. In contrast, reference 17 teaches that levels above 5% should be used for this purpose. The level of peptidoglycan contamination may be measured using the methods described herein.

Similarly, the invention provides a process for purifying S. aureus type 5 or type 8 capsular polysaccharide, wherein the process provides a composition comprising the polysaccharide and a level of protein contamination that is less than 5% (e.g. ≤4%, ≤3%, ≤2%, ≤1%, ≤0.5%, etc.) by weight protein relative to the total weight of the polysaccharide. Typically, the composition comprises less than 3%, particularly about 2.4%, by weight protein. The level of protein contamination may be measured using a MicroBCA assay (Pierce).

The invention also provides a process for purifying S. aureus type 5 or type 8 capsular polysaccharide, wherein the process provides a composition comprising the polysaccharide and a level of nucleic acid contamination that is less than 1% (e.g. ≤0.75%, ≤0.50%, ≤0.25%, ≤0.10%, ≤0.01%, etc.) by weight nucleic acid relative to the total weight of the polysaccharide. Typically, the composition comprises less than 0.25%, particularly about 0.09%, by weight nucleic acid. The level of nucleic acid contamination may be measured by absorption at 260 nm in a spectrophotometer.

The invention also provides a process for purifying S. aureus type 5 or type 8 capsular polysaccharide, wherein (a) the level of peptidoglycan acid contamination is less than 5% (as described above); (b) the level of protein contamination is less than 5% (as described above); (c) the level of nucleic acid contamination that is less than 1% (as described above).

The invention also provides a composition comprising a S. aureus type 5 or type 8 capsular polysaccharide, obtainable by any of the processes of the invention.

In particular, the invention provides a composition comprising S. aureus type 5 or type 8 capsular polysaccharide, wherein the composition comprises a level of peptidoglycan contamination that is less than 5% (e.g. ≤4%, ≤3%, ≤2%, ≤1%, etc.) by weight peptidoglycan relative to the total weight of the polysaccharide. Typically, the composition comprises less than 3%, particularly less than 2%, by weight peptidoglycan. Compositions with levels of about 2% or even about 1% are specifically provided by the invention.

Similarly, the invention provides a composition comprising S. aureus type 5 or type 8 capsular polysaccharide, wherein the composition comprises a level of protein contamination that is less than 5% (e.g. ≤4%, ≤3%, ≤2%, ≤1%, ≤0.5%, etc.) by weight protein relative to the total weight of the polysaccharide. Typically, the composition comprises less than 3%, particularly about 2.4%, by weight protein.

The invention also provides a composition comprising S. aureus type 5 or type 8 capsular polysaccharide, wherein the composition comprises a level of nucleic acid contamination that is less than 1% (e.g. ≤0.75%, ≤0.50%, ≤0.25%, ≤0.10%, ≤0.01%, etc.) by weight nucleic acid relative to the total weight of the polysaccharide. Typically, the composition comprises less than 0.25%, particularly about 0.09%, by weight nucleic acid.

The invention also provides a composition comprising S. aureus type 5 or type 8 capsular polysaccharide, wherein a) a level of peptidoglycan acid contamination is less than 5% (as described above); (b) the level of protein contamination is less than 5% (as described above); (c) the level of nucleic acid contamination that is less than 1% (as described above).

The Capsular Polysaccharide

The invention is based on the capsular polysaccharides of S. aureus type 5 and type 8. The structures of type 5 and type 8 capsular polysaccharides were described in references 19 and 20 as:

Type 5
→4)-β-D-ManNAcA(3OAc)-(1→4)-α-L-FucNAc (1→3)-β-D-FucNAc-(1→

Type 8
→3)-β-D-ManNAcA(4OAc)-(1→3)-α-L-FucNAc (1→3)-β-D-FucNAc-(1→.

Recent NMR spectroscopy data [21] has led to a revision of these structures to:

Type 5
→4)-β-D-ManNAcA-(1→4)-α-L-FucNAc(3OAc)- (1→3)-β-D-FucNAc-(1→

Type 8
→3)-β-D-ManNAcA(4OAc)-(1→3)-α-L-FucNAc (1→3)-α-D-FucNAc(1→.

After release from the S. aureus type 5 or type 8 cells, the polysaccharide may be chemically modified relative to the capsular polysaccharide as found in nature. For example, the polysaccharide may be de-O-acetylated (partially or fully), de-N-acetylated (partially or fully), N-propionated (partially or fully), etc. De-acetylation may occur before, during or after other processing steps, but typically occurs before any conjugation step. Depending on the particular polysaccharide, de-acetylation may or may not affect immunogenicity e.g. the NeisVac-C™ vaccine uses a de-O-acetylated polysaccharide, whereas Menjugate™ is acetylated, but both vaccines are effective. The effect of de-acetylation etc. can be assessed by routine assays. For example, the relevance of O-acetylation on S. aureus type 5 or type 8 capsular polysaccharides is discussed in reference 6. The native polysaccharides are said in this document to have 75% O-acetylation. These polysaccharides induced antibodies to both the polysaccharide backbone and O-acetyl groups. Polysaccharides with 0% O-acetylation still elicited antibodies to the polysaccharide backbone. Both types of antibody were opsonic against S. aureus strains that varied in their O-acetyl content. Accordingly, the type 5 or type 8 capsular polysaccharides used in the present invention may have between 0 and 100% O-acetylation. For example, the degree of O-acetylation of the type 5 capsular polysaccharide may be 10-100%, 10-100%, 20-100%, 30-100%, 40-100%, 50-100%, 60-100%, 70-100%, 80-100%, 90-100%, 50-90%, 60-90%, 70-90% or 80-90%. Alternatively, 0% O-acetylated type 5 capsular polysaccharide may be used. Similarly, the degree of O-acetylation of the type 8 capsular polysaccharide may be 10-100%, 10-100%, 20-100%, 30-100%, 40-100%, 50-100%, 60-100%, 70-100%, 80-100%, 90-100%, 50-90%, 60-90%, 70-90% or 80-90%. Alternatively, 0% O-acetylated type 8 capsular polysaccharide may be used. In one embodiment, the degree of O-acetylation of the type 5 and type 8 capsular polysaccharides may be 10-100%, 20-100%, 30-100%, 40-100%, 50-100%, 60-100%, 70-100%, 80-100%, 90-100%, 50-90, 60-90%, 70-90% or 80-90%. In other embodiments, 0% O-acetylated type 5 and type 8 capsular polysaccharides are used. The degree of N-acetylation of the type 5 capsular polysaccharide used in the invention may be 0-100%, 50-100%, 75-100%, 80-100%, 90-100%, or 95-100%. Typically, the degree of N-acetylation of the type 5 capsular polysaccharide is 100%. Similarly, the degree of N-acetylation of the type 8 capsular polysaccharide used in the invention may be 0-100%, 50-100%, 75-100%, 80-100%, 90-100%, or 95-100%. Typically, the degree of N-acetylation of the type 8 capsular polysaccharide is 100%. In one embodiment, the degree of N-acetylation of the type 5 and type 8 capsular polysaccharides may be 0-100%, 50-100%, 75-100%, 80-100%, 90-100%, or 95-100%. Typically, the degree of N-acetylation of the type 5 and type 8 capsular polysaccharides are 100%.

The degree of O-acetylation of the polysaccharide can be determined by any method known in the art, for example, by proton NMR (e.g. as described in references 22, 23, 24 or 25). A further method is described in reference 26. Similar methods may be used to determine the degree of N-acetylation of the polysaccharide. O-acetyl groups may be removed by hydrolysis, for example by treatment with a base such as anhydrous hydrazine [27] or NaOH [6]. Similar methods may be used to remove N-acetyl groups. To maintain high levels of O-acetylation on type 5 and/or 8 capsular polysaccharides, treatments that lead to hydrolysis of the O-acetyl groups are minimised, e.g. treatments at extremes of pH.

Starting Material

The process of the invention starts with *S. aureus* type 5 or type 8 cells. Typically, the cells are grown by fermentation prior to release of capsular polysaccharide. Suitable methods of cultivating *S. aureus* type 5 or type 8 cells are well known to the skilled person and are disclosed, for example, in references 1 to 21 and the references cited therein. After cell growth, the cells are usually deactivated. A suitable method for deactivation is treatment with phenol:ethanol, e.g. as described in reference 1.

The cells may be centrifuged prior to release of capsular polysaccharide. The process may therefore start with the cells in the form of a wet cell paste. Typically, however, the cells are resuspended in an aqueous medium that is suitable for the next step in the process, e.g. in a buffer or in distilled water. The cells may be washed with this medium prior to re-suspension. In another embodiment, the cells may be treated in suspension in their original culture medium. Alternatively, the cells are treated in a dried form.

Acid Treatment

In the method of the invention, *S. aureus* type 5 or type 8 cells are treated with acid. This step results in release of capsular polysaccharide from the cells. In contrast, previous methods have used lysostaphin treatment or autoclaving to release the polysaccharide. The acid treatment of the invention is preferably carried out using a mild acid, e.g. acetic acid, to minimise damage to the polysaccharide. The skilled person would be capable of identifying suitable acids and conditions (e.g. of concentration, temperature and/or time) for release of the polysaccharide. For example, the inventors have found that treatment of cells suspended at about 0.5 mg/ml in distilled water with 1% acetic acid (v/v) at 100° C. for 2 hours is suitable. Treatment with other acids, e.g. trifluoroacetic or other organic acids, may also be suitable.

The efficacy of different acid treatments may be tested using routine methods. For example, after acid treatment, the cells may be isolated and treated using known methods of *S. aureus* type 5 or type 8 capsular polysaccharide release (e.g. the lysostaphin-based method of reference 1) to see if additional capsular polysaccharide can be released. If additional capsular polysaccharide is released, then the acid treatment conditions may be altered so that a greater proportion of the capsular saccharide is released during acid treatment. In this way, it is possible to optimise the acid treatment conditions so that an optimal amount of capsular saccharide is released. For example, the inventors have found that after treatment of cells suspended at about 0.5 mg/ml in distilled water with 1% acetic acid (v/v) at 100° C. for 2 hours, very little additional capsular saccharide is releasable from the cells by subsequent lysostaphin treatment.

The inventors have found that after acid treatment, the degree of O-acetylation of the type 5 capsular polysaccharide may be between 60-100%. In particular, the degree of O-acetylation may be between the 65-95%, particularly 70-90%. Typically, the degree of O-acetylation is between 75-85%, e.g. about 80%. Similar values may be obtained for the type 8 capsular saccharide. If desired, the degree of O-acetylation of the capsular saccharide may then be altered by further processing steps as discussed above.

After acid treatment, the reaction mixture is typically neutralised. This may be achieved by the addition of a base, e.g. NaOH. The cells may be centrifuged and the polysaccharide-containing supernatant collected for storage and/or additional processing.

Enzymatic Treatment

The polysaccharide obtained after acid treatment may be impure and contaminated with bacterial nucleic acids and proteins. These contaminants may be removed by enzymatic treatment. For example, RNA may be removed by treatment with RNase, DNA with DNase and protein with protease (e.g. pronase). The skilled person would be capable of identifying suitable enzymes and conditions for removal of the contaminants. For example, the inventors have found that treatment of polysaccharide-containing supernatant with 50 µg/ml each of DNase and RNase at 37° C. for 6-8 hours is suitable. Other suitable conditions are disclosed in the literature, e.g. in reference 1.

The polysaccharide obtained after acid treatment may also or alternatively be contaminated with peptidoglycan. This contaminant may also be removed by enzymatic treatment. The inventors have found that treatment with mutanolysin is effective at removing peptidoglycan contamination. The skilled person would be capable of identifying suitable conditions for removal of the peptidoglycan with mutanolysin. For example, the inventors have found that treatment of polysaccharide-containing supernatant with 180 U/ml each of mutanolysin at 37° C. for 16 hours is suitable. After treatment, the suspension may be clarified by centrifugation and the polysaccharide-containing supernatant collected for storage and/or additional processing.

Diafiltration

The process of the invention may involve a step of diafiltration. This step is typically performed after the acid treatment and/or enzymatic treatment discussed above. The inventors have found that a diafiltration step, particularly by tangential flow filtration, is particularly effective for removing impurities from the polysaccharide. The impurities are typically low molecular weight contaminants like teichoic and/or peptidoglycan fragments. The tangential flow filtration is suitably carried out against 1M NaCl (e.g. against about 10 volumes) and then NaPi 10 mM pH 7.2 buffer (e.g. against another 10 volumes). The filtration membrane should thus be one that allows passage of small molecular weight contaminants while retaining the capsular polysaccharide. A cut-off in the range 10 kDa-30 kDa is typical. The inventors have found that tangential flow filtration using a 30 kDa cut-off membrane is particularly suitable for large-scale processes.

At least 5 cycles of tangential flow diafiltration are usually performed e.g. 6, 7, 8, 9, 10, 11 or more.

The polysaccharide-containing retentate from the diafiltration is collected for storage and/or additional processing.

Anion Exchange Chromatography

The polysaccharide may be further purified by a step of anion exchange chromatography. The inventors have found that anion exchange chromatography is particularly effective at removing residual protein and nucleic acid contamination, while maintaining a good yield of the polysaccharide.

The anion exchange chromatography step may be performed after the acid treatment, enzymatic treatment and/or diafiltration steps discussed above.

The anion exchange chromatography may be carried out using any suitable anionic exchange matrix. Commonly used anion exchange matrices are resins such as Q-resins (based on quaternary amines) and DEAE resins (based on diethylaminoethane). The inventors have found that DEAE-resins (e.g. a DEAE-Sepharose™ Fast Flow resin (GE Healthcare)) are particularly suitable, although other resins may be used.

Appropriate starting buffers and mobile phase buffers for the anion exchange chromatography can also be determined by routine experiments without undue burden. Typical buffers for use in anion exchange chromatography include N-methyl piperazine, piperazine, L-histidine, bis-Tris, bis-Tris propane, triethanolamine, Tris, N-methyl-diethanolamine, diethanolamine, 1,3-diaminopropane, ethanolamine, piperidine, sodium chloride and phosphate buffers. The inventors have found that phosphate buffers, e.g. a sodium phosphate buffer, are suitable as the starting buffer for the anion exchange chromatography. The buffer may be at any suitable concentration. For example, 10 mM sodium phosphate has been found to be suitable. Material bound to the anionic exchange resin may be eluted with a suitable buffer. The inventors have found that a gradient of NaCl 1M is suitable.

Eluate fractions containing polysaccharide may be determined by measuring UV absorption at 215 nm. Fractions containing polysaccharide, usually combined together, are collected for storage and/or additional processing.

The anion exchange chromatography step may be repeated, e.g. 1, 2, 3, 4 or 5 times. Typically the anion exchange chromatography step is carried out once.

Gel Filtration

The process of the invention may involve one or more step(s) of gel filtration. This gel filtration is used to select polysaccharide molecules of a particular length and to further reduce contamination, particularly by proteins. However, the inventors have found that contrary to previous methods like those of references 1 to 9, a gel filtration step is not required to obtain polysaccharide of high purity. Accordingly, this step may be omitted from the processes of the invention. The omission of this step is advantageous because it simplifies the process and reduces the overall cost.

When present, the gel filtration step(s) may be performed after the acid treatment, enzymatic treatment, diafiltration and/or anion exchange chromatography steps discussed above. Typically, any gel filtration step(s) are carried out after the anion exchange chromatography step discussed above.

The gel filtration step(s) may be carried out using any suitable gel filtration matrix. Commonly used gel filtration matrices are based on dextran gels, agarose gels, polyacrylamide gels, polyacryloylmorpholine gels, and polystyrene gels etc. Cross-linked dextran gels and mixed polyacrylamide/agarose gels may also be used. The inventors have found that dextran gels (e.g. a Sephacryl™ S300 gel (GE Healthcare)) are particularly suitable, although other gels may be used.

Appropriate mobile phase buffers for the gel filtration can be determined by routine experiments without undue burden. Typical buffers for use in gel filtration include N-methyl piperazine, piperazine, L-histidine, bis-Tris, bis-Tris propane, triethanolamine, Tris, N-methyl-diethanolamine, diethanolamine, 1,3-diaminopropane, ethanolamine, piperidine, sodium chloride and phosphate buffers. For example, sodium chloride buffers may be suitable. The buffer may be at any suitable concentration. For example, 50 mM sodium chloride may be used for the mobile phase.

Eluate fractions containing polysaccharide may be determined by measuring UV absorption at 215 nm. Fractions containing polysaccharide, usually combined together, are collected for storage and/or additional processing.

Concentration

In addition to, or instead of, the one or more step(s) of gel filtration, the process of the invention may involve one or more steps of concentrating the polysaccharide. This concentration is useful for obtaining a sample of the correct concentration for any subsequent conjugation of the polysaccharide to a carrier molecule, as described below. However, the inventors have found that this concentration step is not required to obtain polysaccharide of high purity. Accordingly, this step may be omitted from the processes of the invention.

When present, the concentration step(s) may be performed after the acid treatment, enzymatic treatment, diafiltration, anion exchange chromatography and/or gel filtration steps discussed above. Typically, any concentration step(s) are carried out after the anion exchange chromatography step discussed above. If used in addition to the gel filtration step(s) discussed above, the concentration step(s) may be carried out before or after the gel filtration step(s) discussed above. However, typically, concentration step(s) are used instead of gel filtration step(s).

The concentration step(s) may be carried out by any suitable method. For example, the inventors have found that the concentration step(s) may be diafiltration step(s) as described above, for example tangential flow filtration using a 30 kDa cut-off membrane. For example, a Hydrosart™ (Sartorius) 30 kDa cut-off membrane (with a 200 cm$^2$ membrane area) may be used.

The concentrated polysaccharide sample is collected for storage and/or additional processing.

Further Treatment of the Capsular Polysaccharide

After purification, the polysaccharide may be further treated to remove contaminants. This is particularly important in situations where even minor contamination is not acceptable (e.g. for human vaccine production).

The molecular mass of the purified S. aureus type 5 or type 8 capsular polysaccharide can be measured by gel filtration relative to pullulan standards, such as those available from Polymer Standard Service [28]. Typically, the purified polysaccharide is a mixture of polysaccharides with masses within a range of values. For the type 5 capsular polysaccharide, the molecular mass of the purified polysaccharide typically is between 2-3500 kDa, e.g. between 10-2000 kDa, particularly between 20-1000 kDa and more particularly between 100-600 kDa. Similarly, for the type 8 capsular polysaccharide, the molecular mass of the purified polysaccharide may be between 2-3500 kDa, e.g. between 10-2000 kDa, particularly between 20-1000 kDa and more particularly between 100-600 kDa.

The purified polysaccharide may be depolymerised to form an oligosaccharide. Oligosaccharides may be preferred for use in vaccines. Depolymerisation to oligosaccharide may occur before or after any of the steps mentioned above. Typically, depolymerisation takes place after the anion exchange chromatography described above. If the polysaccharide is concentrated after this chromatography, then depolymerisation typically takes place after this concentration. Where the composition of the invention includes a depolymerised polysaccharide, it is preferred that depolymerisation precedes any conjugation.

Full-length polysaccharides may be depolymerised to give shorter fragments for use in the invention by various methods. Preferably, the method described in reference 29 is used. Alternatively, other methods for depolymerisation of the polysaccharide may be used. For example, the polysaccharide may be heated or subjected to microfluidisation [30] or sonic radiation [3]. Alternatively, depolymerisation by oxidation-reduction [31] or ozonolysis [32] may be used.

Oligosaccharides can be identified by chromatography, e.g. size exclusion chromatography. The products may be sized in order to remove short-length oligosaccharides. This can be achieved in various ways, such as gel filtration. Specific molecular masses can be measured by gel filtration relative to pullulan standards, such as those available from Polymer Standard Service [33].

If N-acetyl groups in the native capsular polysaccharide have been de-N-acetylated then the processes of the invention may include a step of re-N-acetylation. Controlled re-N-acetylation can conveniently be performed using a reagent such as acetic anhydride $(CH_3CO)_2O$ e.g. in 5% ammonium bicarbonate [34].

Further rounds of filtration, e.g. sterile filtration, can also be performed.

These additional steps can generally be performed at room temperature.

Storage

The S. aureus type 5 or type 8 capsular polysaccharide preparation may be lyophilised, e.g. by freeze-drying under vacuum, or frozen in solution (e.g. as the eluate from the final concentration step, if included) for storage at any stage during the purification process. Accordingly, it is not necessary for the preparation to be transferred immediately from one step of the process to another. For example, if the polysaccharide preparation is to be purified by diafiltration, then it may be lyophilised or frozen in solution prior to this purification. Similarly, the polysaccharide may be lyophilised or frozen in solution prior to the anion exchange chromatography step. If the polysaccharide preparation is to be purified by gel filtration, then it may be lyophilised or frozen in solution prior to this step. Similarly, if the polysaccharide preparation is to be concentrated, then it may be lyophilised or frozen in solution prior to this step. The lyophilised preparation is reconstituted in an appropriate solution prior to further treatment. Similarly, the frozen solution is defrosted prior to further treatment.

The purified polysaccharide obtained by the process of the invention may be processed for storage in any suitable way. For example, the polysaccharide may be lyophilised as described above. Alternatively, the polysaccharide may be stored in aqueous solution, typically at low temperature, e.g. at $-20°$ C. Conveniently, the polysaccharide may be stored as the eluate from the anion exchange chromatography, gel filtration or concentration steps.

Conjugation

The final purified capsular polysaccharide of the invention can be used as an antigen without further modification e.g. for use in in vitro diagnostic assays, for use in immunisation, etc.

For immunisation purposes, however, it is preferred to conjugate the polysaccharide to a carrier molecule, such as a protein. In general, covalent conjugation of polysaccharides to carriers enhances the immunogenicity of polysaccharides as it converts them from T-independent antigens to T-dependent antigens, thus allowing priming for immunological memory. Conjugation is particularly useful for paediatric vaccines [e.g. ref. 35] and is a well known technique [e.g. reviewed in refs. 36 to 44]. Thus the processes of the invention may include the further step of conjugating the purified polysaccharide to a carrier molecule.

Conjugation of S. aureus type 5 and type 8 capsular polysaccharides has been widely reported e.g. see references 1 to 9. The typical process used in the literature for conjugation involves thiolation of a purified polysaccharide using cystamine. The reaction relies on the presence of carboxylate groups in the capsular polysaccharide. These groups react with cystamine in the presence of a carbodiimide, e.g. EDAC. The derivatised polysaccharide is then conjugated to a carrier protein such as the Pseudomononas aeruginosa endotoxin A (ETA), typically via a linker [2]. Conjugate vaccines prepared in this manner have been shown to be safe and immunogenic in humans [5]. Other researchers have carried out conjugation of purified type 5 and type 8 capsular polysaccharides by reductive amination [45 and 12]; glutaradehyde coupling [45]; or reaction of hydroxyl groups on the polysaccharides with cyanylating agents like CDAP [46] or cyanuric trichloride [11]. Preferably, the process described in reference 29 is used.

Preferred carrier proteins are bacterial toxins, such as diphtheria or tetanus toxins, or toxoids or mutants thereof. The inventors have found that the CRM197 diphtheria toxin mutant [47] is suitable. Pseudomonas aeruginosa exotoxin A (ETA) and its non-toxic mutant recombinant exoprotein A (rEPA) have been used as carrier proteins for S. aureus type 5 or type 8 capsular polysaccharides ([1] and [2]). S. aureus α-haemolysin (α-toxin) ([45] and [48]), ovalbumin [11] and human serum albumin [12] have also been used. These carriers may be used in the present invention.

Other suitable carrier proteins include the N. meningitidis outer membrane protein complex [49], synthetic peptides [50,51], heat shock proteins [52,53], pertussis proteins [54, 55], cytokines [56], lymphokines [56], hormones [56], growth factors [56], human serum albumin (typically recombinant), artificial proteins comprising multiple human CD4$^+$ T cell epitopes from various pathogen-derived antigens [57]

such as N19 [58], protein D from *H. influenzae* [59-61], pneumococcal surface protein PspA [62], pneumolysin [63] or its non-toxic derivatives [64], iron-uptake proteins [65], toxin A or B from *C. difficile* [66], a GBS protein [67], a GAS protein [68] etc.

Other suitable carrier proteins include *S. aureus* protein antigens, for example the *S. aureus* protein antigens set out below.

Attachment to the carrier is preferably via a —NH$_2$ group e.g. in the side chain of a lysine residue in a carrier protein, or of an arginine residue. Attachment may also be via a —SH group e.g. in the side chain of a cysteine residue.

It is possible to use more than one carrier protein e.g. to reduce the risk of carrier suppression. Thus different carrier proteins can be used for the type 5 and type 8 capsular polysaccharides, e.g. type 5 polysaccharide might be conjugated to CRM197 while type 8 polysaccharide might be conjugated to rEPA. It is also possible to use more than one carrier protein for a particular polysaccharide antigen e.g. type 5 polysaccharide might be in two groups, with one group conjugated to CRM197 and the other conjugated to rEPA. Typically, however, the same carrier protein is used for all polysaccharides.

A single carrier protein might carry more than one polysaccharide antigen [69,70]. For example, a single carrier protein might have conjugated to it type 5 and type 8 capsular polysaccharides. To achieve this goal, different polysaccharides can be mixed prior to the conjugation process. Typically, however, there are separate conjugates for each polysaccharide, with the different polysaccharides being mixed after conjugation. The separate conjugates may be based on the same carrier.

Conjugates with a polysaccharide:protein ratio (w/w) of between 1:20 (i.e. excess protein) and 20:1 (i.e. excess polysaccharide) are typically used. Ratios of 1:10 to 1:1 are preferred, particularly ratios between 1:5 and 1:2 and, most preferably, about 1:3. In contrast, type 5 and type 8 capsular polysaccharide conjugates used in the literature tend to have higher ratios, e.g. between 0.73 and 1.08 in references 1, 2 and 3. In particular embodiments of the invention, the polysaccharide:protein ratio (w/w) for type 5 capsular polysaccharide conjugate is between 1:10 and 1:2; and/or the polysaccharide:protein ratio (w/w) for type 8 capsular polysaccharide conjugate is between 1:5 and 7:10.

Conjugates may be used in conjunction with free carrier [71]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated polysaccharides can be separated. There are many suitable methods, including hydrophobic chromatography, tangential ultrafiltration, diafiltration etc. [see also refs. 72 & 73, etc.].

Combinations of Conjugates and Other Antigens

Polysaccharides prepared by the methods of the invention (in particular after conjugation as described above) can be mixed e.g. with each other and/or with other antigens. Thus the processes of the invention may include the further step of mixing the polysaccharide with one or more further antigens. The invention therefore provides a composition comprising a polysaccharide prepared by the method of the invention and one or more further antigens. The composition is typically an immunogenic composition.

The further antigen(s) may comprise further polysaccharides prepared by the method of the invention, and so the invention provides a composition comprising more than one polysaccharide of the invention. In particular, the present invention provides a composition comprising a type 5 capsular polysaccharide of the invention and a type 8 capsular polysaccharide of the invention. Alternatively, the further antigen(s) may be type 5 or type 8 capsular polysaccharides prepared by methods other than those of the invention, e.g. the methods of references 1 to 18 above. Accordingly, the invention provides a composition comprising a type 5 capsular polysaccharide and a type 8 capsular polysaccharide, wherein one of the polysaccharides (the type 5 polysaccharide or the type 8 polysaccharide) is a polysaccharide of the invention and the other polysaccharide is not a polysaccharide of the invention.

Where multiple different *S. aureus* conjugates are mixed then these may include different types of conjugate from the same *S. aureus* serotype and/or conjugates from different *S. aureus* serotypes. For example, the conjugates may be from *S. aureus* type 5 and type 8. The composition will be produced by preparing separate conjugates (e.g. a different conjugate for each serotype) and then combining the conjugates.

The further antigen(s) may comprise other *S. aureus* antigens, including the saccharide and protein antigens set out below.

The further antigen(s) may comprise antigens from non-*S. aureus* pathogens. Thus the compositions of the invention may further comprise one or more non-*S. aureus* antigens, including additional bacterial, viral or parasitic antigens. These may be selected from the following:

a protein antigen from *N. meningitidis* serogroup B, such as those in refs. 74 to 80, with protein '287' (see below) and derivatives (e.g. 'ΔG287') being particularly preferred.

an outer-membrane vesicle (OMV) preparation from *N. meningitidis* serogroup B, such as those disclosed in refs. 81, 82, 83, 84 etc.

a saccharide antigen from *N. meningitidis* serogroup A, C, W135 and/or Y, such as the oligosaccharide disclosed in ref. 85 from serogroup C or the oligosaccharides of ref. 86.

a saccharide antigen from *Streptococcus pneumoniae* [e.g. refs. 87-89; chapters 22 & 23 of ref. 96].

an antigen from hepatitis A virus, such as inactivated virus [e.g. 90, 91; chapter 15 of ref. 96].

an antigen from hepatitis B virus, such as the surface and/or core antigens [e.g. 91,92; chapter 16 of ref. 96].

an antigen from hepatitis C virus [e.g. 93].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 94 & 95; chapter 21 of ref. 96].

a diphtheria antigen, such as a diphtheria toxoid [e.g. chapter 13 of ref. 96].

a tetanus antigen, such as a tetanus toxoid [e.g. chapter 27 of ref. 96].

a saccharide antigen from *Haemophilus influenzae* B [e.g. chapter 14 of ref. 96]

an antigen from *N. gonorrhoeae* [e.g. 74, 75, 76].

an antigen from *Chlamydia pneumoniae* [e.g. 97, 98, 99, 100, 101, 102, 103].

an antigen from *Chlamydia trachomatis* [e.g. 104].

an antigen from *Porphyromonas gingivalis* [e.g. 105].

polio antigen(s) [e.g. 106, 107; chapter 24 of ref. 96] such as IPV.

rabies antigen(s) [e.g. 108] such as lyophilised inactivated virus [e.g. 109, RabAvert™].

measles, mumps and/or rubella antigens [e.g. chapters 19, 20 and 26 of ref. 96].

influenza antigen(s) [e.g. chapters 17 & 18 of ref. 96], such as the haemagglutinin and/or neuraminidase surface proteins.

an antigen from *Moraxella catarrhalis* [e.g. 110].

an antigen from *Streptococcus pyogenes* (group A *streptococcus*) [e.g. 111, 112, 113].

an antigen from *Streptococcus agalactiae* (group B *streptococcus*) [e.g. 68, 114-116].

an antigen from *S. epidermidis* [e.g. type I, II and/or III capsular polysaccharide obtainable from strains ATCC-31432, SE-360 and SE-10 as described in refs. 117, 118 and 119.

Where a saccharide or carbohydrate antigen is used, it is preferably conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of pertussis toxin by chemical and/or genetic means [95]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens may be adsorbed to an aluminium salt.

One type of preferred composition includes further antigens that affect the immunocompromised, and so the *S. aureus* polysaccharides of the invention can be combined with one or more antigens from the following non-*S. aureus* pathogens: *Streptococcus agalactiae, Staphylococcus epidermis,* influenza virus, *Enterococcus faecalis, Pseudomonas aeruginosa, Legionella pneumophila, Listeria monocytogenes, Neisseria meningitidis,* and parainfluenza virus.

Another type of preferred composition includes further antigens from bacteria associated with nosocomial infections, and so the *S. aureus* polysaccharides of the invention can be combined with one or more antigens from the following non-*S. aureus* pathogens: *Clostridium difficile, Pseudomonas aeruginosa, Candida albicans,* and extraintestinal pathogenic *Escherichia coli.*

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 120 to 128]. Protein components of the compositions of the invention may thus be replaced by nucleic acid (preferably DNA e.g. in the form of a plasmid) that encodes the protein.

In practical terms, there may be an upper limit to the number of antigens included in compositions of the invention. The number of antigens (including *S. aureus* antigens) in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. The number of *S. aureus* antigens in a composition of the invention may be less than 6, less than 5, or less than 4.

Pharmaceutical Compositions and Methods

The invention provides processes for preparing pharmaceutical compositions, comprising the steps of mixing (a) a polysaccharide of the invention (optionally in the form of a conjugate) with (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 129.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be typical to include a sugar alcohol (e.g. mannitol) or a disaccharide (e.g. sucrose or trehalose) e.g. at between 1 mg/ml and 30 mg/ml (e.g. about 25 mg/ml) in the composition.

The pharmaceutical compositions may be packaged into vials or into syringes. The syringes may be supplied with or without needles. A syringe will include a single dose of the composition, whereas a vial may include a single dose or multiple doses.

Aqueous compositions of polysaccharides of the invention are suitable for reconstituting other vaccines from a lyophilised form. Where a composition of the invention is to be used for such extemporaneous reconstitution, the invention provides a process for reconstituting such a lyophilised vaccine, comprising the step of mixing the lyophilised material with an aqueous composition of the invention. The reconstituted material can be used for injection.

S. aureus Antigens

As mentioned above, one or more further *S. aureus* antigens can be included in compositions of the invention. The antigens may be protein or saccharide antigens. *S. aureus* protein antigens may be used as carrier proteins for conjugates of the invention, carrier proteins for other conjugates, or as unconjugated protein antigens. *S. aureus* saccharide antigens may be used as the saccharides for other conjugates or as unconjugated saccharide antigens.

Suitable *S. aureus* saccharide antigens include the exopolysaccharide of *S. aureus*, which is a poly-N-acetylglucosamine (PNAG). This polysaccharide is present in both *S. aureus* and *S. epidermidis* and can be isolated from either source [130,131]. For example, PNAG may be isolated from *S. aureus* strain MN8m [132]. The saccharide antigen may be a polysaccharide having the size that arises during purification of the exopolysaccharide from bacteria, or it may be an polysaccharide achieved by fragmentation of such a polysaccharide e.g. size can vary from over 400 kDa to between 75 and 400 kDa, or between 10 and 75 kDa, or up to 30 repeat units. The saccharide antigen can have various degrees of N-acetylation and, as described in reference 133, the PNAG may be less than 40% N-acetylated (e.g. less than 35, 30, 20, 15, 10 or 5% N-acetylated; deacetylated PNAG is also known as dPNAG). Deacetylated epitopes of PNAG can elicit antibodies that are capable of mediating opsonic killing. The preparation of dPNAG is described in reference 134. The PNAG may or may not be O-succinylated e.g. it may be O-succinylated on fewer less than 25, 20, 15, 10, 5, 2, 1 or 0.1% of residues. The PNAG may be conjugated to a carrier molecule as described above or alternatively unconjugated.

Another suitable *S. aureus* saccharide antigen is the type 336 antigen, which is a β-linked hexosamine with no O-acetylation [135,136]. The type 336 antigen is cross-reactive with antibodies raised against the 336 strain (ATCC 55804). The type 336 antigen may be conjugated to a carrier molecule as described above or alternatively unconjugated.

Suitable *S. aureus* protein antigens include the following *S. aureus* antigens (or antigens comprising immunogenic fragment(s) thereof) [e.g. see references 137-144]: AhpC, AhpF, Autolysin amidase, Autolysin glucosaminidase, Collagen binding protein CAN, EbhB, GehD lipase, Heparin binding protein HBP (17 kDa), Laminin receptor, MAP, MntC (also known as SitC), MRPII, Npase, ORF0594, ORF0657n, ORF0826, PBP4, RAP (RNA III activating protein), Sai-1, SasK, SBI, SdrG, SdrH, SSP-1, SSP-2 and Vitronectin-binding protein.

Further suitable *S. aureus* protein antigens include a clfA antigen; a clfB antigen; a sdrE2 antigen; a sdrC antigen; a sasF antigen, a emp antigen; a sdrD antigen; a spa antigen; a esaC antigen; a esxA antigen; a esxB antigen; a sta006 antigen; a isdC antigen; a Hla antigen; a sta011 antigen; a isdA antigen; a isdB antigen; and a sta073 antigen, as described below. One or more (i.e. 1, 2, 3, 4, 5, 6 or more) of these antigens may be present in a composition of the invention. Of these antigens, the use of one or more (i.e. 1, 2, 3, 4, 5, 6 or more) of a esxA antigen; a esxB antigen; a sta006 antigen; a Hla antigen; a sta011 antigen; and/or a sta073 antigen is specifically envisaged.

For example, a composition of the invention may comprise one of the following combinations of *S. aureus* protein antigens:

(1) A esxA antigen, a esxB antigen, a sta006 antigen and a Hla antigen. The esxA and esxB antigens can usefully be combined as a hybrid polypeptide, as discussed below, e.g. a EsxAB hybrid with a esxB antigen downstream of a esxA antigen. The Hla antigen may be a detoxified mutant e.g. including a H35L mutation.

(2) A esxA antigen, a esxB antigen, a sta006 antigen and a sta011 antigen. The esxA and esxB antigens may be combined as a hybrid polypeptide, as discussed below, e.g. an EsxAB hybrid.

(3) A esxA antigen, a esxB antigen and a sta011 antigen. The esxA and esxB antigens can usefully be combined as a hybrid polypeptide, as discussed below, e.g. a EsxAB hybrid.

(4) A esxA antigen, a esxB antigen, a Hla antigen, a sta006 antigen and a sta011 antigen. The esxA and esxB antigens may be combined as a hybrid polypeptide, as discussed below, e.g. an EsxAB hybrid. The Hla antigen may be a detoxified mutant e.g. including a H35L mutation.

(5) A esxA antigen, a esxB antigen and a Hla antigen. The esxA and esxB antigens can usefully be combined as a hybrid polypeptide, as discussed below, e.g. a EsxAB hybrid. The Hla antigen may be a detoxified mutant e.g. including a H35L mutation.

(6) A Hla antigen, a sta006 antigen and a sta011 antigen. The Hla antigen may be a detoxified mutant e.g. including a H35L mutation.

(7) A esxA antigen and a esxB antigen. The esxA and esxB antigens can usefully be combined as a hybrid polypeptide, as discussed below, e.g. an EsxAB hybrid.

(8) A esxA antigen, a esxB antigen and a sta006 antigen. The esxA and esxB antigens can usefully be combined as a hybrid polypeptide, as discussed below, e.g. a EsxAB hybrid.

(9) A esxA antigen, a esxB antigen, a sta011 antigen and a sta073 antigen. The esxA and esxB antigens may be combined as a hybrid polypeptide, as discussed below, e.g. an EsxAB hybrid.

(10) A sta006 antigen and a sta011 antigen.

Further *Staphylococcus aureus* antigens are disclosed in reference 145.

clfA

The 'clfA' antigen is annotated as 'clumping factor A'. In the NCTC 8325 strain clfA is SAOUHSC_00812 and has amino acid sequence SEQ ID NO: 1 (GI:88194572). In the Newman strain it is nwmn_0756 (GI:151220968).

Useful clfA antigens can elicit an antibody (e.g. when administered to a human) that recognises SEQ ID NO: 1 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more). These clfA proteins include variants of SEQ ID NO: 1. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1 while retaining at least one epitope of SEQ ID NO: 1. The final 368 C-terminal amino acids of SEQ ID NO: 1 can usefully be omitted. The first 39 N-terminal amino acids of SEQ ID NO: 1 can usefully be omitted. Other fragments omit one or more protein domains.

SEQ ID NO: 2 is a useful fragment of SEQ ID NO: 1 ('ClfA$_{40-559}$'). This fragments omits the long repetitive region towards the C-terminal of SEQ ID NO: 1.

clfB

The 'clfB' antigen is annotated as 'clumping factor B'. In the NCTC 8325 strain clfB is SAOUHSC_02963 and has amino acid sequence SEQ ID NO: 3 (GI:88196585). In the Newman strain it is nwmn_2529 (GI:151222741).

Useful clfB antigens can elicit an antibody (e.g. when administered to a human) that recognises SEQ ID NO: 3 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These clfB proteins include variants of SEQ ID NO: 3. Preferred fragments of (b) comprise an epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one epitope of SEQ ID NO: 3. The final 40 C-terminal amino acids of SEQ ID NO: 3 can usefully be omitted. The first 44 N-terminal amino acids of SEQ ID NO: 3 can usefully be omitted. Other fragments omit one or more protein domains. ClfB is naturally a long protein and so the use of fragments is helpful e.g. for purification, handling, fusion, expression, etc.

SEQ ID NO: 4 is a useful fragment of SEQ ID NO: 3 ('ClfB$_{45-552}$'). This fragment includes the most exposed domain of ClfB and is more easily used at an industrial scale. It also reduces the antigen's similarity with human proteins. Other useful fragments, based on a 3-domain model of ClfB, include: ClfB$_{45-360}$ (also known as CLfB-N12; SEQ ID NO: 5); ClfB$_{212-542}$ (also known as CLfB-N23; SEQ ID NO: 6); and ClfB$_{360-542}$ (also known as CLfB-N3; SEQ ID NO: 7).

sdrE2

The 'sdrE2' antigen is annotated as 'Ser-Asp rich fibrinogen/bone sialoprotein-binding protein SdrE'. In the Newman strain sdrE2 is NWMN_0525 and has amino acid sequence SEQ ID NO: 8 (GI:151220737).

Useful sdrE2 antigens can elicit an antibody (e.g. when administered to a human) that recognises SEQ ID NO: 8 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). These sdrE2 proteins include variants of SEQ ID NO: 8. Preferred fragments of (b) comprise an epitope from SEQ ID NO: 8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 8 while retaining at least one epitope of SEQ ID NO: 8. The final 38 C-terminal amino acids of SEQ ID NO: 8 can usefully be omitted. The first 52 N-terminal amino acids of SEQ ID NO: 8 can usefully be omitted. Other fragments omit one or more protein domains. SdrE2 is naturally a long protein and so the use of fragments is very helpful e.g. for purification, handling, fusion, expression, etc.

SEQ ID NO: 9 is a useful fragment of SEQ ID NO: 8 ('SdrE$_{53-632}$'). This fragment includes the most exposed domain of SdrE2 and is more easily used at an industrial scale. It also reduces the antigen's similarity with human proteins.

sdrC

The 'sdrC' antigen is annotated as 'sdrC protein'. In the NCTC 8325 strain sdrC is SAOUHSC_00544 and has amino acid sequence SEQ ID NO: 10 (GI:88194324).

Useful sdrC antigens can elicit an antibody (e.g. when administered to a human) that recognises SEQ ID NO: 10 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). These sdrC proteins include variants of SEQ ID NO: 10. Preferred fragments of (b) comprise an epitope from SEQ ID NO: 10. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 10 while retaining at least one epitope of SEQ ID NO: 10. The final 38 C-terminal amino acids of SEQ ID NO: 10 can usefully be omitted. The first 50 N-terminal amino acids of SEQ ID NO: 10 can usefully be omitted. Other fragments omit one or more protein domains. SdrC is naturally a long protein and so the use of fragments is helpful e.g. for purification, handling, fusion, expression, etc.

SEQ ID NO: 11 is a useful fragment of SEQ ID NO: 10 ('SdrC5$_{1-518}$'). This fragment includes the most exposed domain of SdrC and is more easily used at an industrial scale. It also reduces the antigen's similarity with human proteins.

sasF

The 'sasF' antigen is annotated as 'sasF protein'. In the NCTC 8325 strain sasF is SAOUHSC_02982 and has amino acid sequence SEQ ID NO: 12 (GI:88196601).

Useful sasF antigens can elicit an antibody (e.g. when administered to a human) that recognises SEQ ID NO: 12 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). These sasF proteins include variants of SEQ ID NO: 12. Preferred fragments of (b) comprise an epitope from SEQ ID NO: 12. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 12 while retaining at least one epitope of SEQ ID NO: 12. The final 39 C-terminal amino acids of SEQ ID NO: 12 can usefully be omitted. The first 37 N-terminal amino acids of SEQ ID NO: 12 can usefully be omitted. Other fragments omit one or more protein domains.

emp

The 'emp' antigen is annotated as 'extracellular matrix and plasma binding protein'. In the NCTC 8325 strain emp is SAOUHSC_0.00816 and has amino acid sequence SEQ ID NO: 13 (GI:88194575). In the Newman strain it is nwmn_0758 (GI:151220970).

Useful emp antigens can elicit an antibody (e.g. when administered to a human) that recognises SEQ ID NO: 13 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). These emp proteins include variants of SEQ ID NO: 13. Preferred fragments of (b) comprise an epitope from SEQ ID NO: 13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13 while retaining at least one epitope of SEQ ID NO: 13. The first 26 N-terminal amino acids of SEQ ID NO: 13 can usefully be omitted. Other fragments omit one or more protein domains.

SEQ ID NOs: 14, 15, 16 and 17 are useful fragments of SEQ ID NO: 13 ('Emp$_{35-340}$', 'Emp$_{27-334}$', 'Emp$_{35-334}$' and 'Emp$_{27-147}$', respectively).

sdrD

The 'sdrD' antigen is annotated as 'sdrD protein'. In the NCTC 8325 strain sdrD is SAOUHSC_00545 and has amino acid sequence SEQ ID NO: 18 (GI:88194325).

Useful sdrD antigens can elicit an antibody (e.g. when administered to a human) that recognises SEQ ID NO: 18 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 18; and/or (b) comprising a fragment of at least 'n' consecutive amino acids of SEQ ID NO: 18, wherein 'n' is 7 or more (e.g. 8, 10, 12, 14, 16, 18, 20, 25, 30, 35, 40, 50, 60, 70, 80, 90, 100, 150, 200, 250 or more). These sdrD proteins include variants of SEQ ID NO: 18. Preferred fragments of (b) comprise an epitope from SEQ ID NO: 18. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 18 while retaining at least one epitope of SEQ ID NO: 18. The final 38 C-terminal amino acids of SEQ ID NO: 18 can usefully be omitted. The first 52 N-terminal amino acids of SEQ ID NO: 18 can usefully be omitted. Other fragments omit one or more protein domains. SdrD is naturally a long protein and so the use of fragments is very helpful e.g. for purification, handling, fusion, expression, etc.

SEQ ID NO: 19 is a useful fragment of SEQ ID NO: 18 ('SdrD$_{53-592}$'). This fragment includes the most exposed domain of SdrD and is more easily used at an industrial scale. It also reduces the antigen's similarity with human proteins. Another useful fragment, with the same C-terminus residue, is SdrD$_{394-592}$ (also known as SdrD-N3; SEQ ID NO: 20).

spa

The 'spa' antigen is annotated as 'protein A' or 'SpA'. In the NCTC 8325 strain spa is SAOUHSC_00069 and has amino acid sequence SEQ ID NO: 21 (GI:88193885). In the Newman strain it is nwmn_0055 (GI:151220267). All *S. aureus* strains express the structural gene for spa, a well characterized virulence factor whose cell wall-anchored surface protein product has five highly homologous immunoglobulin binding domains designated E, D, A, B, and C [146]. These domains display ~80% identity at the amino acid level, are 56 to 61 residues in length, and are organized as tandem repeats [147]. SpA is synthesized as a precursor protein with an N-terminal signal peptide and a C-terminal sorting signal [148,149]. Cell wall-anchored spa is displayed in great abundance on the staphylococcal surface [150,151]. Each of its immunoglobulin binding domains is composed of anti-parallel α-helices that assemble into a three helix bundle and can bind the Fc domain of immunoglobulin G (IgG) [152,153], the VH3 heavy chain (Fab) of IgM (i.e. the B cell receptor) [154], the von Willebrand factor at its A1 domain [155] and/or the TNF-α receptor I (TNFRI) [156], which is displayed on surfaces of airway epithelia.

Useful spa antigens can elicit an antibody (e.g. when administered to a human) that recognises SEQ ID NO: 21 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 21; and/or (b) comprising a fragment of at least 'n' consecutive amino acids of SEQ ID NO: 21, wherein 'n' is 7 or more (e.g. 8, 10, 12, 14, 16, 18, 20, 25, 30, 35, 40, 50, 60, 70, 80, 90, 100, 150, 200, 250 or more). These spa proteins include variants of SEQ ID NO: 21. Preferred fragments of (b) comprise an epitope from SEQ ID NO: 21. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 21 while retaining at least one epitope of SEQ ID NO: 21. The final 35 C-terminal amino acids of SEQ ID NO: 21 can usefully be omitted. The first 36 N-terminal amino acids of SEQ ID NO: 21 can usefully be omitted. Other fragments omit one or more protein domains. Reference 157 suggests that individual IgG-binding domains might be useful immunogens, alone or in combination.

SEQ ID NO: 22 is a useful fragment of SEQ ID NO: 21 ('Spa$_{37-325}$'). This fragment contains all the five SpA Ig-binding domains and includes the most exposed domain of SpA. It also reduces the antigen's similarity with human proteins. Other useful fragments may omit 1, 2, 3 or 4 of the natural A, B, C, D and/or E domains. As reported in reference 157, other useful fragments may include only 1, 2, 3 or 4 of the natural A, B, C, D and/or E domains e.g. comprise only the SpA(A) domain but not B to E, or comprise only the SpA(D) domain but not A, B, C or E, etc. Thus a spa antigen useful with the invention may include 1, 2, 3, 4 or 5 IgG-binding domains, but ideally has 4 or fewer. If an antigen includes only one type of spa domain (e.g. only the Spa(A) or SpA(D) domain), it may include more than one copy of this domain e.g. multiple SpA(D) domains in a single polypeptide chain. An individual domain within the antigen may be mutated at 1, 2, 3, 4, 5, 6, 7, 8, 9, 10 or more amino acids relative to SEQ ID NO: 21 (e.g. see ref. 157, disclosing mutations at residues 3 and/or 24 of domain D, at residue 46 and/or 53 of domain A, etc.). Such mutants should not remove the antigen's ability to elicit an antibody that recognises SEQ ID NO: 21, but may remove the antigen's binding to IgG. In certain aspects a spa antigen includes a substitution at (a) one or more amino acid substitution in an IgG Fc binding sub-domain of SpA domain A, B, C, D and/or E that disrupts or decreases binding to IgG Fc, and (b) one or more amino acid substitution in a V$_H$3 binding sub-domain of SpA domain A, B, C, D, and/or E that disrupts or decreases binding to V$_H$3. In certain embodiments, a variant SpA comprises at least or at most 1, 2, 3, 4, 5, 6, 7, 8, 9, 10 or more variant SpA domain D peptides.

esaC

The 'esaC' antigen is annotated as 'esaC'. In the NCTC 8325 strain esaC is SAOUHSC_00264 and has amino acid sequence SEQ ID NO: 23 (GI:88194069).

Useful esaC antigens can elicit an antibody (e.g. when administered to a human) that recognises SEQ ID NO: 23 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100 or more). These esaC proteins include variants of SEQ ID NO: 23. Preferred fragments of (b) comprise an epitope from SEQ ID NO: 23. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 23 while retaining at least one epitope of SEQ ID NO: 23. Other fragments omit one or more protein domains.

esxA

The 'esxA' antigen is annotated as 'protein'. In the NCTC 8325 strain esxA is SAOUHSC_00257 and has amino acid sequence SEQ ID NO: 24 (GI:88194063).

Useful esxA antigens can elicit an antibody (e.g. when administered to a human) that recognises SEQ ID NO: 24 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24; and/or (b) comprising a fragment of at least 'n' consecutive amino acids of SEQ ID NO: 24, wherein 'n' is 7 or more (e.g. 8, 10, 12, 14, 16, 18, 20, 25, 30, 35, 40, 50, 60, 70, 80, 90 or more). These esxA proteins include variants of SEQ ID NO: 24. Preferred fragments of (b) comprise an epitope from SEQ ID NO: 24. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 24 while retaining at least one epitope of SEQ ID NO: 24. Other fragments omit one or more protein domains.

esxB

The 'esxB' antigen is annotated as 'esxB'. In the NCTC 8325 strain esxB is SAOUHSC_00265 and has amino acid sequence SEQ ID NO: 25 (GI:88194070).

Useful esxB antigens can elicit an antibody (e.g. when administered to a human) that recognises SEQ ID NO: 25 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100 or more). These esxB proteins include variants of SEQ ID NO: 25. Preferred fragments of (b) comprise an epitope from SEQ ID NO: 25. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 25 while retaining at least one epitope of SEQ ID NO: 25. Other fragments omit one or more protein domains.

sta006

The 'sta006' antigen is annotated as 'ferrichrome-binding protein', and has also been referred to as 'FhuD2' in the literature [158]. In the NCTC 8325 strain sta006 is SAOUHSC_02554 and has amino acid sequence SEQ ID NO: 26 (GI:88196199). In the Newman strain it is nwmn_2185 (GI:151222397).

Useful sta006 antigens can elicit an antibody (e.g. when administered to a human) that recognises SEQ ID NO: 26 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 26; and/or (b) comprising a fragment of at least 'n' consecutive amino acids of SEQ ID NO: 26, wherein 'n' is 7 or more (e.g. 8, 10, 12, 14, 16, 18, 20, 25, 30, 35, 40, 50, 60, 70, 80, 90, 100, 150, 200, 250 or more). These sta006 proteins include variants of SEQ ID NO: 26. Preferred fragments of (b) comprise an epitope from SEQ ID NO: 26. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 26 while retaining at least one epitope of SEQ ID NO: 26. The first 17 N-terminal amino acids of SEQ ID NO: 26 can usefully be omitted. Other fragments omit one or more protein domains. Mutant forms of sta006 are reported in reference 159. A sta006 antigen may be lipidated e.g. with an acylated N-terminus cysteine.

isdC

The 'isdC' antigen is annotated as 'protein'. In the NCTC 8325 strain isdC is SAOUHSC_01082 and has amino acid sequence SEQ ID NO: 27 (GI:88194830).

Useful isdC antigens can elicit an antibody (e.g. when administered to a human) that recognises SEQ ID NO: 27 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 27; and/or (b) comprising a fragment of at least 'n' consecutive amino acids of SEQ ID NO: 27, wherein 'n' is 7 or more (e.g. 8, 10, 12, 14, 16, 18, 20, 25, 30, 35, 40, 50, 60, 70, 80, 90, 100, 150, 200 or more). These isdC proteins include variants of SEQ ID NO: 27. Preferred fragments of (b) comprise an epitope from SEQ ID NO: 27. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 27 while retaining at least one epitope of SEQ ID NO: 27. The final 39 C-terminal amino acids of SEQ ID NO: 27 can usefully be omitted. The first 28 N-terminal amino acids of SEQ ID NO: 27 can usefully be omitted. Other fragments omit one or more protein domains. Useful fragments of IsdB are disclosed in reference 165.

Reference 160 discloses antigens which usefully include epitopes from both IsdB and IsdH.

Hla

The 'Hla' antigen is the 'alpha-hemolysin precursor' also known as 'alpha toxin' or simply 'hemolysin'. In the NCTC 8325 strain Hla is SAOUHSC_01121 and has amino acid sequence SEQ ID NO: 28 (GI:88194865). In the Newman strain it is nwmn_1073 (GI:151221285). Hla is an important virulence determinant produced by most strains of S. aureus, having pore-forming and haemolytic activity. Anti-Hla antibodies can neutralise the detrimental effects of the toxin in animal models, and Hla is particularly useful for protecting against pneumonia.

Useful Hla antigens can elicit an antibody (e.g. when administered to a human) that recognises SEQ ID NO: 28 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 28; and/or (b) comprising a fragment of at least 'n' consecutive amino acids of SEQ ID NO: 28, wherein 'n' is 7 or more (e.g. 8, 10, 12, 14, 16, 18, 20, 25, 30, 35, 40, 50, 60, 70, 80, 90, 100, 150, 200, 250 or more). These Hla proteins include variants of SEQ ID NO: 28. Preferred fragments of (b) comprise an epitope from SEQ ID NO: 28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 28 while retaining at least one epitope of SEQ ID NO: 28. The first 26 N-terminal amino acids of SEQ ID NO: 28 can usefully be omitted. Truncation at the C-terminus can also be used e.g. leaving only 50 amino acids (residues 27-76 of SEQ ID NO: 28) [161]. Other fragments omit one or more protein domains.

Hla's toxicity can be avoided in compositions of the invention by chemical inactivation (e.g. using formaldehyde, glutaraldehyde or other cross-linking reagents). Instead, however, it is preferred to use mutant forms of Hla which remove its toxic activity while retaining its immunogenicity. Such detoxified mutants are already known in the art. One useful Hla antigen has a mutation at residue 61 of SEQ ID NO: 28, which is residue 35 of the mature antigen (i.e. after omitting the first 26 N-terminal amino acids). Thus residue 61 may not be histidine, and may instead be e.g. Ile, Val or preferably Leu, A His-Arg mutation at this position can also be used. For example, SEQ ID NO: 29 is the mature mutant Hla-H35L sequence and a useful Hla antigen comprises SEQ ID NO: 29. Another useful mutation replaces a long loop with a short sequence e.g. to replace the 39mer at residues 136-174 of SEQ ID NO: 28 with a tetramer such as PSGS (SEQ ID NO: 30), as in SEQ ID NO: 31 (which also includes the H35L mutation) and SEQ ID NO: 32 (which does not include the H35L mutation).

Further useful Hla antigens are disclosed in references 162 and 163.

SEQ ID NOs: 33, 34 & 35 are three useful fragments of SEQ ID NO: 28 ('Hla$_{27-76}$', 'Hla$_{27-89}$' and 'Hla$_{27-79}$', respectively). SEQ ID NOs: 36, 37 and 38 are the corresponding fragments from SEQ ID NO: 29.

sta011

The 'sta011' antigen is annotated as 'lipoprotein'. In the NCTC 8325 strain sta011 is SAOUHSC_0.00052 and has amino acid sequence SEQ ID NO: 39 (GI:88193872).

Useful sta011 antigens can elicit an antibody (e.g. when administered to a human) that recognises SEQ ID NO: 39 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 39; and/or (b) comprising a fragment of at least 'n' consecutive amino acids of SEQ ID NO: 39, wherein 'n' is 7 or more (e.g. 8, 10, 12, 14, 16, 18, 20, 25, 30, 35, 40, 50, 60, 70, 80, 90, 100, 150, 200, 250 or more). These sta011 proteins include variants of SEQ ID NO: 39. Preferred fragments of (b) comprise an epitope from SEQ ID NO: 39. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 39 while retaining at least one epitope of SEQ ID NO: 39. The first 23 N-terminal amino acids of SEQ ID NO: 39 can usefully be omitted. Other fragments omit one or more protein domains. A sta006 antigen may be lipidated e.g. with an acylated N-terminus cysteine.

Variant forms of SEQ ID NO: 39 which may be used for preparing sta011 antigens include, but are not limited to, SEQ ID NOs: 40, 41 and 42 with various Ile/Val/Leu substitutions.

isdA

The 'isdA' antigen is annotated as 'IsdA protein'. In the NCTC 8325 strain isdA is SAOUHSC_01081 and has amino acid sequence SEQ ID NO: 43 (GI:88194829). In the Newman strain it is nwmn_1041 (GI:151221253).

Useful isdA antigens can elicit an antibody (e.g. when administered to a human) that recognises SEQ ID NO: 43 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 43; and/or (b) comprising a fragment of at least 'n' consecutive amino acids of SEQ ID NO: 43, wherein 'n' is 7 or more (e.g. 8, 10, 12, 14, 16, 18, 20, 25, 30, 35, 40, 50, 60, 70, 80, 90, 100, 150, 200, 250 or more). These isdA proteins include variants of SEQ ID NO: 43. Preferred fragments of (b) comprise an epitope from SEQ ID NO: 43. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 43 while retaining at least one epitope of SEQ ID NO: 43. The final 38 C-terminal amino acids of SEQ ID NO: 43 can usefully be omitted. The first 46 N-terminal amino acids of SEQ ID NO: 43 can usefully be omitted. Truncation to exclude the C-terminal 38mer of SEQ ID NO: 43 (beginning with the LPKTG motif) is also useful. Other fragments omit one or more protein domains.

SEQ ID NO: 44 is a useful fragment of SEQ ID NO: 43 (amino acids 40-184 of SEQ ID NO: 43; '$IsdA_{40-184}$') which includes the natural protein's heme binding site and includes the antigen's most exposed domain. It also reduces the antigen's similarity with human proteins. Other useful fragments are disclosed in references 164 and 165.

IsdA does not adsorb well to aluminium hydroxide adjuvants, so IsdA present in a composition may me unadsorbed or may be adsorbed to an alternative adjuvant e.g. to an aluminium phosphate.

isdB

The 'isdB' antigen is annotated as 'neurofilament protein isdB'. In the NCTC 8325 strain isdB is SAOUHSC_01079 and has amino acid sequence SEQ ID NO: 45 (GI: 88194828). IsdB has been proposed for use as a vaccine antigen on its own [166], but this may not prevent pneumonia.

Useful isdB antigens can elicit an antibody (e.g. when administered to a human) that recognises SEQ ID NO: 45 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 45; and/or (b) comprising a fragment of at least 'n' consecutive amino acids of SEQ ID NO: 45, wherein 'n' is 7 or more (e.g. 8, 10, 12, 14, 16, 18, 20, 25, 30, 35, 40, 50, 60, 70, 80, 90, 100, 150, 200, 250 or more). These isdB proteins include variants of SEQ ID NO: 45. Preferred fragments of (b) comprise an epitope from SEQ ID NO: 45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 45 while retaining at least one epitope of SEQ ID NO: 45. The final 36 C-terminal amino acids of SEQ ID NO: 45 can usefully be omitted. The first 40 N-terminal amino acids of SEQ ID NO: 45 can usefully be omitted. Other fragments omit one or more protein domains. Useful fragments of IsdB are disclosed in references 165 and 167 e.g. lacking 37 internal amino acids of SEQ ID NO: 45.

In some embodiments, compositions of the invention do not include an isdB antigen.

sta073

The 'sta073' antigen is annotated as 'bifunctional autolysin precursor'. In the NCTC 8325 strain sta073 is SAOUHSC_00994 and has amino acid sequence SEQ ID NO: 46 (GI:88194750). In the Newman strain it is nwmn_0922 (GI:151221134). Proteomic analysis has revealed that this protein is secreted or surface-exposed.

Useful sta073 antigens can elicit an antibody (e.g. when administered to a human) that recognises SEQ ID NO: 46 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 46; and/or (b) comprising a fragment of at least 'n' consecutive amino acids of SEQ ID NO: 46, wherein 'n' is 7 or more (e.g. 8, 10, 12, 14, 16, 18, 20, 25, 30, 35, 40, 50, 60, 70, 80, 90, 100, 150, 200, 250 or more). These sta073 proteins include variants of SEQ ID NO: 46. Preferred fragments of (b) comprise an epitope from SEQ ID NO: 46. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 46 while retaining at least one epitope of SEQ ID NO: 46. The first 24 N-terminal amino acids of SEQ ID NO: 46 can usefully be omitted. Other fragments omit one or more protein domains.

Sta073 does not adsorb well to aluminium hydroxide adjuvants, so Sta073 present in a composition may me unadsorbed or may be adsorbed to an alternative adjuvant e.g. to an aluminium phosphate.

Hybrid Polypeptides

*S. aureus* protein antigens used in the invention may be present in the composition as individual separate polypeptides. Where more than one antigen is used, however, they do not have to be present as separate polypeptides. Instead, at least two (e.g. 2, 3, 4, 5, or more) antigens can be expressed as a single polypeptide chain (a 'hybrid' polypeptide). Hybrid polypeptides offer two main advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

The hybrid polypeptide may comprise two or more polypeptide sequences from each of the antigens listed above, or two or more variants of the same antigen in the cases in which the sequence has partial variability across strains.

Hybrids consisting of amino acid sequences from two, three, four, five, six, seven, eight, nine, or ten antigens are useful. In particular, hybrids consisting of amino acid sequences from two, three, four, or five antigens are preferred, such as two or three antigens.

Different hybrid polypeptides may be mixed together in a single formulation. Hybrids may be combined with non-hybrid antigens selected from the first, second or third antigen groups. Within such combinations, an antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-$\{$-X-L-$\}_n$-B—COOH, wherein: X is an amino acid sequence of a *S. aureus* antigen, as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a -X- moiety has a leader peptide sequence in its wild-type form, this may be included or omitted in the hybrid protein. In some embodiments, the leader peptides will be deleted except for that of the -X- moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of $\{$-X-L-$\}$, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO: 47) or GSGSGGGG (SEQ ID NO: 48), with the Gly-Ser dipeptide being formed from a BamHI restriction site, thus aiding cloning and manipulation, and the $(Gly)_4$ tetrapeptide being a typical poly-glycine linker. Other suitable linkers, particularly for use as the final $L_n$ are ASGGGS (SEQ ID NO: 49) e.g. encoded by SEQ ID NO: 50) or a Leu-Glu dipeptide.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more, such as SEQ ID NO: 51), or sequences which enhance protein stability. Other suitable C-terminal amino acid sequences will be apparent to those skilled in the art.

One hybrid polypeptide of the invention may include both EsxA and EsxB antigens. These may be in either order, N- to C-terminus. SEQ ID NOs: 52 ('EsxAB'; encoded by SEQ ID NO: 53) and 54 ('EsxBA') are examples of such hybrids, both having hexapeptide linkers ASGGGS (SEQ ID NO: 49).

General

The practice of the present invention will employ, unless otherwise indicated, conventional methods of chemistry, biochemistry, molecular biology, immunology and pharmacology, within the skill of the art. Such techniques are explained fully in the literature. See, e.g., references 168-175, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 176. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 177.

Where the invention concerns an "epitope", this epitope may be a B-cell epitope and/or a T-cell epitope. Such epitopes can be identified empirically (e.g. using PEPSCAN [178,179] or similar methods), or they can be predicted (e.g. using the Jameson-Wolf antigenic index [180], matrix-based approaches [181], MAPITOPE [182], TEPITOPE [183, 184], neural networks [185], OptiMer & EpiMer [186, 187], ADEPT [188], Tsites [189], hydrophilicity [190], antigenic index [191] or the methods disclosed in references 192-196, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. The different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

MODES FOR CARRYING OUT THE INVENTION

A. Purification of S. aureus Type 5 Capsular Polysaccharide

Comparative Example

Figure 1:
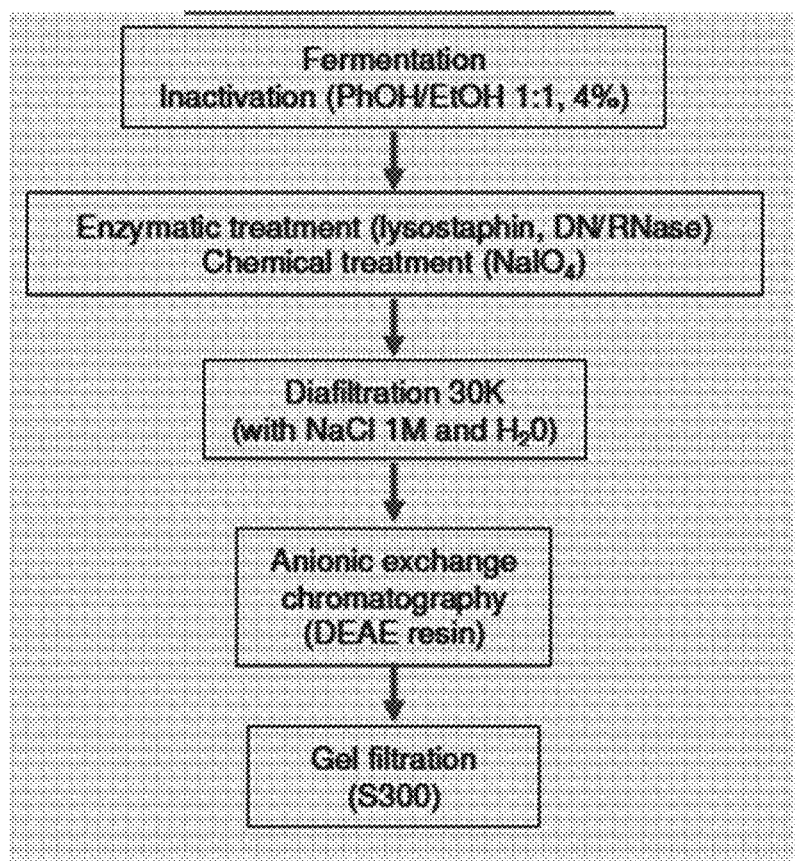
FIG. 1 illustrates a process for purifying S. aureus type 5 and type 8 capsular polysaccharides based on the method of reference 13.

S. aureus type 5 capsular polysaccharide was purified according to the scheme illustrated in FIG. 1, based on the method of reference 13. The conditions and rationale for the various steps of this method are described in Table 1:

TABLE 1

| Step | Conditions | Rationale |
| --- | --- | --- |
| Bacterial growth on plates | | |
| Bacterial pellet centrifugation | | Harvest of cells |
| Reaction with Lysostaphin | 100 µg/ml of Lysostaphin overnight at 37° C. | Cell wall lysis and release of capsular polysaccharide |
| Reaction with DNse/RNase | 50 µg/ml of DNase and RNase at 37° C. for 6-8 hrs | Nucleic acid hydrolysis |
| Reaction with NaIO$_4$ | 0.05M NaIO$_4$ for 5 hrs a RT in the dark | Teichoic acid hydrolisis |
| Diafiltration 30 kDa | Washing with NaCl 1M and H$_2$O | Low molecular weight species removal |
| Anion exchange chromatography (DEAE SepharoseFF resin) | NaCl 1M gradient | Separation according to charge (protein removal) |
| Gel filtration (Sephacryl S300) | NaPi 10 mM pH 7.2 and NaCl 10 mM | Separation according to molecular weight |

Bacterial Pellet Centrifugation and Enzymatic Reactions (Lysostaphin and RNase/DNase)

S. aureus was grown in solid medium to provide a bacterial suspension of 600-800 ml. The wet cell pellet, harvested by centrifugation at 8000 rpm, had a mass of around 30-50 g. The harvested pellet was washed three times with 50 mM Tris-2 mM MgSO$_4$ pH7.5 and then suspended at 0.25-0.58 g per ml in 50 mM Tris-2 mM MgSO$_4$ pH7.5 and treated with 0.1-0.13 mg/ml of lysostaphin (Sigma-Aldrich). The reaction mixture was incubated at 37° C. for 16 hrs (ON) with mild stirring. 0.05 mg/ml of DNase/RNase (Sigma-Aldrich) was added to the suspension and incubated for 5-7 hrs at 37° C. The suspension was then clarified by centrifugation.

Reaction with NaIO$_4$

The material was incubated with 50 mM NaIO$_4$ (Sigma-Aldrich) in the dark for 5-7 hrs. NaIO$_4$ was then removed by the addition of excess glycerol for 30 minutes with stirring in the light.

30 kDa Tangential Flow Filtration

Tangential flow filtration was carried out as indicated in Table 2:

TABLE 2

| | |
|---|---|
| Membrane type | Sartorius Hydrosart ™ 30 kDa |
| Surface area | 0.1 m² |
| $P_{in}/P_{out}$ | 0.4/0.0 bar |
| Permeate flow rate | 80 ml/min |
| Diafiltration volumes | 10 volumes of NaCl 1M followed by 10 volumes of distilled water |
| Product recovery | Retentate volume + two washings with distilled water equal to the dead volume of the system (with completely open retentate and closed permeate) |

The tangential flow filtration was performed in a Sartorius™ holder for 0.1 m² cassettes using a WatsonMarlon™ peristaltic pump. Afterwards, the membrane was washed with NaOH 1M and stored in NaOH 0.1M at +2-8° C.

DEAE Sepharose Fast Flow Chromatography

Residual protein, nucleic acid and other impurities were removed by anion exchange chromatography carried out in accordance with Table 3:

TABLE 3

| | |
|---|---|
| Resin | DEAE Sepharose ™ Fast Flow resin (G&E Healthcare) |
| Column dimension | Ø = 5 cm; h = 7.5 cm; V = 150 ml |
| Equilibration | 10 mM NaPi buffer pH7.2 q.b. to reach 1.8-2.0 mS/cm eluate conductivity |
| Load | Retentate from 30K UF buffered to 10 mM NaPi buffer pH7.2 |
| Elution | 20 column volumes of 10 mM NaPi buffer pH7.2 |
| Stripping | 20 column volumes of NaCl 1M |

Figure 2A:
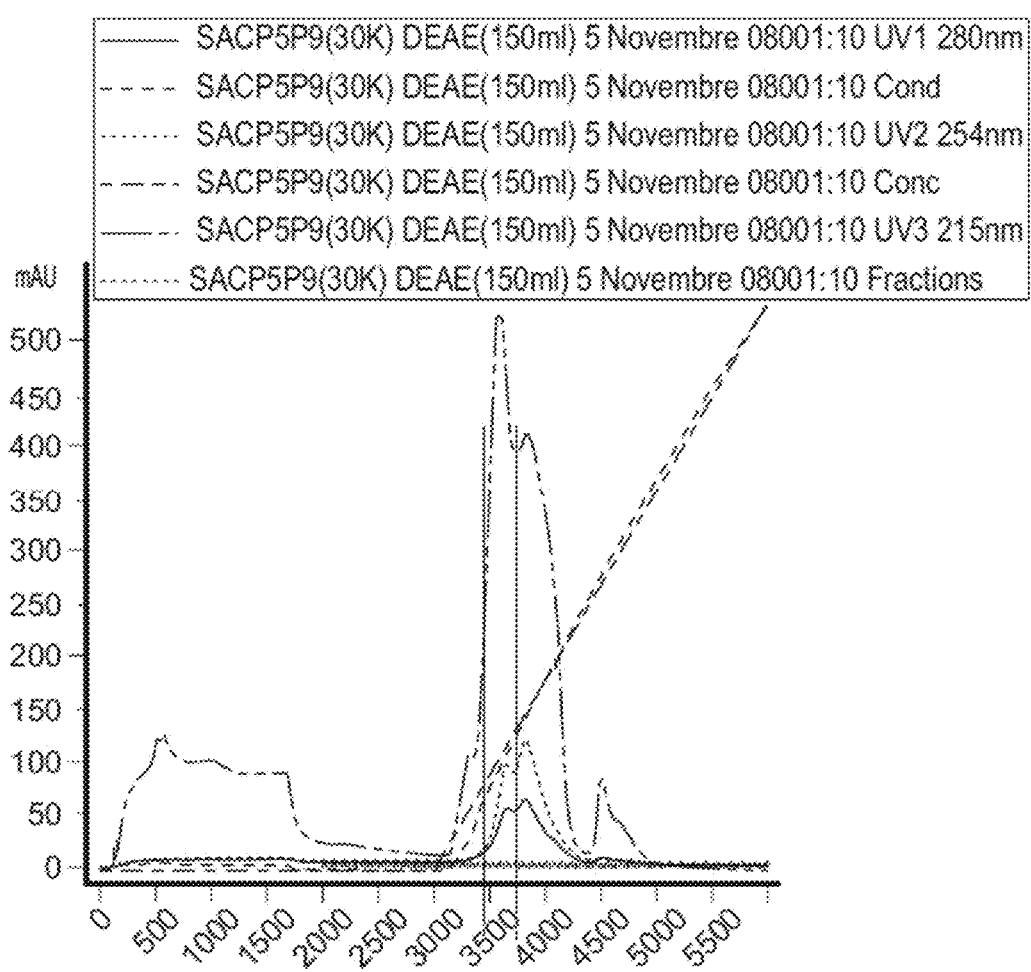
FIG. 2A-FIG. 2B shows a DEAE Sepharose chromatogram of capsular polysaccharide (FIG. 2A) and a $^1$H NMR spectrum of capsular polysaccharide-containing fractions (fractions 68-80) (FIG. 2B) prepared according to the method of FIG. 1.
Figure 2B:
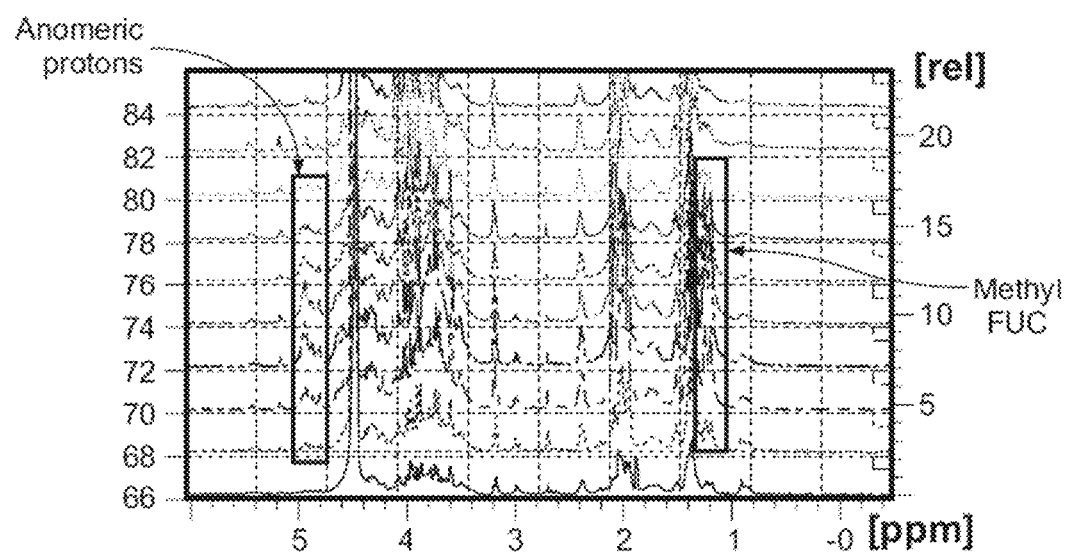

The chromatography was performed using an Akta™ system (G&E Healthcare) and the capsular polysaccharide was detected by measuring UV absorption at 215 nm. The capsular polysaccharide solution was first added to 100 mM NaPi buffer pH7.2 to obtain a final buffer concentration of 10 mM NaPi pH7.2. The DEAE resin was pre-equilibrated with 100 mM NaPi buffer pH7.2 to pH7.2 and then equilibrated with 10 mM NaPi buffer pH7.2 to achieve the indicated conductivity (10 mM NaPi buffer pH7.2 conductivity). The resultant fractions were analyzed by NMR and those containing capsular polysaccharide pooled together (FIG. 2).

S300 Sephacryl Chromatography

The polysaccharide was further purified by gel-filtration chromatography carried out in accordance with Table 4:

TABLE 4

| | |
|---|---|
| Resin | S300 Sephacryl ™ resin (G&E Healthcare) |
| Column dimension | Ø = 2.6 cm; h = 95 cm; V = 500 ml |
| Equilibration | 50 mMNaCl buffer q.b. to reach 6.3-6.5 mS/cm eluate conductivity |
| Load | 12-14 ml |
| Elution | 50 mMNaCl buffer |

Figure 3A:
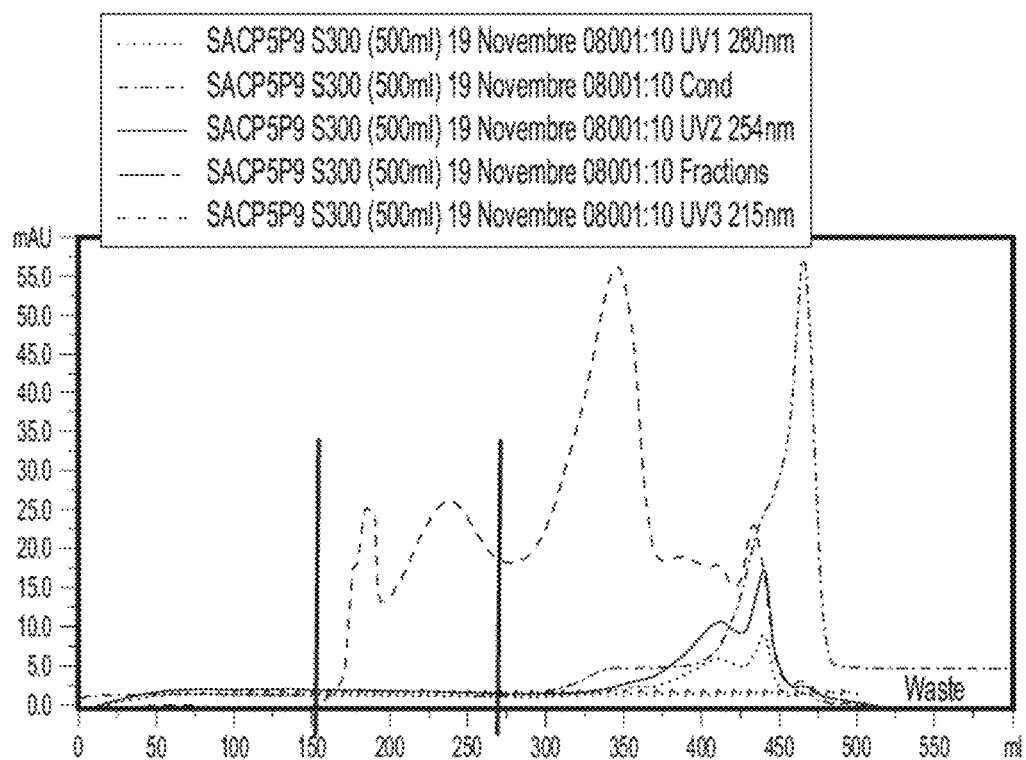
FIG. 3A-FIG. 3B shows a S300 Sephacryl chromatogram of capsular polysaccharide (FIG. 3A) and a $^1$H NMR spectrum of capsular polysaccharide-containing fractions (fractions 22-44) (FIG. 3B) prepared according to the method of FIG. 1.
Figure 3B:
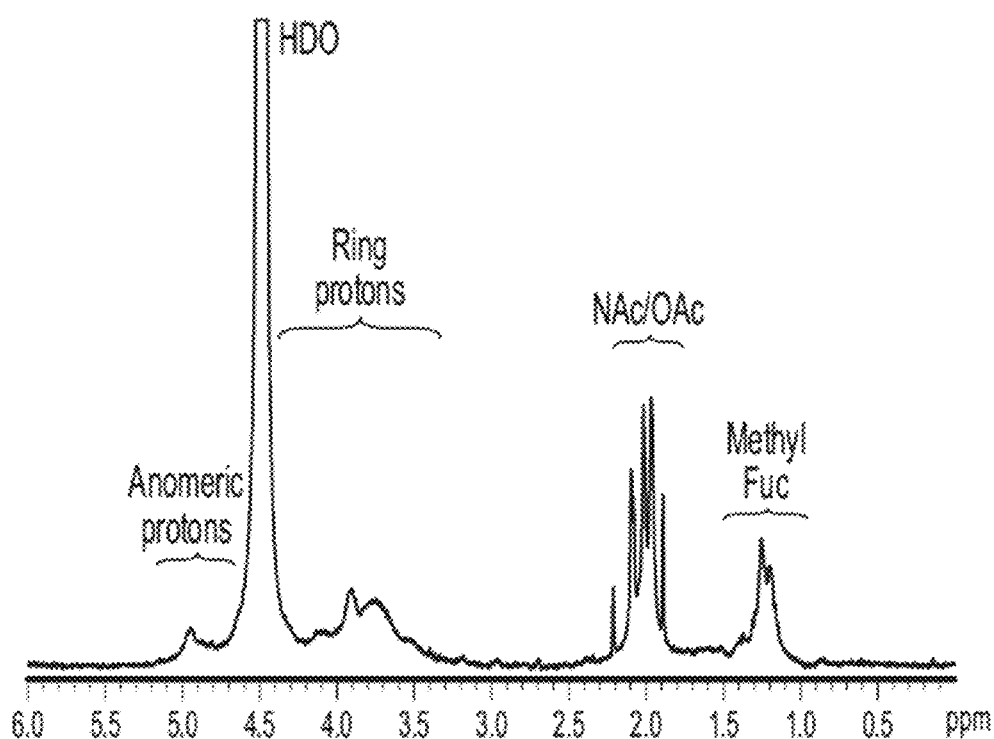

The chromatography was performed on an Akta™ system (G&E Healthcare) and the capsular polysaccharide was detected by measuring UV absorption at 215 nm. The resultant fractions were analyzed by NMR and those containing capsular polysaccharide pooled together (FIG. 3).

B. Purification of *S. aureus* Type 5 and Type 8 Capsular Polysaccharides

Example

Figure 4:
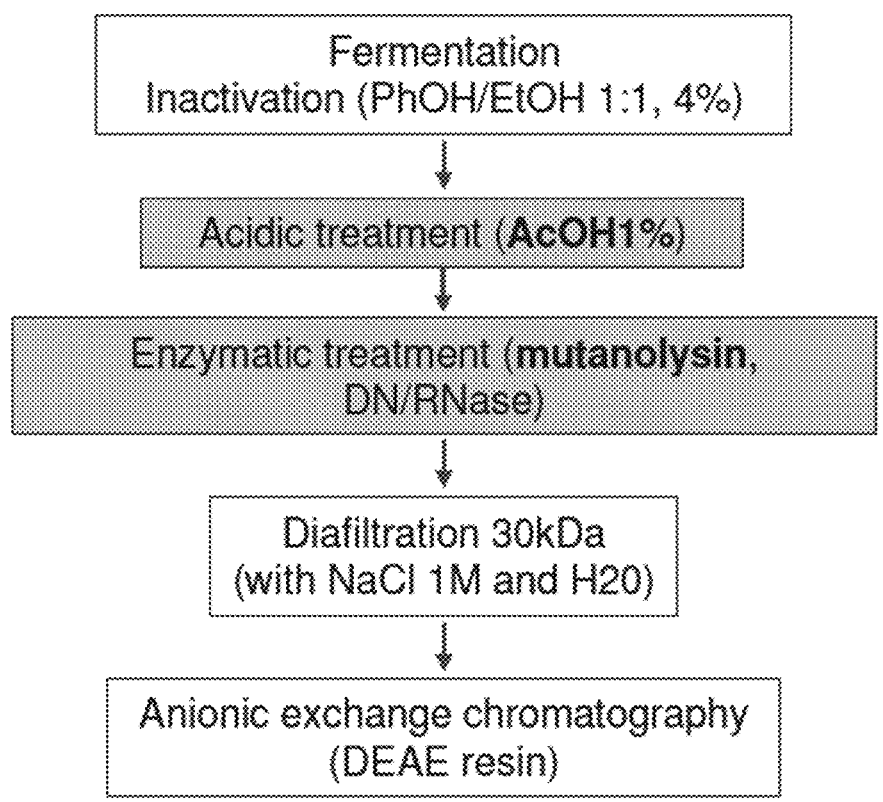
FIG. 4 illustrates an exemplary process of the invention for purifying S. aureus type 5 and type 8 capsular polysaccharides.

*S. aureus* type 5 and type 8 capsular polysaccharides were purified according to the scheme illustrated in FIG. 4. The conditions and rationale for the various steps of this method are described in Table 5:

TABLE 5

| Step | Conditions | Rationale |
|---|---|---|
| Bacterial growth on plates | | |
| Bacterial pellet centrifugation | | Harvest of cells |
| Reaction with AcOH1% | 2 hrs at 100° C. | Cell wall lysis and release of capsular polysaccharide |
| Reaction with mutanolysin | 180 U/ml of mutalysin at 37° C. over-night | Further removal of peptidoglycan |
| Reaction with DNse/RNase | 50 μg/ml of DNase and RNase at 37° C. for 6-8 hrs | Nucleic acid hydrolysis |
| Diafiltration 30 kDa | Washing with NaCl 1M and H₂O | Low molecular weight species removal |
| Anion exchange chromatography (DEAE SepharoseFF resin) | NaCl 1M gradient | Separation according to charge (protein removal) |

Bacterial Pellet Centrifugation and Acid and Enzymatic Reactions (Acetic Acid, RNase/DNase and Mutanolysin)

*S. aureus* was grown in solid medium to provide a bacterial suspension of 600-800 ml. The wet cell pellet, harvested by centrifugation at 8000 rpm, had a mass of around 30-50 g. The harvested pellet was washed three times with 50 mM Tris-2 mM MgSO₄ pH7.5 and then suspended at 0.5-0.6 g per ml in distilled water and stirred vigorously while the temperature was raised to 100° C. Acetic acid was then added to a final concentration of 1% and the mixture kept at 100° C. for 2 hrs. The mixture was neutralised with NaOH 1M and centrifuged at 8000 rpm.

The supernatant was decanted from the pellet and combined with 0.05 mg/ml of DNase/RNase (Sigma-Aldrich). The mixture was then incubated for 5-7 hrs at 37° C. and afterwards clarified by centrifugation. 180 U/ml of mutanolysin (Sigma-Aldrich) was then added to the suspension and the mixture incubated over-night (for 16 hrs) at 37° C. with mild stirring. The suspension was then clarified again by centrifugation.

30 kDa Tangential Flow Filtration

Tangential flow filtration was carried out as indicated in Table 6:

TABLE 6

| | |
|---|---|
| Membrane type | Sartorius Hydrosart ™ 30 kDa |
| Surface area | 0.2 m² |
| $P_{in}/P_{out}$ | 0.7/0.0 bar |
| Permeate flow rate | 11 ml/min |
| Diafiltration volumes | 10 volumes of NaCl 1M followed by 10 volumes of NaPi 10 mM pH 7.2 buffer |
| Product recovery | Retentate volume + two washings with distilled water equal to the dead volume of the system (with completely open retentate and closed permeate) |

The tangential flow filtration was performed in a Sartorius™ holder for 0.2 m² cassettes using a WatsonMarlon™ peristaltic pump. Afterwards, the membrane was washed with NaOH 1M and stored in NaOH 0.1M at +2-8° C.

DEAE Sepharose Fast Flow Chromatography

Residual protein, nucleic acid and other impurities were removed by anion exchange chromatography carried out in accordance with Table 7:

TABLE 7

| | |
|---|---|
| Resin | DEAE Sepharose ™ Fast Flow resin (G&E Healthcare) |
| Column dimension | Ø = 5 cm; h = 7.5 cm; V = 150 ml |
| Equilibration | 10 mM NaPi buffer pH7.2 q.b. to reach 1.8-2.0 mS/cm eluate conductivity |
| Load | Retentate from 30K UF |
| Elution | 20 column volumes of 10 mM NaPi buffer pH7.2 |
| Stripping | 20 column volumes of NaCl 1M |

Figure 5:
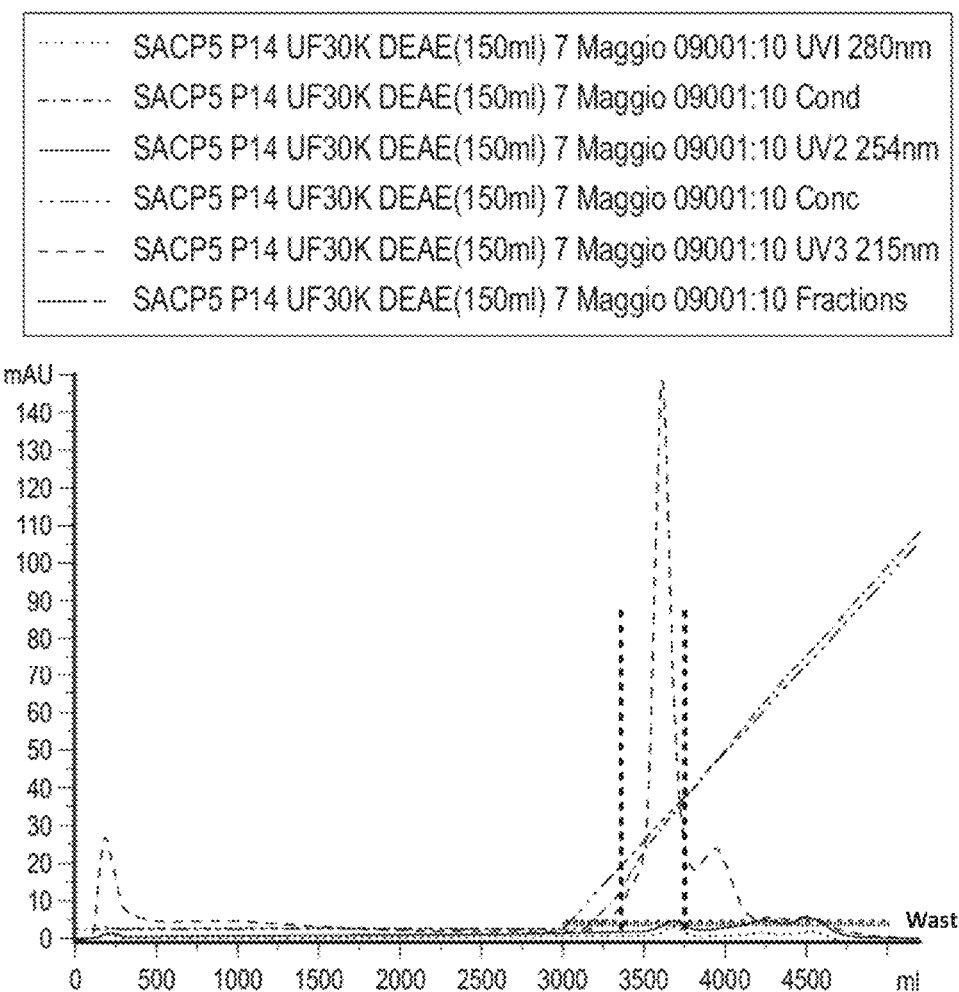
FIG. 5 shows a DEAE Sepharose chromatogram of capsular polysaccharide prepared according to a method of the invention.

The chromatography was performed using an Akta™ system (G&E Healthcare) and the capsular polysaccharide was detected by measuring UV absorption at 215 nm. The capsular polysaccharide solution was first added to 100 mM NaPi buffer pH7.2 to obtain a final buffer concentration of 10 mM NaPi pH7.2. The DEAE resin was pre-equilibrated with 100 mM NaPi buffer pH7.2 to pH7.2 and then equilibrated with 10 mM NaPi buffer pH7.2 to achieve the indicated conductivity (10 mM NaPi buffer pH7.2 conductivity). The resultant fractions were analyzed by NMR and those containing capsular polysaccharide pooled together (FIG. 5).

30 kDa Tangential Flow Filtration

Tangential flow filtration was carried out to remove NaCl left over from the anion exchange chromatography and to concentrate the purified polysaccharides. The filtration was carried out as indicated in Table 8:

TABLE 8

| | |
|---|---|
| Membrane type | Sartorius Hydrosart ™ 30 kDa |
| Surface area | 0.2 m² |
| $P_{in}/P_{out}$ | 0.7/0.0 bar |
| Permeate flow rate | 11 ml/min |
| Diafiltration volumes | 10 volumes of distilled water |
| Product recovery | Retentate volume + two washings with distilled water equal to the dead volume of the system (with completely open retentate and closed permeate) |

Figure 6:
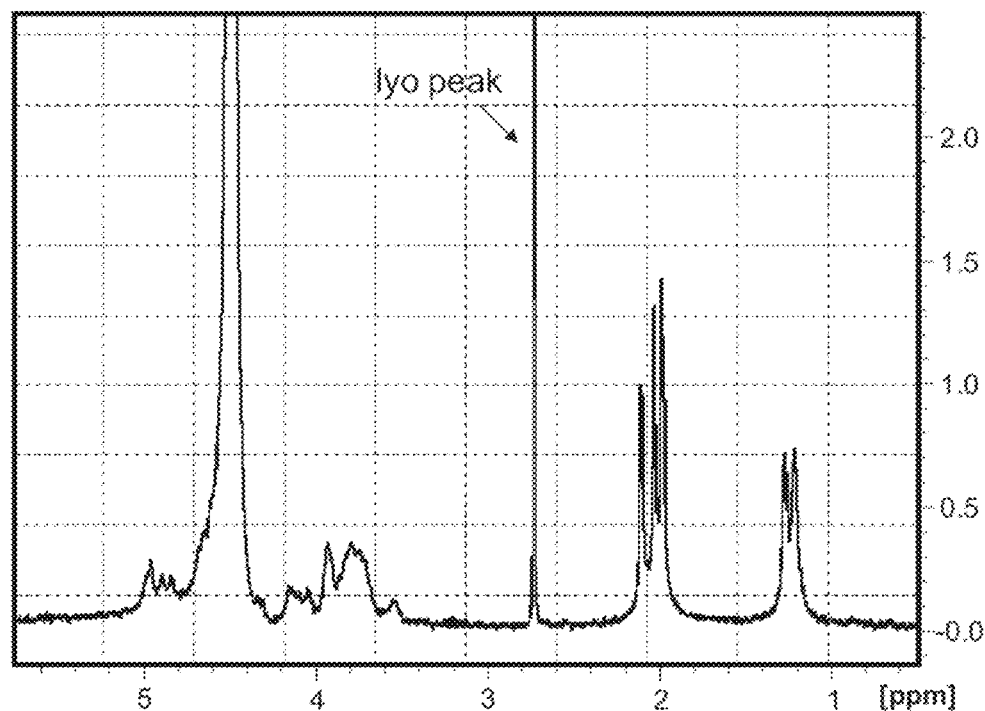
FIG. 6 shows a $^1$H NMR spectrum for purified S. aureus type 5 capsular polysaccharide.

The tangential flow filtration was performed in a Sartorius™ holder for 0.2 m² cassettes using a WatsonMarlon™ peristaltic pump. Afterwards, the membrane was washed with NaOH 1M and stored in NaOH 0.1M at +2-8° C. The purified polysaccharide was analysed by NMR (e.g. FIG. 6 for the type 5 capsular polysaccharide).

C. Determination of Peptidoglycan Contamination in Purified Polysaccharide

The peptidoglycan (FIG. 7) content of purified type 5 polysaccharide obtained according to the methods in sections A and B above was determined by amino acid analysis using HPAEC-PAD according to the Dionex AAA-Direct™ system (AminoPac™ PA10 AAA-Direct™, Dionex) in accordance with the manufacturer's instructions. Briefly, 20 μL of 100 μM norleucine was added to 200 μL of polysaccharide at 250 μg/mL in water in a 400° C. treated glass tube and dried using a Speedvac system. The norleucine serves as an internal standard. Samples were hydrolyzed in vacuo using the vapor of boiling hydrochloric acid/phenol in order to yield free amino acids from residual protein and peptidoglycan contamination. Separation of free amino acids was performed on an AminoPac™ PA10 column (2×250 mm) equipped with an AminoPac™ PA10 guard column (2×50 mm) using a gradient condition for amino acids and carbohydrates according to the manufacturer's recommendations. These gradient conditions are summarized in Table 9:

TABLE 9

| Time (min) | % E1 | % E2 | % E3 | Curve | Comments |
|---|---|---|---|---|---|
| Initiation | 84 | 16 | 0 | | Autosampler fills the sample loop |
| 0.0 | 84 | 16 | 0 | | Valve from Load to Inject |
| 2.0 | 84 | 16 | 0 | | Begin hydroxide gradient |
| 12.1 | 68 | 32 | 0 | 8 | |
| 16.0 | 68 | 32 | 0 | | Begin acetate gradient |
| 24.0 | 36 | 24 | 40 | 8 | |
| 40.0 | 36 | 24 | 40 | | |
| 40.1 | 20 | 80 | 0 | 5 | Column wash with hydroxide |
| 42.1 | 20 | 80 | 0 | | |
| 42.2 | 84 | 16 | 0 | 5 | Equilibrate to starting conditions |
| 65.0 | 84 | 16 | 0 | | |

Eluent E1: Deionized Water;
Eluent E2: 0.250M Sodium Hydroxide;
Eluent E3: 1.0M Sodium Actote and Flow = 0.25 mL/min.

Detection was performed using a AAA-Direct waveform potential (Table 10).

TABLE 10

| Time (sec) | Potential (V) vs. Ag/AgCl | Potential (V) vs. pH | Integration |
|---|---|---|---|
| 0.000 | −0.20 | +0.13 | |
| 0.040 | −0.20 | +0.13 | |
| 0.050 | 0.00 | +0.33 | |
| 0.210 | 0.00 | +0.33 | Begin |
| 0.220 | +0.22 | +0.55 | |
| 0.460 | +0.22 | +0.55 | |
| 0.470 | 0.00 | +0.33 | |
| 0.560 | 0.00 | +0.33 | End |
| 0.570 | −0.20 | −1.67 | |
| 0.580 | −0.20 | −1.67 | |
| 0.590 | −0.60 | −0.93 | |
| 0.600 | −0.20 | +0.13 | |

The quantification was performed using a non-hydrolyzed 17 amino acid standard solution (Fluka P/N 09428) in the range 2.5-50 μM. Standard samples were analyzed with and without norleucine, at the same sample concentration. The ratio of the norleucine peak area in the sample divided by the average norleucine peak area in the standards was used as a correction factor for possible amino acid loss in the hydrolysis step. A BSA sample was used as control sample.

Peptidoglycan Content Estimation

Peptidoglycan content was estimated using two different methods. The first method (method 1) was based on the method used in reference 17, which involves a summation of the lysine, alanine, glycine and glutamate content. In the second method (method 2), a conversion factor is calculated for each amino acid according to the following formula:

(molecular mass of amino acid)×(number of residues in the peptidoglycan structure)/(molecular mass of the repeating unit of peptidoglycan).

Figure 7:
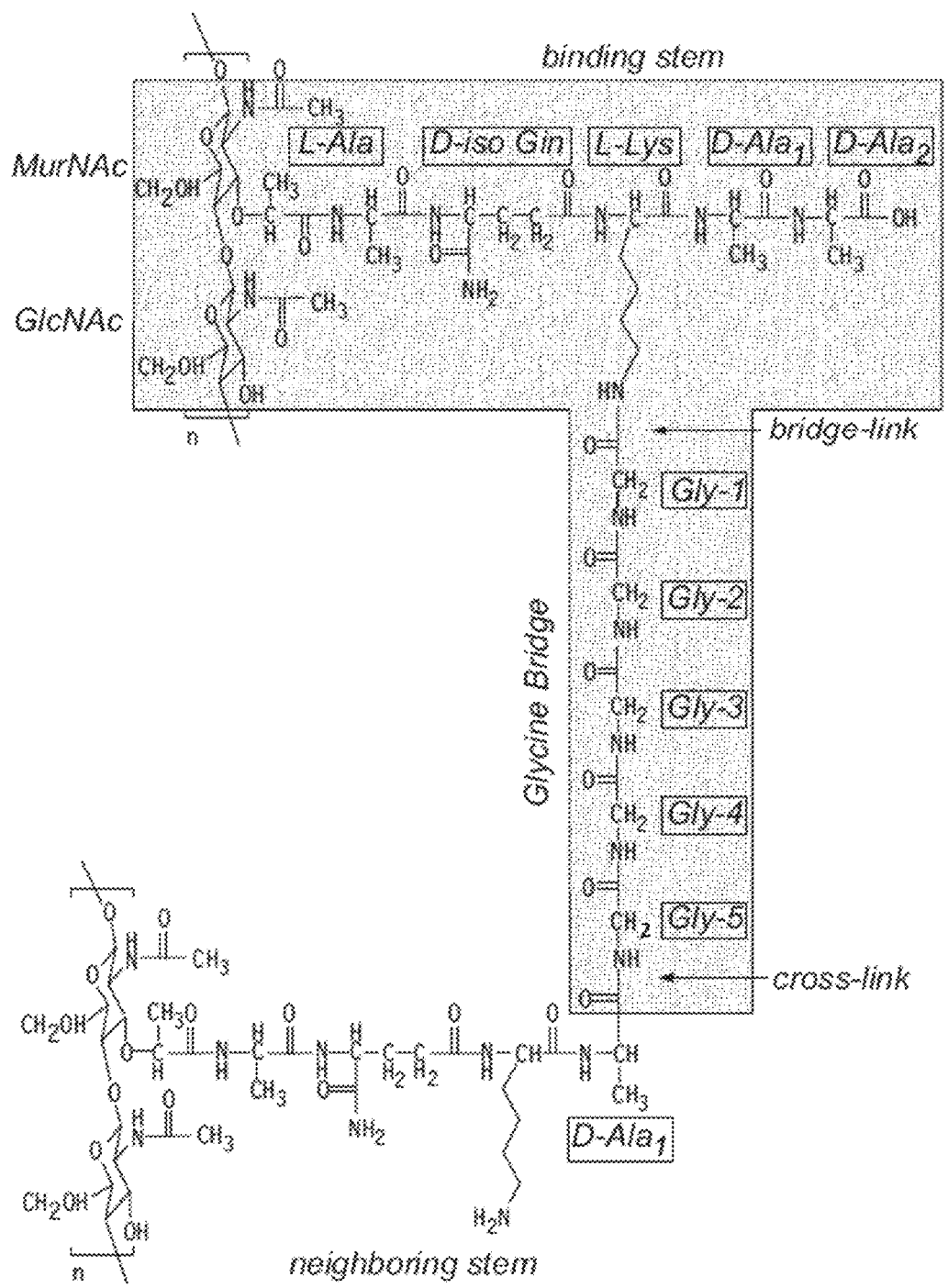
FIG. 7 shows the chemical structure of the peptidoglycan of S. aureus based on references 197, 198, 199 and 200. The repeat unit is highlighted.

The molecular mass of the repeating unit of peptidoglycan is 1233.27 Da (FIG. 7). The peptidoglycan content was then calculated as the average peptidoglycan concentration obtained by calculating the ratio of the amino acid concentration and the conversion factor.

The peptidoglycan content of the purified type 5 capsular polysaccharide after anionic exchange chromatography is given in Table 11:

TABLE 11

| Measurement method | Details of calculation | % Peptidoglycan | |
|---|---|---|---|
| | | Measurement 1 | Measurement 2 |
| 1 | Calculated according to reference 17 as sum of Lys-Ala-Gly-Glx concentration | 2.04 | 0.74 |
| 1 | Calculated according to reference 17 as sum of all amino acids detectable except for Lys-Ala-Gly-Glx | 0.48 | 0.85 |
| 2 | Calculated using Ala and Gly concentration divided by PG conversion factor (Ala = 0.2167, Gly = 0.3043) | 0.88 | 0.81 |

The method of the invention provides a very low content of peptidoglycan in the purified polysaccharide.

D. Conjugation and Immunogenicity of Purified Polysaccharides

Purified type 5 polysaccharides obtained from the methods in sections A and B above were conjugated to CRM197 according to the method of reference 29. Total saccharide in the conjugate was determined by HPAEC-PAD analysis and protein content by MicroBCA assay (Table 12).

TABLE 12

| Purification method | Lot | Protein (µg/ml) | Saccharide (µg/ml) | Saccharide/protein (w/w) |
|---|---|---|---|---|
| A | 1 | 51.52 | 1.72 | 0.03 |
| A | 2 | 161.80 | 17.10 | 0.11 |
| A | 3 | 34.42 | 4.22 | 0.12 |
| B | 4 | 444.0 | 139.0 | 0.31 |
| B | 5 | 40.56 | 12.70 | 0.31 |

The conjugates prepared using polysaccharides purified by the method of the invention (lots 4 and 5) had higher polysaccharide:protein ratios.

The immunogenicity of lot 5 was tested in a mouse lethal model of *S. aureus* infection. Briefly, CD1 mice were immunised by intraperitoneal injection with a 2 µg dose of antigen in an injection volume of 200 µl. Immunisations were carried out in groups of twelve mice according to the following scheme, prior to challenge by intraperitoneal injection of a bacterial suspension of $5\times10^8$ CFU type 5 *S. aureus*. Cultures of *S. aureus* were centrifuged, washed twice and diluted in PBS before challenge. Further dilutions were needed for the desired inoculum, which was experimentally verified by agar plating and colony formation. Animals were monitored for 14 days and lethal disease recorded.

Group 1—PBS plus alum

Group 2—Type 5 capsular polysaccharide-CRM conjugate (Lot 5) plus alum

Group 4—Type 5 capsular polysaccharide-CRM conjugate (Lot 5) plus EsxAB, Sta006 and Sta011 proteins and alum Group 5—Type 5 capsular polysaccharide-CRM conjugate (Lot 5) plus HlaH35L, Sta006 and Sta011 proteins and alum Survival data is presented in Table 13:

TABLE 13

| Group | Time (days) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 1 | 100 | 25 | 17 | 17 | 17 | 17 | 17 | 17 | 17 | 17 | 8 | 0 | 0 | 0 |
| 2 | 100 | 50 | 50 | 50 | 50 | 50 | 50 | 50 | 50 | 42 | 42 | 42 | 42 | 42 |
| 4 | 100 | 67 | 67 | 67 | 67 | 67 | 67 | 67 | 67 | 67 | 67 | 67 | 67 | 67 |
| 5 | 100 | 100 | 100 | 100 | 100 | 100 | 83 | 83 | 75 | 75 | 75 | 75 | 75 | 75 |

The conjugates prepared using polysaccharides purified by the method of the invention gave a high level of survival. Survival was enhanced by addition of *S. aureus* protein antigens.

It will be understood that the invention has been described by way of example only and modifications may be made whilst remaining within the scope and spirit of the invention.

REFERENCES

[1] Fattom et al. (1990) *Infect Immun.* 58(7):2367-74.
[2] Fattom et al. (1992) *Infect Immun.* 60(2):584-9.
[3] Fattom et al. (1993) *Infect Immun.* 61(3):1023-32.
[4] Fattom et al. (1996) *Infect Immun.* 64(5): 1659-65.
[5] Welch et al. (1996) *J Am Soc Nephrol.* 7(2):247-53.
[6] Fattom et al. (1998) *Infect Immun.* 66(10):4588-92.
[7] Fattom et al. (1993) *Vaccine* 17(2):126-33.
[8] Fattom et al. (2002) *N Engl J Med.* 346(7):491-6.
[9] Robbins et al. (2005) *Ann N Y Acad Sci.* 754:68-82.
[10] Gilbert et al. (1994) *J. Microb. Meth.* 20:39-46.
[11] Gilbert et at (1994) *Vaccine.* 12(4):369-74.
[12] Tollersrud et al. (2001) *Vaccine.* 19(28-29):3896-903.
[13] Lee et al. (1993) *Infect Immun* 61:1853-8.
[14] WO2004/080490.
[15] WO2006/032475.
[16] WO2006/032500.
[17] WO2006/065553.
[18] WO2006/114500.
[19] Moreau et al. (1990) *Carbohydrate Res.* 339(5):285-91
[20] Fournier et al. (1984) *Infect. Immun.* 45(1):87-93.
[21] Jones (2005) *Carbohydrate Res.* 340(6):1097-106.
[22] Lemercinier and Jones (1996) *Carbohydrate Res.* 296: 83-96.

[23] Jones and Lemercinier (2002) *J Pharm Biomed Anal.* 30(4): 1233-47.
[24] WO05/033148
[25] WO 00/56357
[26] Hestrin (1949) *J. Biol. Chem.* 180:249-261.
[27] Konadu et al. (1994) *Infect. Immun.* 62:5048-5054.
[28] www.polymer.de
[29] U.S. patent application 61/247,518, 'CONJUGATION OF *STAPHYLOCOCCUS AUREUS* TYPE 5 AND TYPE 8 CAPSULAR POLYSACCHARIDES' (NOVARTIS AG). Assignee reference no. 53594-US-PSP and PCT application no. PCT/IB2010/002565 (NOVARTIS AG).
[30] WO2007/113222
[31] U.S. Pat. No. 6,045,805
[32] U.S. Pat. Nos. 6,027,733 & 6,274,144.
[33] www.polymer.de
[34] Wessels et al. (1989) *Infect Immun* 57:1089-94.
[35] Ramsay et al. (2001) *Lancet* 357(9251):195-196.
[36] Lindberg (1999) *Vaccine* 17 Suppl 2:S28-36.
[37] Buttery & Moxon (2000) *J R Coll Physicians Lond* 34:163-68.
[38] Ahmad & Chapnick (1999) *Infect Dis Clin North Am* 13:113-33, vii.
[39] Goldblatt (1998) *J. Med. Microbiol.* 47:563-7.
[40] European patent 0477508.
[41] U.S. Pat. No. 5,306,492.
[42] WO98/42721.
[43] Dick et al. in *Conjugate Vaccines* (eds. Cruse et al.) Karger, Basel, 1989, 10:48-114.
[44] Hermanson *Bioconjugate Techniques*, Academic Press, San Diego (1996) ISBN: 0123423368.
[45] Reynaud-Rondier et al. (1991) *FEMS Microbiology Immunology* 76:193-200.
[46] WO03/061558.
[47] *Research Disclosure*, 453077 (January 2002)
[48] Herbelin et al. (1997) *J Dairy Sci.* 80(9):2025-34.
[49] EP-A-0372501.
[50] EP-A-0378881.
[51] EP-A-0427347.
[52] WO93/17712
[53] WO94/03208.
[54] WO98/58668.
[55] EP-A-0471177.
[56] WO91/01146
[57] Falugi et al. (2001) *Eur J Immunol* 31:3816-3824.
[58] Baraldo et al. (2004) *Infect Immun* 72(8):4884-7.
[59] EP-A-0594610.
[60] Ruan et al. (1990) *J Immunol* 145:3379-3384.
[61] WO00/56360.
[62] WO02/091998.
[63] Kuo et al. (1995) *Infect Immun* 63:2706-13.
[64] Michon et al. (1998) *Vaccine.* 16:1732-41.
[65] WO01/72337
[66] WO00/61761.
[67] WO2004/041157.
[68] WO02/34771.
[69] WO99/42130.
[70] WO2004/011027.
[71] WO96/40242.
[72] Lei et al. (2000) *Dev Biol (Basel)* 103:259-264.
[73] WO00/38711; U.S. Pat. No. 6,146,902.
[74] WO99/24578.
[75] WO99/36544.
[76] WO99/57280.
[77] WO00/22430.
[78] Tettelin et al. (2000) *Science* 287:1809-1815.
[79] WO96/29412.
[80] Pizza et al. (2000) *Science* 287:1816-1820.
[81] WO01/52885.
[82] Bjune et al. (1991) *Lancet* 338(8775): 1093-1096.
[83] Fukasawa et al. (1999) *Vaccine* 17:2951-2958.
[84] Rosenqvist et al. (1998) *Dev. Biol. Stand.* 92:323-333.
[85] Costantino et at (1992) *Vaccine* 10:691-698.
[86] WO03/007985.
[87] Watson (2000) *Pediatr Infect Dis J* 19:331-332.
[88] Rubin (2000) *Pediatr Clin North Am* 47:269-285, v.
[89] Jedrzejas (2001) *Microbiol Mol Biol Rev* 65:187-207.
[90] Bell (2000) *Pediatr Infect Dis J* 19:1187-1188.
[91] Iwarson (1995) *APMIS* 103:321-326.
[92] Gerlich et al. (1990) *Vaccine* 8 Suppl:S63-68 & 79-80.
[93] Hsu et al. (1999) *Clin Liver Dis* 3:901-915.
[94] Gustafsson et at (1996) *N. Engl. J. Med.* 334:349-355.
[95] Rappuoli et al. (1991) *TIBTECH* 9:232-238.
[96] *Vaccines* (2004) eds. Plotkin & Orenstein. ISBN 0-7216-9688-0.
[97] WO02/02606.
[98] Kalman et at (1999) *Nature Genetics* 21:385-389.
[99] Read et al. (2000) *Nucleic Acids Res* 28:1397-406.
[100] Shirai et al. (2000) *J. Infect. Dis.* 181(Suppl 3):S524-S527.
[101] WO99/27105.
[102] WO00/27994.
[103] WO00/37494.
[104] WO99/28475.
[105] Ross et al. (2001) *Vaccine* 19:4135-4142.
[106] Sutter et at (2000) *Pediatr Clin North Am* 47:287-308.
[107] Zimmerman & Spann (1999) *Am Fam Physician* 59:113-118, 125-126.
[108] Dreesen (1997) *Vaccine* 15 Suppl:S2-6.
[109] *MMWR Morb Mortal Wkly Rep* 1998 Jan. 16; 47(1): 12, 19.
[110] McMichael (2000) *Vaccine* 19 Suppl 1:S101-107.
[111] WO02/34771.
[112] Dale (1999) *Infect Dis Clin North Am* 13:227-43, viii.
[113] Ferretti et al. (2001) *PNAS USA* 98: 4658-4663.
[114] WO03/093306.
[115] WO2004/018646.
[116] WO2004/041157.
[117] Ichiman and Yoshida (1981) *J. Appl. Bacteriol.* 51:229.
[118] U.S. Pat. No. 4,197,290
[119] Ichiman et al. (1991) *J. Appl. Bacteriol.* 71:176.
[120] Robinson & Torres (1997) *Seminars in Immunology* 9:271-283.
[121] Donnelly et al. (1997) *Annu Rev Immunol* 15:617-648.
[122] Scott-Taylor & Dalgleish (2000) *Expert Opin Investig Drugs* 9:471-480.
[123] Apostolopoulos & Plebanski (2000) *Curr Opin Mol Ther* 2:441-447.
[124] Ilan (1999) *Curr Opin Mol Ther* 1:116-120.
[125] Dubensky et al. (2000) *Mol Med* 6:723-732.
[126] Robinson & Pertmer (2000) *Adv Virus Res* 55:1-74.
[127] Donnelly et at (2000) *Am J Respir Crit Care Med* 162(4 Pt 2):S190-193.
[128] Davis (1999) *Mt. Sinai J. Med.* 66:84-90.
[129] Gennaro (2000) *Remington: The Science and Practice of Pharmacy.* 20th edition, ISBN: 0683306472.
[130] Joyce et al. (2003) *Carbohydrate Research* 338:903.
[131] Maira-Litran et al. (2002) *Infect. Immun.* 70:4433.
[132] WO2004/043407.
[133] WO2007/13224.
[134] WO2004/043405
[135] WO98/10788.
[136] WO2007/053176.

[137] WO2007/113222.
[138] WO2005/009379.
[139] WO2009/029132.
[140] WO2008/079315.
[141] WO2005/086663.
[142] WO2005/115113.
[143] WO2006/033918.
[144] WO2006/078680.
[145] Kuroda et al. (2001) *Lancet* 357(9264):1225-1240; see also pages 1218-1219.
[146] Sjodahl (1977) *J. Biochem.* 73:343-351.
[147] Uhlen et al. (1984) *J. Biol. Chem.* 259:1695-1702 & 13628 (Corr.).
[148] Schneewind et al. (1992) *Cell* 70:267-281.
[149] DeDent et al. (2008) *EMBO J.* 27:2656-2668.
[150] Sjoquist et al. (1972) *Eur. J. Biochem.* 30:190-194.
[151] DeDent et al. (2007) *J. Bacteriol.* 189:4473-4484.
[152] Deisenhofer et al., (1978) *Hoppe-Seyh Zeitsch. Physiol. Chem.* 359:975-985.
[153] Deisenhofer (1981) *Biochemistry* 20:2361-2370.
[154] Graille et al. (2000) *Proc. Nat. Acad. Sci. USA* 97:5399-5404.
[155] O'Seaghdha et al. (2006) *FEBS J.* 273:4831-41.
[156] Gomez et al. (2006) *J. Biol. Chem.* 281:20190-20196.
[157] WO2007/071692.
[158] Sebulsky & Heinrichs (2001) *J Bacteriol* 183:4994-5000.
[159] Sebulsky et al. (2003) *J Biol Chem* 278:49890-900.
[160] WO2005/009378.
[161] Rable & Wardenburg (2009) *Infect Immun* 77:2712-8.
[162] WO2007/145689.
[163] WO2009/029831.
[164] WO2005/079315.
[165] WO2008/152447.
[166] Kuklin et al. (2006) *Infect Immun.* 74(4):2215-23.
[167] WO2005/009379.
[168] Gennaro (2000) *Remington: The Science and Practice of Pharmacy.* 20th edition, ISBN: 0683306472.
[169] *Methods In Enzymology* (S. Colowick and N. Kaplan, eds., Academic Press, Inc.)
[170] *Handbook of Experimental Immunology*, Vols. I-IV (D. M. Weir and C. C. Blackwell, eds, 1986, Blackwell Scientific Publications)
[171] Sambrook et al. (2001) *Molecular Cloning: A Laboratory Manual,* 3rd edition (Cold Spring Harbor Laboratory Press).
[172] *Handbook of Surface and Colloidal Chemistry* (Birdi, K. S. ed., CRC Press, 1997)
[173] Ausubel et al. (eds) (2002) *Short protocols in molecular biology,* 5th edition (Current Protocols).
[174] *Molecular Biology Techniques: An Intensive Laboratory Course,* (Ream et al., eds., 1998, Academic Press)
[175] *PCR (Introduction to Biotechniques Series),* 2nd ed. (Newton & Graham eds., 1997, Springer Verlag)
[176] *Current Protocols in Molecular Biology* (F. M. Ausubel et al., eds., 1987) Supplement 30
[177] Smith & Waterman (1981) *Adv. Appl. Math.* 2: 482-489.
[178] Geysen et al. (1984) *PNAS USA* 81:3998-4002.
[179] Carter (1994) *Methods Mol Biol* 36:207-23.
[180] Jameson, B A et al. 1988, *CABIOS* 4(1):181-186.
[181] Raddrizzani & Hammer (2000) *Brief Bioinform* 1(2): 179-89.
[182] Bublil et al. (2007) *Proteins* 68(1):294-304.
[183] De Lalla et al. (1999) *J. Immunol.* 163:1725-29.
[184] Kwok et al. (2001) *Trends Immunol* 22:583-88.
[185] Brusic et al. (1998) *Bioinformatics* 14(2): 121-30
[186] Meister et al. (1995) *Vaccine* 13(6):581-91.
[187] Roberts et al. (1996) *AIDS Res Hum Retroviruses* 12(7):593-610.
[188] Maksyutov & Zagrebelnaya (1993) *Comput Appl Biosci* 9(3):291-7.
[189] Feller & de la Cruz (1991) *Nature* 349(6311):720-1.
[190] Hopp (1993) *Peptide Research* 6:183-190.
[191] Welling et al. (1985) *FEBS Lett.* 188:215-218.
[192] Davenport et al. (1995) *Immunogenetics* 42:392-297.
[193] Tsurui & Takahashi (2007) *J Pharmacol Sci.* 105(4): 299-316.
[194] Tong et al. (2007) *Brief Bioinform.* 8(2):96-108.
[195] Schirle et al. (2001) *J Immunol Methods.* 257(1-2):1-16.
[196] Chen et al. (2007) *Amino Acids* 33(3):423-8.
[197] Kim et al. (2008) *Biochemistry* 47(12):3822-3831.
[198] Patti et al. (2008) *Biochemistry* 47(32):8378-8385.
[199] Kim and Schaefer (2008) *Biochemistry* 47(38):10155-10161.
[200] Biswas (2006) PhD Thesis: *Characterization of Staphylococcus aureus peptidoglycan hydrolases and isolation of defined peptidoglycan structures* der Eberhard Karls Universität Tübingen

We claim:

1. A method for releasing capsular polysaccharide from *S. aureus* type 8 cells, comprising the step of treating the cells with acid, wherein the acid treatment results in the capsular polysaccharide having a degree of O-acetylation between 60-100%.

2. The method of claim 1, wherein the cells are in the form of a wet cell paste or are suspended in an aqueous medium.

3. The method of claim 1, wherein the acid treatment is carried out using acetic acid.

4. The method of claim 1, wherein the method further comprises a step of neutralisation.

5. The method of claim 1, wherein the method further comprises a step of centrifugation of the cells and collection of the polysaccharide-containing supernatant.

6. A process for purifying capsular polysaccharide from *S. aureus* type 8 cells comprising the method of claim 1 followed by a step selected from: treatment of the capsular polysaccharide with DNase and/or RNase, treatment of the capsular polysaccharide with mutanolysin, diafiltration, tangential flow filtration, anion exchange chromatography, gel filtration, and concentration of the polysaccharide.

7. The process of claim 6, wherein the step is treatment of the capsular polysaccharide with DNase and/or RNase.

8. The process of claim 6, wherein the step is treatment of the capsular polysaccharide with mutanolysin.

9. The process of claim 6, wherein the process further comprises a step of conjugation to a carrier molecule.

10. The process of claim 6, wherein the step is diafiltration.

11. The process of claim 10, wherein the diafiltration is tangential flow filtration.

12. The process of claim 6, wherein the step is anion exchange chromatography.

13. The process of claim 6, wherein the step is gel filtration.

14. The process of claim 6, wherein the step is concentration of the polysaccharide.

15. The process of claim 6, wherein the molecular mass of the purified polysaccharide is between 2-3500 kDa.

16. The process of claim 6, wherein the process further comprises a step of depolymerisation of the purified polysaccharide to form an oligosaccharide.

17. The process of claim 6, wherein the process further comprises a step of sterile filtration.

18. The process of claim 6, wherein the process provides a composition comprising the polysaccharide and a level of peptidoglycan contamination that is less than 5% by weight peptidoglycan relative to the total weight of the polysaccharide.

19. The process of claim 18, wherein the level of peptidoglycan contamination is about 2% by weight peptidoglycan relative to the total weight of the polysaccharide.

20. The process of claim 6, wherein the process provides a composition comprising the polysaccharide and a level of protein contamination that is less than 5% by weight protein relative to the total weight of the polysaccharide.

21. The process of claim 6, wherein the process provides a composition comprising the polysaccharide and a level of nucleic acid contamination that is less than 1% by weight nucleic acid relative to the total weight of the polysaccharide.

* * * * *